(12) United States Patent
Blackley

(10) Patent No.: US 10,088,463 B2
(45) Date of Patent: Oct. 2, 2018

(54) CALIBRATING ELECTRONIC VAPOR DEVICE

(71) Applicant: Lunatech, LLC, Studio City, CA (US)

(72) Inventor: Jonathan Seamus Blackley, South Pasadena, CA (US)

(73) Assignee: LunaTech, LLC, Encino, CA (US)

( * ) Notice: Subject to any disclaimer, the term of this patent is extended or adjusted under 35 U.S.C. 154(b) by 44 days.

(21) Appl. No.: 15/180,011

(22) Filed: Jun. 11, 2016

(65) Prior Publication Data

US 2016/0363570 A1    Dec. 15, 2016

Related U.S. Application Data

(60) Provisional application No. 62/174,053, filed on Jun. 11, 2015.

(51) Int. Cl.

| | |
|---|---|
| *G01N 31/00* | (2006.01) |
| *G01N 33/00* | (2006.01) |
| *A24F 47/00* | (2006.01) |
| *H04W 4/08* | (2009.01) |
| *A61M 15/06* | (2006.01) |
| *A61M 16/10* | (2006.01) |
| *A61M 11/04* | (2006.01) |

(Continued)

(52) U.S. Cl.
CPC ....... *G01N 33/0006* (2013.01); *A24F 47/002* (2013.01); *A61M 11/042* (2014.02); *A61M 15/0003* (2014.02); *A61M 15/008* (2014.02); *A61M 15/06* (2013.01); *A61M 16/024* (2017.08); *A61M 16/107* (2014.02); *A61M 16/1055* (2013.01); *G01N 33/0027* (2013.01); *H04W 4/08* (2013.01); *A61M 15/08* (2013.01); *A61M 2205/3368* (2013.01); *A61M 2205/3375* (2013.01); *A61M 2205/3553* (2013.01); *A61M 2205/3584* (2013.01); *A61M 2205/3592* (2013.01); *A61M 2205/3653* (2013.01); *A61M 2205/3693* (2013.01); *A61M 2205/505* (2013.01); *A61M 2205/581* (2013.01); *A61M 2205/582* (2013.01); *A61M 2205/584* (2013.01); *A61M 2205/609* (2013.01); *A61M 2205/702* (2013.01); *A61M 2205/8206* (2013.01); *H04L 63/083* (2013.01); *H04W 12/08* (2013.01)

(58) Field of Classification Search
None
See application file for complete search history.

(56) References Cited

U.S. PATENT DOCUMENTS 5,092,217 A * 3/1992 Achter ............... G01N 1/02
73/1.04
5,452,600 A * 9/1995 Davies ............. G01N 33/0006
261/96

(Continued)

*Primary Examiner* — Aditya Bhat
(74) *Attorney, Agent, or Firm* — Susan L. McCain; Hankin Patent Law, APC

(57) ABSTRACT

A method is disclosed comprising drawing vapor from a vapor device, exposing the drawn vapor to a sensor, determining a condition of the drawn vapor via the sensor, collecting data related to the condition of the drawn vapor from the sensor, comparing the collected data to standardized vapor device output data, determining a calibration result based on the comparison, determining a configuration adjustment based on the calibration result, and transmitting the configuration adjustment to the vapor device.

19 Claims, 22 Drawing Sheets

(51) Int. Cl.
  *A61M 15/00* (2006.01)
  *A61M 16/00* (2006.01)
  *A61M 15/08* (2006.01)
  *H04L 29/06* (2006.01)
  *H04W 12/08* (2009.01)

(56) References Cited

U.S. PATENT DOCUMENTS

| | | | |
|---|---|---|---|
| 5,493,890 A * | 2/1996 | Dussault | G01N 33/0006 |
| | | | 73/1.06 |
| 5,563,339 A * | 10/1996 | Compton | G01N 7/16 |
| | | | 73/29.01 |
| 6,627,444 B1 * | 9/2003 | Goledzinowski | G01N 21/278 |
| | | | 250/281 |
| 8,757,147 B2 | 6/2014 | Terry et al. | |
| 8,820,330 B2 | 9/2014 | Bellinger | |
| 8,851,083 B2 | 10/2014 | Oglesby et al. | |
| 8,955,522 B1 | 2/2015 | Bowen et al. | |
| 9,408,416 B2 | 8/2016 | Monsees et al. | |
| 9,498,002 B1 | 11/2016 | Soreide | |
| 9,585,981 B2 | 3/2017 | Wynalda, Jr. | |
| 2007/0042792 A1 | 2/2007 | Perfetto et al. | |
| 2015/0161883 A1 | 6/2015 | Satgunam | |
| 2015/0181924 A1 | 7/2015 | Llamas | |
| 2015/0013695 A1 | 12/2015 | Righetti | |
| 2015/0351449 A1 | 12/2015 | Righetti | |
| 2016/0157524 A1 | 6/2016 | Bowen | |
| 2016/0198759 A1 | 7/2016 | Kuntawala | |
| 2016/0345621 A1 | 12/2016 | Li | |
| 2016/0366928 A1 | 12/2016 | Liu | |
| 2017/0079322 A1 | 3/2017 | Li et al. | |

* cited by examiner

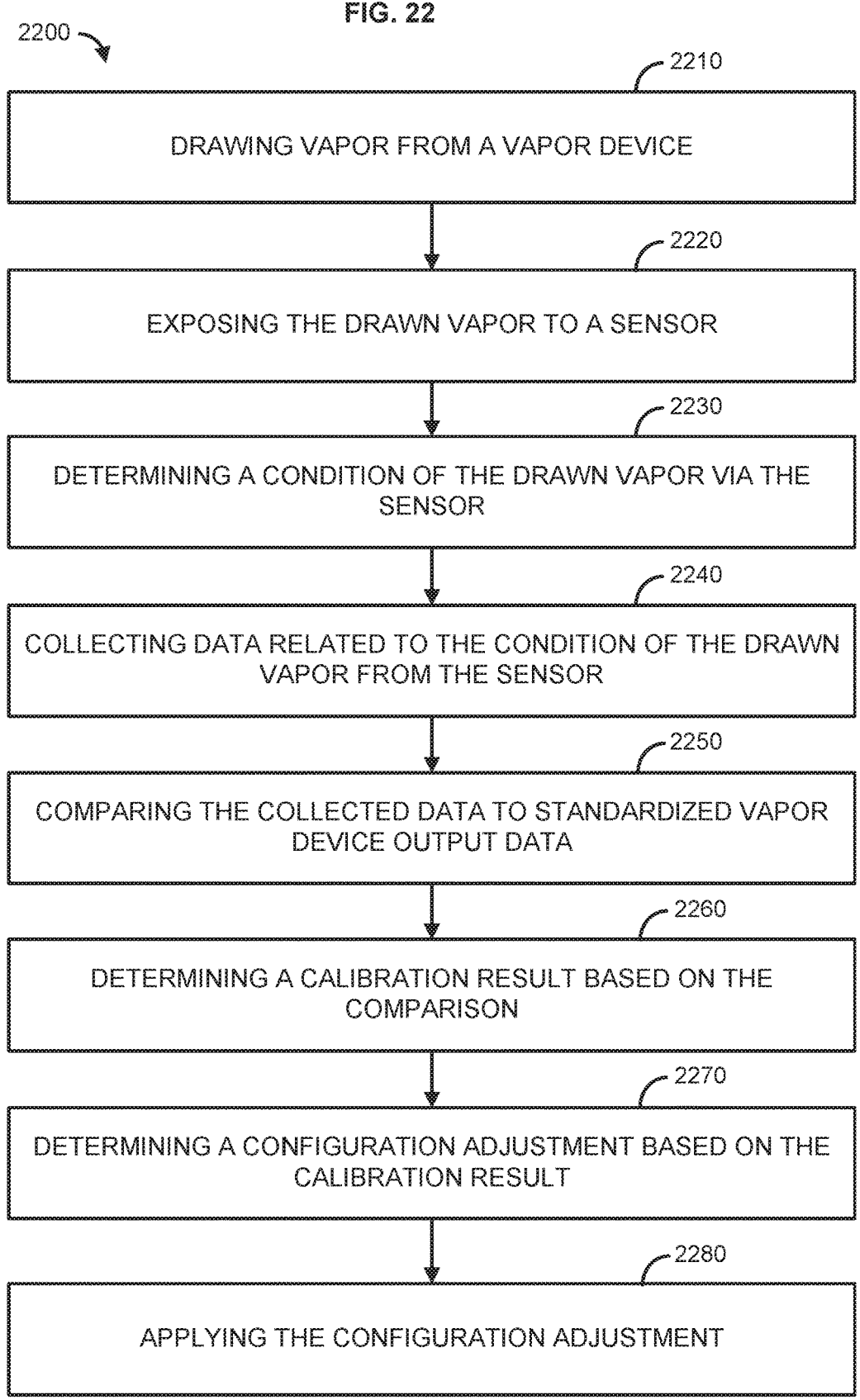

CALIBRATING ELECTRONIC VAPOR DEVICE

CROSS REFERENCE TO RELATED PATENT APPLICATION

This application claims priority to U.S. Provisional Application No. 62/174,053 filed Jun. 11, 2015, here incorporated by reference in its entirety.

BACKGROUND

Various types of personal vaporizers have been known in the art for many years. In general, such vaporizers are characterized by heating a solid to a smoldering point, vaporizing a liquid by heat, or nebulizing a liquid by heat and/or by expansion through a nozzle. Such devices are designed to release aromatic materials in the solid or liquid while avoiding high temperatures of combustion and associated formation of tars, carbon monoxide, or other harmful byproducts. Preferably, the device releases a very fine mist with a mouth feel similar to smoke, under suction. Thus, a vaporizing device can be made to mimic traditional smoking articles such as cigarettes, cigars, pipes and hookahs in certain aspects, while avoiding significant adverse health effects of traditional tobacco or other herbal consumption.

Concerns have been raised, however, about the dose of active compounds administered by a vaporizer, and the possible presence of trace contaminants. Consumers of vaporizers must generally rely on the representations of suppliers with regard to purity and composition of vaporizer outputs and inputs (e.g., vaporizing fluid). Presently, there is no convenient way for consumers to test the actual output of the vaporizers they are using.

Similarly, consumers purchase and use a wide variety of air fresheners or the like, with very little or no information about the compounds that these products are emitting into the breathable air space and that they are exposing their bodies to. Presently, consumers have no convenient way to really know and control what compounds they are exposing themselves to by using air fresheners or similar products. Moreover, consumers have no convenient way, or no way at all, to control which compound, or which mix of compounds, are emitted into an air space for air freshening, air treatment, personal therapy, recreation, or for any other purpose.

It would be desirable, therefore, to develop new technologies for such applications, that overcomes these and other limitations of the prior art, and enhances the utility of vaporizers, analysis equipment, and air treatment equipment.

SUMMARY

It is to be understood that both the following general description and the following detailed description are exemplary and explanatory only and are not restrictive. In an aspect, an apparatus is disclosed comprising an intake, configured to be coupled to a vapor device, a pump coupled to the air intake, configured for drawing vapor from the vapor device via the intake, a sensor, coupled to the pump, configured for detecting a condition of the drawn vapor, a memory, configured for storing standardized vapor device output data, a processor, coupled to the memory and the sensor, configured for, collecting data related to the condition of the drawn vapor from the sensor, comparing the collected data to the standardized vapor device output data, determining a calibration result based on the comparison, and determining a configuration adjustment based on the calibration result, and a network access device, coupled to the processor, configured for transmitting the configuration adjustment to the vapor device.

In an aspect, a method is disclosed comprising drawing vapor from a vapor device, exposing the drawn vapor to a sensor, determining a condition of the drawn vapor via the sensor, collecting data related to the condition of the drawn vapor from the sensor, comparing the collected data to standardized vapor device output data, determining a calibration result based on the comparison, determining a configuration adjustment based on the calibration result, and transmitting the configuration adjustment to the vapor device.

In an aspect, an apparatus is disclosed comprising an intake, configured to be coupled to a standardized vapor device, a pump coupled to the air intake, configured for drawing vapor from the standardized vapor device via the intake, a sensor, coupled to the pump, configured for detecting a condition of the drawn vapor, a memory, configured for storing standardized vapor device output data, a processor, coupled to the memory and the sensor, configured for, collecting data related to the condition of the drawn vapor from the sensor, comparing the collected data to the standardized vapor device output data, determining a calibration result based on the comparison, and determining a configuration adjustment based on the calibration result, and applying the configuration adjustment to the apparatus.

In an aspect, a method is disclosed comprising drawing vapor from a standardized vapor device, exposing the drawn vapor to a sensor, determining a condition of the drawn vapor via the sensor, collecting data related to the condition of the drawn vapor from the sensor, comparing the collected data to standardized vapor device output data, determining a calibration result based on the comparison, determining a configuration adjustment based on the calibration result, and applying the configuration adjustment.

Additional advantages will be set forth in part in the description which follows or can be learned by practice. The advantages will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE DRAWINGS

The features, nature, and advantages of the present disclosure will become more apparent from the detailed description set forth below when taken in conjunction with the drawings, in which like reference characters are used to identify like elements correspondingly throughout the specification and drawings.

FIG. 22 illustrates an exemplary method.

DETAILED DESCRIPTION

Figure 1:
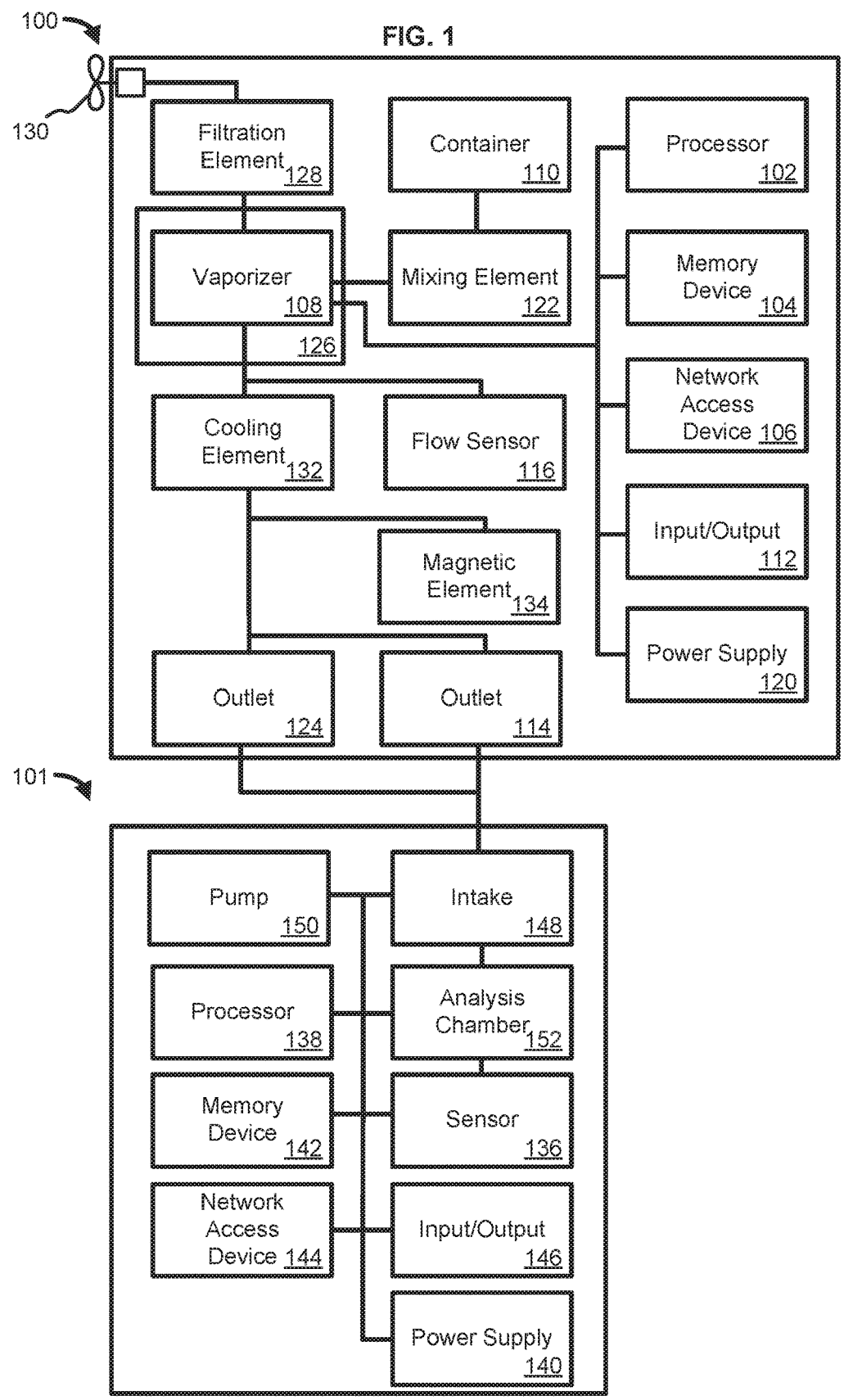
FIG. 1 illustrates a block diagram of an exemplary electronic vapor device.

Before the present methods and systems are disclosed and described, it is to be understood that the methods and systems are not limited to specific methods, specific components, or to particular implementations. It is also to be understood that the terminology used herein is for the purpose of describing particular embodiments only and is not intended to be limiting.

As used in the specification and the appended claims, the singular forms "a," "an," and "the" include plural referents unless the context clearly dictates otherwise. Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently the other endpoint.

"Optional" or "optionally" means that the subsequently described event or circumstance may or may not occur, and that the description includes instances where said event or circumstance occurs and instances where it does not.

Throughout the description and claims of this specification, the word "comprise" and variations of the word, such as "comprising" and "comprises," means "including but not limited to," and is not intended to exclude, for example, other components, integers or steps. "Exemplary" means "an example of" and is not intended to convey an indication of a preferred or ideal embodiment. "Such as" is not used in a restrictive sense, but for explanatory purposes.

Disclosed are components that can be used to perform the disclosed methods and systems. These and other components are disclosed herein, and it is understood that when combinations, subsets, interactions, groups, etc. of these components are disclosed that while specific reference of each various individual and collective combinations and permutation of these may not be explicitly disclosed, each is specifically contemplated and described herein, for all methods and systems. This applies to all aspects of this application including, but not limited to, steps in disclosed methods. Thus, if there are a variety of additional steps that can be performed it is understood that each of these additional steps can be performed with any specific embodiment or combination of embodiments of the disclosed methods.

The present methods and systems can be understood more readily by reference to the following detailed description of preferred embodiments and the examples included therein and to the Figures and their previous and following description.

As will be appreciated by one skilled in the art, the methods and systems may take the form of an entirely hardware embodiment, an entirely software embodiment, or an embodiment combining software and hardware aspects. Furthermore, the methods and systems may take the form of a computer program product on a computer-readable storage medium having computer-readable program instructions (e.g., computer software) embodied in the storage medium. More particularly, the present methods and systems may take the form of web-implemented computer software. Any suitable computer-readable storage medium can be utilized including hard disks, CD-ROMs, optical storage devices, or magnetic storage devices.

Embodiments of the methods and systems are described below with reference to block diagrams and flowchart illustrations of methods, systems, apparatuses and computer program products. It will be understood that each block of the block diagrams and flowchart illustrations, and combinations of blocks in the block diagrams and flowchart illustrations, respectively, can be implemented by computer program instructions. These computer program instructions can be loaded onto a general purpose computer, special purpose computer, or other programmable data processing apparatus to produce a machine, such that the instructions which execute on the computer or other programmable data processing apparatus create a means for implementing the functions specified in the flowchart block or blocks.

These computer program instructions may also be stored in a computer-readable memory that can direct a computer or other programmable data processing apparatus to function in a particular manner, such that the instructions stored in the computer-readable memory produce an article of manufacture including computer-readable instructions for implementing the function specified in the flowchart block or blocks. The computer program instructions may also be loaded onto a computer or other programmable data processing apparatus to cause a series of operational steps to be performed on the computer or other programmable apparatus to produce a computer-implemented process such that the instructions that execute on the computer or other programmable apparatus provide steps for implementing the functions specified in the flowchart block or blocks.

Accordingly, blocks of the block diagrams and flowchart illustrations support combinations of means for performing the specified functions, combinations of steps for performing the specified functions and program instruction means for performing the specified functions. It will also be understood that each block of the block diagrams and flowchart illustrations, and combinations of blocks in the block diagrams and flowchart illustrations, can be implemented by special purpose hardware-based computer systems that perform the specified functions or steps, or combinations of special purpose hardware and computer instructions.

Various aspects are now described with reference to the drawings. In the following description, for purposes of explanation, numerous specific details are set forth in order to provide a thorough understanding of one or more aspects. It can be evident, however, that the various aspects can be practiced without these specific details. In other instances, well-known structures and devices are shown in block diagram form in order to facilitate describing these aspects.

While embodiments of the disclosure are directed to vaporizing devices, it should be appreciated that aspects of the technology can be adapted by one of ordinary skill to nebulizing devices designed to produce an inhalable mist or aerosol.

The present disclosure relates to methods and apparatus for calibrating output of an electronic vapor device, or for using an electronic vapor device to calibrate a vapor testing apparatus.

In an aspect of the disclosure, an air analyzer and treatment system that can determine the presence or concentration of active compounds or substances of concern in an airspace, and can provide a desired air treatment. The air analyzer and treatment system may include a suction mechanism configured to draw an output from an air space. The suction mechanism is in fluid communication with at least one of a gas testing assembly or an exhaust port to ambient air, and may be communicatively coupled to a network communication device via a processor or the like. For example, the suction mechanism may be coupled to the gas testing assembly by a component that enables an exchange of fluid, or an operative part of the gas testing assembly may be in contact with air/vapor inside the suction mechanism. The air analyzer and air treatment apparatus may further include a processor operatively coupled to at least one of the suction mechanism, the gas testing assembly, or the network communication device. Optionally, the suction mechanism may be configured to draw the air from the airspace through a personal vaporizer interposed between a suction inlet and the airspace.

When including the gas testing assembly, the processor may be further configured to receive measurement data from the gas testing assembly. The gas testing assembly may include at least one of a gas sensor circuit, or a GC/MS assembly.

The processor may be configured to perform at least one of analyzing the measurement data, sending the measurement data to a network node, or receiving an analysis of the measurement data from the network node. Accordingly, the air analyzer and air treatment apparatus may further include a user interface port, wherein the processor is configured to determine a material to be measured based on an input from the user interface port. The user interface port may be configured to couple to at least one of a vaporizer or a mobile computing device. The processor may be configured to activate a gas or vapor sensor circuit based on the material to be measured.

In an aspect, the suction mechanism further comprises at least one of a variable stroke piston, variable stroke bellows, or a gas pump. The mechanism may further be configured to draw air or vapor at a variable rate. For example, the suction mechanism may be configured to draw air into an interior volume at a rate controlled at least in part by the processor.

The air analyzer and air treatment apparatus may include at least one of an internal vaporizer or a control coupling to a detachable vaporizer. The processor may be configured to control vapor output of at least one of the internal vaporizer or the detachable vaporizer.

In an aspect, the processor may be configured to control the vapor output for a defined vapor concentration target in a confined space. Thus, the air analyzer and air treatment apparatus may be used as a vapor dispensing device for a room or confined space. Accordingly, the processor may be configured to control the vapor output based on at least one of a default setting, a remote authorized order, current measurement data, archived measurement data, system rules, or a custom formulation of multiple vaporizable materials.

In addition, the processor may be configured to determine test parameters for calibrating the apparatus. In that regard, the processor can receive or determine known values of a standardized material, for example, by searching a database using an identifier. The processor can also use data detected from sensors to obtain a measurement of at least one constituent of the standardized material. The sensors may include a GC device, an MS device, an electrochemical detecting device, a carbon nanotube detector, an infrared absorption device, and/or a semiconductor electrochemical sensing device. The processor can compare the known values to the determined measurement to determine whether the apparatus is calibrated.

If the apparatus is not calibrated, the processor can determine a calibration result, or calibration parameter, indicating how the apparatus can be calibrated. The calibration parameter may be determined based on the comparison of the known values to the determined measurement. The calibration parameter may include, for example, adjusting a measurement parameter of the apparatus, recalibrating a physical component, such as a GC, an MS, or a sensor, adjusting data ratios in a database or replacing one or more sensor. The calibration parameter may also or instead include adjusting an intake volume, cleaning an internal mechanism, checking one or more power systems of the apparatus, or checking a status of a communication channel. Instead or additionally, the processor can determine the calibration result by comparing the determined measurement to similar measurements of another vapor analysis device. After determining the calibration parameter, the processor can implement the calibration parameter and/or provide instructions for implementing the calibration parameter.

When the apparatus is properly calibrated, the processor can generate an output indicating that the apparatus is calibrated, and may output the calibration results. The calibration results may or may not be provided to a database and/or another vapor analysis device.

FIG. 1 is a block diagram of an exemplary electronic vapor device 100 coupled to a robotic vapor device (RVD) 101 (also referred to as a respiration simulating analysis and distribution device), as described herein. The electronic vapor device 100 can be, for example, an e-cigarette, an e-cigar, a hybrid electronic communication handset coupled/integrated vapor device, a modified vapor device "mod," a micro-sized electronic vapor device, and the like. The vapor device 100 can comprise any suitable housing for enclosing and protecting the various components disclosed herein. The vapor device 100 can comprise a processor 102. The processor 102 can be, or can comprise, any suitable microprocessor or microcontroller, for example, a low-power application-specific controller (ASIC) and/or a field programmable gate array (FPGA) designed or programmed specifically for the task of controlling a device as described herein, or a general purpose central processing unit (CPU), for example, one based on 80×86 architecture as designed by Intel™ or AMD™, or a system-on-a-chip as designed by ARM™. The processor 102 can be coupled (e.g., communicatively, operatively, etc. . . . ) to auxiliary devices or modules of the vapor device 100 using a bus or other coupling. The vapor device 100 can comprise a power supply 120. The power supply 120 can comprise one or more batteries and/or other power storage device (e.g., capacitor)

and/or a port for connecting to an external power supply. For example, an external power supply can supply power to the vapor device 100 and a battery can store at least a portion of the supplied power. The one or more batteries can be rechargeable. The one or more batteries can comprise a lithium-ion battery (including thin film lithium ion batteries), a lithium ion polymer battery, a nickel-cadmium battery, a nickel metal hydride battery, a lead-acid battery, combinations thereof, and the like. In an aspect, the power supply 120 can receive power via a power coupling to a case, wherein the vapor device 100 is stored in the case.

The vapor device 100 can comprise a memory device 104 coupled to the processor 102. The memory device 104 can comprise a random access memory (RAM) configured for storing program instructions and data for execution or processing by the processor 102 during control of the vapor device 100. When the vapor device 100 is powered off or in an inactive state, program instructions and data can be stored in a long-term memory, for example, a non-volatile magnetic optical, or electronic memory storage device (not shown). Either or both of the RAM or the long-term memory can comprise a non-transitory computer-readable medium storing program instructions that, when executed by the processor 102, cause the vapor device 100 to perform all or part of one or more methods and/or operations described herein. Program instructions can be written in any suitable high-level language, for example, C, C++, C# or the Java™, and compiled to produce machine-language code for execution by the processor 102.

In an aspect, the vapor device 100 can comprise a network access device 106 allowing the vapor device 100 to be coupled to one or more ancillary devices (not shown) such as via an access point (not shown) of a wireless telephone network, local area network, or other coupling to a wide area network, for example, the Internet. In that regard, the processor 102 can be configured to share data with the one or more ancillary devices via the network access device 106. The shared data can comprise, for example, usage data and/or operational data of the vapor device 100, a status of the vapor device 100, a status and/or operating condition of one or more the components of the vapor device 100, text to be used in a message, a product order, payment information, and/or any other data. Similarly, the processor 102 can be configured to receive control instructions from the one or more ancillary devices via the network access device 106. For example, a configuration of the vapor device 100, an operation of the vapor device 100, and/or other settings of the vapor device 100, can be controlled by the one or more ancillary devices via the network access device 106. For example, an ancillary device can comprise a server that can provide various services and another ancillary device can comprise a smartphone for controlling operation of the vapor device 100. In some aspects, the smartphone or another ancillary device can be used as a primary input/output of the vapor device 100 such that data is received by the vapor device 100 from the server, transmitted to the smartphone, and output on a display of the smartphone. In an aspect, data transmitted to the ancillary device can comprise a mixture of vaporizable material and/or instructions to release vapor. For example, the vapor device 100 can be configured to determine a need for the release of vapor into the atmosphere. The vapor device 100 can provide instructions via the network access device 106 to an ancillary device (e.g., another vapor device) to release vapor into the atmosphere.

In an aspect, the vapor device 100 can also comprise an input/output device 112 coupled to one or more of the processor 102, a vaporizer 108, the network access device 106, and/or any other electronic component of the vapor device 100. Input can be received from a user or another device and/or output can be provided to a user or another device via the input/output device 112. The input/output device 112 can comprise any combinations of input and/or output devices such as buttons, knobs, keyboards, touchscreens, displays, light-emitting elements, a speaker, and/or the like. In an aspect, the input/output device 112 can comprise an interface port (not shown) such as a wired interface, for example a serial port, a Universal Serial Bus (USB) port, an Ethernet port, or other suitable wired connection. The input/output device 112 can comprise a wireless interface (not shown), for example a transceiver using any suitable wireless protocol, for example WiFi (IEEE 802.11), Bluetooth®, infrared, or other wireless standard. For example, the input/output device 112 can communicate with a smartphone via Bluetooth® such that the inputs and outputs of the smartphone can be used by the user to interface with the vapor device 100. In an aspect, the input/output device 112 can comprise a user interface. The user interface user interface can comprise at least one of lighted signal lights, gauges, boxes, forms, check marks, avatars, visual images, graphic designs, lists, active calibrations or calculations, 2D interactive fractal designs, 3D fractal designs, 2D and/or 3D representations of vapor devices and other interface system functions.

In an aspect, the input/output device 112 can be coupled to an adaptor device to receive power and/or send/receive data signals from an electronic device. For example, the input/output device 112 can be configured to receive power from the adaptor device and provide the power to the power supply 120 to recharge one or more batteries. The input/output device 112 can exchange data signals received from the adaptor device with the processor 102 to cause the processor to execute one or more functions.

In an aspect, the input/output device 112 can comprise a touchscreen interface and/or a biometric interface. For example, the input/output device 112 can include controls that allow the user to interact with and input information and commands to the vapor device 100. For example, with respect to the embodiments described herein, the input/output device 112 can comprise a touch screen display. The input/output device 112 can be configured to provide the content of the exemplary screen shots shown herein, which are presented to the user via the functionality of a display. User inputs to the touch screen display are processed by, for example, the input/output device 112 and/or the processor 102. The input/output device 112 can also be configured to process new content and communications to the system 100. The touch screen display can provide controls and menu selections, and process commands and requests. Application and content objects can be provided by the touch screen display. The input/output device 112 and/or the processor 102 can receive and interpret commands and other inputs, interface with the other components of the vapor device 100 as required. In an aspect, the touch screen display can enable a user to lock, unlock, or partially unlock or lock, the vapor device 100. The vapor device 100 can be transitioned from an idle and locked state into an open state by, for example, moving or dragging an icon on the screen of the vapor device 100, entering in a password/passcode, and the like. The input/output device 112 can thus display information to a user such as a puff count, an amount of vaporizable material remaining in the container 110, battery remaining, signal strength, combinations thereof, and the like.

In an aspect, the input/output device 112 can comprise an audio user interface. A microphone can be configured to receive audio signals and relay the audio signals to the input/output device 112. The audio user interface can be any interface that is responsive to voice or other audio commands. The audio user interface can be configured to cause an action, activate a function, etc, by the vapor device 100 (or another device) based on a received voice (or other audio) command. The audio user interface can be deployed directly on the vapor device 100 and/or via other electronic devices (e.g., electronic communication devices such as a smartphone, a smart watch, a tablet, a laptop, a dedicated audio user interface device, and the like). The audio user interface can be used to control the functionality of the vapor device 100. Such functionality can comprise, but is not limited to, custom mixing of vaporizable material (e.g., eLiquids) and/or ordering custom made eLiquid combinations via an eCommerce service (e.g., specifications of a user's custom flavor mix can be transmitted to an eCommerce service, so that an eLiquid provider can mix a custom eLiquid cartridge for the user). The user can then reorder the custom flavor mix anytime or even send it to friends as a present, all via the audio user interface. The user can also send via voice command a mixing recipe to other users. The other users can utilize the mixing recipe (e.g., via an electronic vapor device having multiple chambers for eLiquid) to sample the same mix via an auto-order to the other users' devices to create the received mixing recipe. A custom mix can be given a title by a user and/or can be defined by parts (e.g., one part liquid A and two parts liquid B). The audio user interface can also be utilized to create and send a custom message to other users, to join eVapor clubs, to receive eVapor chart information, and to conduct a wide range of social networking, location services and eCommerce activities. The audio user interface can be secured via a password (e.g., audio password) which features at least one of tone recognition, other voice quality recognition and, in one aspect, can utilize at least one special cadence as part of the audio password.

The input/output device 112 can be configured to interface with other devices, for example, exercise equipment, computing equipment, communications devices and/or other vapor devices, for example, via a physical or wireless connection. The input/output device 112 can thus exchange data with the other equipment. A user may sync their vapor device 100 to other devices, via programming attributes such as mutual dynamic link library (DLL) 'hooks'. This enables a smooth exchange of data between devices, as can a web interface between devices. The input/output device 112 can be used to upload one or more profiles to the other devices. Using exercise equipment as an example, the one or more profiles can comprise data such as workout routine data (e.g., timing, distance, settings, heart rate, etc. . . . ) and vaping data (e.g., eLiquid mixture recipes, supplements, vaping timing, etc. . . . ). Data from usage of previous exercise sessions can be archived and shared with new electronic vapor devices and/or new exercise equipment so that history and preferences may remain continuous and provide for simplified device settings, default settings, and recommended settings based upon the synthesis of current and archival data. The input/output device 112 can be configured to exchange data with the robotic vapor device 101. For example, the vapor device 100 can transmit data related to a vaporization process being performed by the vapor device 100 to the robotic vapor device 101 (e.g., any data related to a vaporizer 108, a rate of vaporization, a temperature, a quantity of vaporizable material, an identification of vaporizable material or mixture thereof, usage of one or more of a cooling element 132, a magnetic element 134, and a heating casing 126, combinations thereof, and the like).

In an aspect, the vapor device 100 can comprise a vaporizer 108. The vaporizer 108 can be coupled to one or more containers 110. Each of the one or more containers 110 can be configured to hold one or more vaporizable or non-vaporizable materials. The vaporizer 108 can receive the one or more vaporizable or non-vaporizable materials from the one or more containers 110 and heat the one or more vaporizable or non-vaporizable materials until the one or more vaporizable or non-vaporizable materials achieve a vapor state. In various embodiments, instead of heating the one or more vaporizable or non-vaporizable materials, the vaporizer 108 can nebulize or otherwise cause the one or more vaporizable or non-vaporizable materials in the one or more containers 110 to reduce in size into particulates. In various embodiments, the one or more containers 110 can comprise a compressed liquid that can be released to the vaporizer 108 via a valve or another mechanism. In various embodiments, the one or more containers 110 can comprise a wick (not shown) through which the one or more vaporizable or non-vaporizable materials is drawn to the vaporizer 108. The one or more containers 110 can be made of any suitable structural material, such as, an organic polymer, metal, ceramic, composite, or glass material. In an aspect, the vaporizable material can comprise one or more of, a Propylene Glycol (PG) based liquid, a Vegetable Glycerin (VG) based liquid, a water based liquid, combinations thereof, and the like. In an aspect, the vaporizable material can comprise Tetrahydrocannabinol (THC), Cannabidiol (CBD), cannabinol (CBN), combinations thereof, and the like. In a further aspect, the vaporizable material can comprise an extract from *duboisia hopwoodii*.

In an aspect, the vapor device 100 can comprise a mixing element 122. The mixing element 122 can be coupled to the processor 102 to receive one or more control signals. The one or more control signals can instruct the mixing element 122 to withdraw specific amounts of fluid from the one or more containers 110. The mixing element can, in response to a control signal from the processor 102, withdraw select quantities of vaporizable material in order to create a customized mixture of different types of vaporizable material. The liquid withdrawn by the mixing element 122 can be provided to the vaporizer 108.

The vapor device 100 may include a plurality of valves, wherein a respective one of the valves is interposed between the vaporizer 108 and a corresponding one of outlet 114 and/or outlet 124 (e.g., one or more inlets of flexible tubes). Each of the valves may control a flow rate through a respective one of the flexible tubes. For example, each of the plurality of valves may include a lumen of adjustable effective diameter for controlling a rate of vapor flow therethrough. The assembly may include an actuator, for example a motor, configured to independently adjust respective ones of the valves under control of the processor. The actuator may include a handle or the like to permit manual valve adjustment by the user. The motor or actuator can be coupled to a uniform flange or rotating spindle coupled to the valves and configured for controlling the flow of vapor through each of the valves. Each of the valves can be adjusted so that each of the flexible tubes accommodate the same (equal) rate of vapor flow, or different rates of flow. The processor 102 can be configured to determine settings for the respective ones of the valves each based on at least one of: a selected user preference or an amount of suction applied to a corresponding one of the flexible tubes. A user preference can be determined by the processor 102 based on a user input, which can be electrical or mechanical. An electrical input can be provided, for example, by a touchscreen, keypad, switch, or potentiometer (e.g., the input/output 112). A mechanical input can be provided, for example, by applying suction to a mouthpiece of a tube, turning a valve handle, or moving a gate piece.

The vapor device 100 may further include at least one light-emitting element positioned on or near each of the outlet 114 and/or the outlet 124 (e.g., flexible tubes) and configured to illuminate in response to suction applied to the outlet 114 and/or the outlet 124. At least one of an intensity of illumination or a pattern of alternating between an illuminated state and a non-illuminated state can be adjusted based on an amount of suction. One or more of the at least one light-emitting element, or another light-emitting element, may illuminate based on an amount of vaporizable material available. For example, at least one of an intensity of illumination or a pattern of alternating between an illuminated state and a non-illuminated state can be adjusted based on an amount of the vaporizable material within the vapor device 100. In some aspects, the vapor device 100 may include at least two light-emitting elements positioned on each of the outlet 114 and/or the outlet 124. Each of the at least two light-emitting elements may include a first light-emitting element and an outer light-emitting element positioned nearer the end of the outlet 114 and/or the outlet 124 than the first light-emitting element. Illumination of the at least two light-emitting elements may indicate a direction of a flow of vapor.

In an aspect, input from the input/output device 112 can be used by the processor 102 to cause the vaporizer 108 to vaporize the one or more vaporizable or non-vaporizable materials. For example, a user can depress a button, causing the vaporizer 108 to start vaporizing the one or more vaporizable or non-vaporizable materials. A user can then draw on an outlet 114 to inhale the vapor. In various aspects, the processor 102 can control vapor production and flow to the outlet 114 based on data detected by a flow sensor 116. For example, as a user draws on the outlet 114, the flow sensor 116 can detect the resultant pressure and provide a signal to the processor 102. In response, the processor 102 can cause the vaporizer 108 to begin vaporizing the one or more vaporizable or non-vaporizable materials, terminate vaporizing the one or more vaporizable or non-vaporizable materials, and/or otherwise adjust a rate of vaporization of the one or more vaporizable or non-vaporizable materials. In another aspect, the vapor can exit the vapor device 100 through an outlet 124. The outlet 124 differs from the outlet 114 in that the outlet 124 can be configured to distribute the vapor into the local atmosphere, rather than being inhaled by a user. In an aspect, vapor exiting the outlet 124 can be at least one of aromatic, medicinal, recreational, and/or wellness related. In an aspect, the vapor device 100 can comprise any number of outlets. In an aspect, the outlet 114 and/or the outlet 124 can comprise at least one flexible tube. For example, a lumen of the at least one flexible tube can be in fluid communication with one or more components (e.g., a first container) of the vapor device 100 to provide vapor to a user. In more detailed aspects, the at least one flexible tube may include at least two flexible tubes. Accordingly, the vapor device 100 may further include a second container configured to receive a second vaporizable material such that a first flexible tube can receive vapor from the first vaporizable material and a second flexible tube receive vapor from the second vaporizable material. For example, the at least two flexible tubes can be in fluid communication with the first container and with second container. The vapor device 100 may include an electrical or mechanical sensor configured to sense a pressure level, and therefore suction, in an interior of the flexible tube. Application of suction may activate the vapor device 100 and cause vapor to flow.

In another aspect, the vapor device 100 can comprise a piezoelectric dispersing element. In some aspects, the piezoelectric dispersing element can be charged by a battery, and can be driven by a processor on a circuit board. The circuit board can be produced using a polyimide such as Kapton, or other suitable material. The piezoelectric dispersing element can comprise a thin metal disc which causes dispersion of the fluid fed into the dispersing element via the wick or other soaked piece of organic material through vibration. Once in contact with the piezoelectric dispersing element, the vaporizable material (e.g., fluid) can be vaporized (e.g., turned into vapor or mist) and the vapor can be dispersed via a system pump and/or a sucking action of the user. In some aspects, the piezoelectric dispersing element can cause dispersion of the vaporizable material by producing ultrasonic vibrations. An electric field applied to a piezoelectric material within the piezoelectric element can cause ultrasonic expansion and contraction of the piezoelectric material, resulting in ultrasonic vibrations to the disc. The ultrasonic vibrations can cause the vaporizable material to disperse, thus forming a vapor or mist from the vaporizable material.

In some aspects, the connection between a power supply and the piezoelectric dispersing element can be facilitated using one or more conductive coils. The conductive coils can provide an ultrasonic power input to the piezoelectric dispersing element. For example, the signal carried by the coil can have a frequency of approximately 107.8 kHz. In some aspects, the piezoelectric dispersing element can comprise a piezoelectric dispersing element that can receive the ultrasonic signal transmitted from the power supply through the coils, and can cause vaporization of the vaporizable liquid by producing ultrasonic vibrations. An ultrasonic electric field applied to a piezoelectric material within the piezoelectric element causes ultrasonic expansion and contraction of the piezoelectric material, resulting in ultrasonic vibrations according to the frequency of the signal. The vaporizable liquid can be vibrated by the ultrasonic energy produced by the piezoelectric dispersing element, thus causing dispersal and/or atomization of the liquid. In an aspect, the vapor device 100 can be configured to permit a user to select between using a heating element of the vaporizer 108 or the piezoelectric dispersing element. In another aspect, the vapor device 100 can be configured to permit a user to utilize both a heating element of the vaporizer 108 and the piezoelectric dispersing element.

In an aspect, the vapor device 100 can comprise a heating casing 126. The heating casing 126 can enclose one or more of the container 110, the vaporizer 108, and/or the outlet 114. In a further aspect, the heating casing 126 can enclose one or more components that make up the container 110, the vaporizer 108, and/or the outlet 114. The heating casing 126 can be made of ceramic, metal, and/or porcelain. The heating casing 126 can have varying thickness. In an aspect, the heating casing 126 can be coupled to the power supply 120 to receive power to heat the heating casing 126. In another aspect, the heating casing 126 can be coupled to the vaporizer 108 to heat the heating casing 126. In another aspect, the heating casing 126 can serve an insulation role.

In an aspect, the vapor device 100 can comprise a filtration element 128. The filtration element 128 can be configured to remove (e.g., filter, purify, etc) contaminants from air entering the vapor device 100. The filtration element 128 can optionally comprise a fan 130 to assist in delivering air to the filtration element 128. The vapor device 100 can be configured to intake air into the filtration element 128, filter the air, and pass the filtered air to the vaporizer 108 for use in vaporizing the one or more vaporizable or non-vaporizable materials. In another aspect, the vapor device 100 can be configured to intake air into the filtration element 128, filter the air, and bypass the vaporizer 108 by passing the filtered air directly to the outlet 114 for inhalation by a user.

In an aspect, the filtration element 128 can comprise cotton, polymer, wool, satin, meta materials and the like. The filtration element 128 can comprise a filter material that at least one airborne particle and/or undesired gas by a mechanical mechanism, an electrical mechanism, and/or a chemical mechanism. The filter material can comprise one or more pieces of a filter fabric that can filter out one or more airborne particles and/or gasses. The filter fabric can be a woven and/or non-woven material. The filter fabric can be made from natural fibers (e.g., cotton, wool, etc.) and/or from synthetic fibers (e.g., polyester, nylon, polypropylene, etc.). The thickness of the filter fabric can be varied depending on the desired filter efficiencies and/or the region of the apparel where the filter fabric is to be used. The filter fabric can be designed to filter airborne particles and/or gasses by mechanical mechanisms (e.g., weave density), by electrical mechanisms (e.g., charged fibers, charged metals, etc.), and/or by chemical mechanisms (e.g., absorptive charcoal particles, adsorptive materials, etc.). In as aspect, the filter material can comprise electrically charged fibers such as, but not limited to, FILTRETE by 3M. In another aspect, the filter material can comprise a high density material similar to material used for medical masks which are used by medical personnel in doctors' offices, hospitals, and the like. In an aspect, the filter material can be treated with an anti-bacterial solution and/or otherwise made from anti-bacterial materials. In another aspect, the filtration element 128 can comprise electrostatic plates, ultraviolet light, a HEPA filter, combinations thereof, and the like.

In an aspect, the vapor device 100 can comprise a cooling element 132. The cooling element 132 can be configured to cool vapor exiting the vaporizer 108 prior to passing through the outlet 114. The cooling element 132 can cool vapor by utilizing air or space within the vapor device 100. The air used by the cooling element 132 can be either static (existing in the vapor device 100) or drawn into an intake and through the cooling element 132 and the vapor device 100. The intake can comprise various pumping, pressure, fan, or other intake systems for drawing air into the cooling element 132. In an aspect, the cooling element 132 can reside separately or can be integrated the vaporizer 108. The cooling element 132 can be a single cooled electronic element within a tube or space and/or the cooling element 132 can be configured as a series of coils or as a grid like structure. The materials for the cooling element 132 can be metal, liquid, polymer, natural substance, synthetic substance, air, or any combination thereof. The cooling element 132 can be powered by the power supply 120, by a separate battery (not shown), or other power source (not shown) including the use of excess heat energy created by the vaporizer 108 being converted to energy used for cooling by virtue of a small turbine or pressure system to convert the energy. Heat differentials between the vaporizer 108 and the cooling element 132 can also be converted to energy utilizing commonly known geothermal energy principles.

In an aspect, the vapor device 100 can comprise a magnetic element 134. For example, the magnetic element 134 can comprise an electromagnet, a ceramic magnet, a ferrite magnet, and/or the like. The magnetic element 134 can be configured to apply a magnetic field to air as it is brought into the vapor device 100, in the vaporizer 108, and/or as vapor exits the outlet 114.

The input/output device 112 can be used to select whether vapor exiting the outlet 114 should be cooled or not cooled and/or heated or not heated and/or magnetized or not magnetized. For example, a user can use the input/output device 112 to selectively cool vapor at times and not cool vapor at other times. The user can use the input/output device 112 to selectively heat vapor at times and not heat vapor at other times. The user can use the input/output device 112 to selectively magnetize vapor at times and not magnetize vapor at other times. The user can further use the input/output device 112 to select a desired smoothness, temperature, and/or range of temperatures. The user can adjust the temperature of the vapor by selecting or clicking on a clickable setting on a part of the vapor device 100. The user can use, for example, a graphical user interface (GUI) or a mechanical input enabled by virtue of clicking a rotational mechanism at either end of the vapor device 100.

In an aspect, cooling control can be set within the vapor device 100 settings via the processor 102 and system software (e.g., dynamic linked libraries). The memory 104 can store settings. Suggestions and remote settings can be communicated to and/or from the vapor device 100 via the input/output device 112 and/or the network access device 106. Cooling of the vapor can be set and calibrated between heating and cooling mechanisms to what is deemed an ideal temperature by the manufacturer of the vapor device 100 for the vaporizable material. For example, a temperature can be set such that resultant vapor delivers the coolest feeling to the average user but does not present any health risk to the user by virtue of the vapor being too cold, including the potential for rapid expansion of cooled vapor within the lungs and the damaging of tissue by vapor which has been cooled to a temperature which may cause frostbite like symptoms.

The robotic vapor device 101 can comprise a processor 138. The processor 138 can be, or can comprise, any suitable microprocessor or microcontroller, for example, a low-power application-specific controller (ASIC) and/or a field programmable gate array (FPGA) designed or programmed specifically for the task of controlling a device as described herein, or a general purpose central processing unit (CPU), for example, one based on 80×86 architecture as designed by Intel™ or AMD™, or a system-on-a-chip as designed by ARM™. The processor 138 can be coupled (e.g., communicatively, operatively, etc. . . . ) to auxiliary devices or modules of the robotic vapor device 101 using a bus or other coupling. The robotic vapor device 101 can comprise a power supply 140. The power supply 140 can comprise one or more batteries and/or other power storage device (e.g., capacitor) and/or a port for connecting to an external power supply. For example, an external power supply can supply power to the robotic vapor device 101 and a battery can store at least a portion of the supplied power. The one or more batteries can be rechargeable. The one or more batteries can comprise a lithium-ion battery (including thin film lithium ion batteries), a lithium ion polymer battery, a nickel-cadmium battery, a nickel metal hydride battery, a lead-acid battery, combinations thereof, and the like.

The robotic vapor device 101 can comprise a memory device 142 coupled to the processor 138. The memory device 142 can comprise a random access memory (RAM) configured for storing program instructions and data for execution or processing by the processor 138 during control of the robotic vapor device 101. When the robotic vapor device 101 is powered off or in an inactive state, program instructions and data can be stored in a long-term memory, for example, a non-volatile magnetic optical, or electronic memory storage device (not shown). Either or both of the RAM or the long-term memory can comprise a non-transitory computer-readable medium storing program instructions that, when executed by the processor 138, cause the robotic vapor device 101 to perform all or part of one or more methods and/or operations described herein. Program instructions can be written in any suitable high-level language, for example, C, C++, C# or the Java™, and compiled to produce machine-language code for execution by the processor 138.

In an aspect, the robotic vapor device 101 can comprise a network access device 144 allowing the robotic vapor device 101 to be coupled to one or more ancillary devices (not shown) such as via an access point (not shown) of a wireless telephone network, local area network, or other coupling to a wide area network, for example, the Internet. In that regard, the processor 138 can be configured to share data with the one or more ancillary devices via the network access device 144. The shared data can comprise, for example, usage data and/or operational data of the robotic vapor device 101, a status of the robotic vapor device 101, a status and/or operating condition of one or more the components of the robotic vapor device 101, text to be used in a message, a product order, payment information, and/or any other data. Similarly, the processor 138 can be configured to receive control instructions from the one or more ancillary devices via the network access device 144. For example, a configuration of the robotic vapor device 101, an operation of the robotic vapor device 101, and/or other settings of the robotic vapor device 101, can be controlled by the one or more ancillary devices via the network access device 144. For example, an ancillary device can comprise a server that can provide various services and another ancillary device can comprise a smartphone for controlling operation of the robotic vapor device 101. In some aspects, the smartphone or another ancillary device can be used as a primary input/output of the robotic vapor device 101 such that data is received by the robotic vapor device 101 from the server, transmitted to the smartphone, and output on a display of the smartphone. In an aspect, data transmitted to the ancillary device can comprise a mixture of vaporizable material and/or instructions to release vapor. For example, the robotic vapor device 101 can be configured to determine a need for the release of vapor into the atmosphere. The robotic vapor device 101 can provide instructions via the network access device 144 to an ancillary device (e.g., the vapor device 100) to release vapor into the atmosphere.

In an aspect, the robotic vapor device 101 can also comprise an input/output device 146 coupled to one or more of the processor 138, the network access device 106, and/or any other electronic component of the robotic vapor device 101. Input can be received from a user or another device and/or output can be provided to a user or another device via the input/output device 146. The input/output device 146 can comprise any combinations of input and/or output devices such as buttons, knobs, keyboards, touchscreens, displays, light-emitting elements, a speaker, and/or the like. In an aspect, the input/output device 146 can comprise an interface port (not shown) such as a wired interface, for example a serial port, a Universal Serial Bus (USB) port, an Ethernet port, or other suitable wired connection. The input/output device 146 can comprise a wireless interface (not shown), for example a transceiver using any suitable wireless protocol, for example WiFi (IEEE 802.11), Bluetooth®, infrared, or other wireless standard. For example, the input/output device 146 can communicate with a smartphone via Bluetooth® such that the inputs and outputs of the smartphone can be used by the user to interface with the robotic vapor device 101. In an aspect, the input/output device 146 can comprise a user interface. The user interface user interface can comprise at least one of lighted signal lights, gauges, boxes, forms, check marks, avatars, visual images, graphic designs, lists, active calibrations or calculations, 2D interactive fractal designs, 3D fractal designs, 2D and/or 3D representations of vapor devices and other interface system functions.

In an aspect, the input/output device 146 can be coupled to an adaptor device to receive power and/or send/receive data signals from an electronic device. For example, the input/output device 146 can be configured to receive power from the adaptor device and provide the power to the power supply 140 to recharge one or more batteries. The input/output device 146 can exchange data signals received from the adaptor device with the processor 138 to cause the processor to execute one or more functions.

In an aspect, the input/output device 146 can comprise a touchscreen interface and/or a biometric interface. For example, the input/output device 146 can include controls that allow the user to interact with and input information and commands to the robotic vapor device 101. For example, with respect to the embodiments described herein, the input/output device 146 can comprise a touch screen display. The input/output device 146 can be configured to provide the content of the exemplary screen shots shown herein, which are presented to the user via the functionality of a display. User inputs to the touch screen display are processed by, for example, the input/output device 146 and/or the processor 138. The input/output device 146 can also be configured to process new content and communications to the robotic vapor device 101. The touch screen display can provide controls and menu selections, and process commands and requests. Application and content objects can be provided by the touch screen display. The input/output device 146 and/or the processor 138 can receive and interpret commands and other inputs, interface with the other components of the robotic vapor device 101 as required. In an aspect, the touch screen display can enable a user to lock, unlock, or partially unlock or lock, the robotic vapor device 101. The robotic vapor device 101 can be transitioned from an idle and locked state into an open state by, for example, moving or dragging an icon on the screen of the robotic vapor device 101, entering in a password/passcode, and the like. The input/output device 146 can thus display information to a user such as a puff count, results of an analysis of vaporized material, battery remaining, signal strength, combinations thereof, and the like.

In an aspect, the input/output device 146 can comprise an audio user interface. A microphone can be configured to receive audio signals and relay the audio signals to the input/output device 146. The audio user interface can be any interface that is responsive to voice or other audio commands. The audio user interface can be configured to cause an action, activate a function, etc, by the robotic vapor device 101 (or another device) based on a received voice (or other audio) command. The audio user interface can be deployed directly on the robotic vapor device 101 and/or via other electronic devices (e.g., electronic communication devices such as a smartphone, a smart watch, a tablet, a laptop, a dedicated audio user interface device, and the like). The audio user interface can be used to control the functionality of the robotic vapor device 101.

The input/output device 146 can be configured to interface with other devices, for example, exercise equipment, computing equipment, communications devices and/or other vapor devices, for example, via a physical or wireless connection. The input/output device 146 can thus exchange data with the other equipment. A user may sync their robotic vapor device 101 to other devices, via programming attributes such as mutual dynamic link library (DLL) 'hooks'. This enables a smooth exchange of data between devices, as can a web interface between devices. The input/output device 146 can be used to upload one or more profiles to the other devices. Using exercise equipment as an example, the one or more profiles can comprise data such as workout routine data (e.g., timing, distance, settings, heart rate, etc. . . . ) and vaping data (e.g., eLiquid mixture recipes, supplements, vaping timing, etc. . . . ). Data from usage of previous exercise sessions can be archived and shared with new electronic vapor devices and/or new exercise equipment so that history and preferences may remain continuous and provide for simplified device settings, default settings, and recommended settings based upon the synthesis of current and archival data. The input/output device 146 can be configured to exchange data with the vapor device 100. For example, the robotic vapor device 101 can receive data related to a vaporization process being performed by the vapor device 100 (e.g., any data related to the vaporizer 108, a rate of vaporization, a temperature, a quantity of vaporizable material, an identification of vaporizable material or mixture thereof, usage of one or more of the cooling element 132, the magnetic element 134, and the heating casing 126, combinations thereof, and the like).

The robotic vapor device 101 can comprise an intake 148. The intake 148 can be receptacle for receiving at least a portion of the vapor device 100 or other vaporizer. In an aspect, the intake 148 can form an airtight seal with one or both of the outlet 114 and/or the outlet 124 of the vapor device 100. In another aspect, the intake 148 can form a non-airtight seal with one or both of the outlet 114 and/or the outlet 124 of the vapor device 100. The robotic vapor device 101 can comprise a pump 150 (or other similar mechanism) coupled to the intake 148. The pump can be configured to draw air/vapor from one or both of the outlet 114 and/or the outlet 124 of the vapor device 100, simulating an inhalation by a user of the vapor device 100.

The robotic vapor device 100 can be configured to test one or more functions of the vapor device 100. In another aspect, the robotic vapor device 100 can be configured to provide data and/or commands to the vapor device 100 to reconfigure operation of the vapor device 100 based on the testing of the one or more functions of the vapor device 100.

Air/vapor drawn in from the vapor device 100 by the pump 150 through the intake 148 can be passed to an analysis chamber 152. The analysis chamber 152 can be a receptacle within the robotic vapor device 101 configured for holding the air/vapor drawn from the vapor device 100 and for exposing the air/vapor to one or more sensors 136 in order to at least one of analyze, classify, compare, validate, refute, and/or catalogue the same. A result of the analysis can be, for example, a performance indicator for the vapor device 100 (any measure indicative of whether the vapor device 100 is performing as expected), an identification of at least one of medical, recreational, homeopathic, olfactory elements, spices, other cooking ingredients, ingredients analysis from food products, fuel analysis, pharmaceutical analysis, and the like. The robotic vapor device 101 can utilize, for example, mass spectrometry, gas chromatography, PH testing, particle and/or cellular testing, sensor based testing and other diagnostic and wellness testing either via locally available components or by transmitting data to a remote system for analysis. The mass spectrometry and/or gas chromatography systems disclosed herein can be implemented in a compact form factor, as is known in the art. Mass spectrometry is an analytical chemistry technique that identifies an amount and type of chemicals present in a sample by measuring the mass-to-charge ratio and abundance of gas-phase ions. A mass spectrum (plural spectra) is a plot of the ion signal as a function of the mass-to-charge ratio. The spectra are used to determine the elemental or isotopic signature of a sample, the masses of particles and of molecules, and to elucidate the chemical structures of molecules, such as peptides and other chemical compounds. Mass spectrometry works by ionizing chemical compounds to generate charged molecules or molecule fragments and measuring their mass-to-charge ratios.

In a typical mass spectrometry procedure, a sample of the air/vapor drawn from the vapor device 100, is ionized, for example by bombarding the air/vapor with electrons. This can cause some of the sample's molecules to break into charged fragments. These ions are then separated according to their mass-to-charge ratio, typically by accelerating them and subjecting them to an electric or magnetic field: ions of the same mass-to-charge ratio will undergo the same amount of deflection. The ions are detected by a mechanism capable of detecting charged particles, such as an electron multiplier. Results are displayed as spectra of the relative abundance of detected ions as a function of the mass-to-charge ratio. The atoms or molecules in the sample can be identified by correlating known masses to the identified masses stored on the memory device 142 or through a characteristic fragmentation pattern. Thus, a composition of the air/vapor drawn from the vapor device 100 can be determined.

In another aspect, nanosensor technology using nanostructures: single walled carbon nanotubes (SWNTs), combined with a silicon-based microfabrication and micromachining process can be used. This technology provides a sensor array that can accommodate different nanostructures for specific applications with the advantages of high sensitivity, low power consumption, compactness, high yield and low cost. This platform provides an array of sensing elements for chemical detection. Each sensor in the array can comprise a nanostructure—chosen from many different categories of sensing material—and an interdigitated electrode (IDE) as a transducer. It is one type of electrochemical sensor that implies the transfer of charge from one electrode to another. This means that at least two electrodes constitute an electrochemical cell to form a closed electrical circuit. Due to the interaction between nanotube devices and gas molecules, the electron configuration is changed in the nanostructured sensing device, therefore, the changes in the electronic signal such as current or voltage were observed before and during the exposure of gas species (such as NO 2, NH 3, etc.). By measuring the conductivity change of the CNT device, the concentration of the chemical species, such as gas molecules in the air/vapor drawn from the vapor device 100, can be measured.

In another aspect, the one or more sensors 136 can comprise one or more of, a biochemical/chemical sensor, a thermal sensor, a radiation sensor, a mechanical sensor, an optical sensor, a mechanical sensor, a magnetic sensor, an electrical sensor, combinations thereof and the like. The biochemical/chemical sensor can be configured to detect one or more biochemical/chemicals causing a negative environmental condition such as, but not limited to, smoke, a vapor, a gas, a liquid, a solid, an odor, combinations thereof, and/or the like. The biochemical/chemical sensor can comprise one or more of a mass spectrometer, a conducting/nonconducting regions sensor, a SAW sensor, a quartz microbalance sensor, a conductive composite sensor, a chemiresitor, a metal oxide gas sensor, an organic gas sensor, a MOSFET, a piezoelectric device, an infrared sensor, a sintered metal oxide sensor, a Pd-gate MOSFET, a metal FET structure, a electrochemical cell, a conducting polymer sensor, a catalytic gas sensor, an organic semiconducting gas sensor, a solid electrolyte gas sensors, a piezoelectric quartz crystal sensor, and/or combinations thereof.

The thermal sensor can be configured to detect temperature, heat, heat flow, entropy, heat capacity, combinations thereof, and the like. Exemplary thermal sensors include, but are not limited to, thermocouples, such as a semiconducting thermocouples, noise thermometry, thermoswitches, thermistors, metal thermoresistors, semiconducting thermoresistors, thermodiodes, thermotransistors, calorimeters, thermometers, indicators, and fiber optics.

The radiation sensor can be configured to detect gamma rays, X-rays, ultra-violet rays, visible, infrared, microwaves and radio waves. Exemplary radiation sensors include, but are not limited to, nuclear radiation microsensors, such as scintillation counters and solid state detectors, ultra-violet, visible and near infrared radiation microsensors, such as photoconductive cells, photodiodes, phototransistors, infrared radiation microsensors, such as photoconductive IR sensors and pyroelectric sensors.

The optical sensor can be configured to detect visible, near infrared, and infrared waves. The mechanical sensor can be configured to detect displacement, velocity, acceleration, force, torque, pressure, mass, flow, acoustic wavelength, and amplitude. Exemplary mechanical sensors include, but are not limited to, displacement microsensors, capacitive and inductive displacement sensors, optical displacement sensors, ultrasonic displacement sensors, pyroelectric, velocity and flow microsensors, transistor flow microsensors, acceleration microsensors, piezoresistive microaccelerometers, force, pressure and strain microsensors, and piezoelectric crystal sensors. The magnetic sensor can be configured to detect magnetic field, flux, magnetic moment, magnetization, and magnetic permeability. The electrical sensor can be configured to detect charge, current, voltage, resistance, conductance, capacitance, inductance, dielectric permittivity, polarization and frequency.

Upon sensing a condition of the air/vapor in the analysis chamber 152, the one or more sensors 122 can provide data to the processor 138 to determine the nature of the condition and to generate/transmit one or more notifications based on the condition. The one or more notifications can be deployed to the vapor device 100, to a user's wireless device, a remote computing device, and/or synced accounts. For example, the network device access device 144 can be used to transmit the one or more notifications directly (e.g., via Bluetooth®) to a user's smartphone to provide information to the user. In another aspect, the network access device 144 can be used to transmit sensed information and/or the one or more alerts to a remote server for use in syncing one or more other devices used by the user (e.g., other vapor devices, other electronic devices (smartphones, tablets, laptops, etc. . . . ). In another aspect, the one or more alerts can be provided to the user of the vapor device 100 via vibrations, audio, colors, and the like deployed from the mask, for example through the input/output device 146. The input/output device 112 can comprise one or more LED's of various colors to provide visual information to the user. In another example, the input/output device 146 can comprise one or more speakers that can provide audio information to the user. For example, various patterns of beeps, sounds, and/or voice recordings can be utilized to provide the audio information to the user. In another example, the input/output device 146 can comprise an LCD screen/touchscreen that provides a summary and/or detailed information regarding the condition and/or the one or more notifications.

In another aspect, upon sensing a condition, the one or more sensors 136 can provide data to the processor 138 to determine the nature of the condition and to provide a recommendation for mitigating the condition. Mitigating the conditions can comprise, for example, adjusting one or more operational parameters of the vapor device 100 (e.g., temperature of vaporization, quantity of one or more vaporizable materials vaporized, etc. . . . ). The processor 138 can access a database stored in the memory device 142 to make such a determination or the network device 144 can be used to request information from a server to verify the sensor findings. In an aspect, the server can provide an analysis service to the robotic vapor device 101. For example, the server can analyze data sent by the robotic vapor device 101 based on a reading from the one or more sensors 136. The server can determine and transmit one or more recommendations to the vapor device 100 to mitigate the sensed condition. The robotic vapor device 101 can use the one or more recommendations to transmit one or more commands to the vapor device 100 to reconfigure operation of the vapor device 100.

Figure 2:
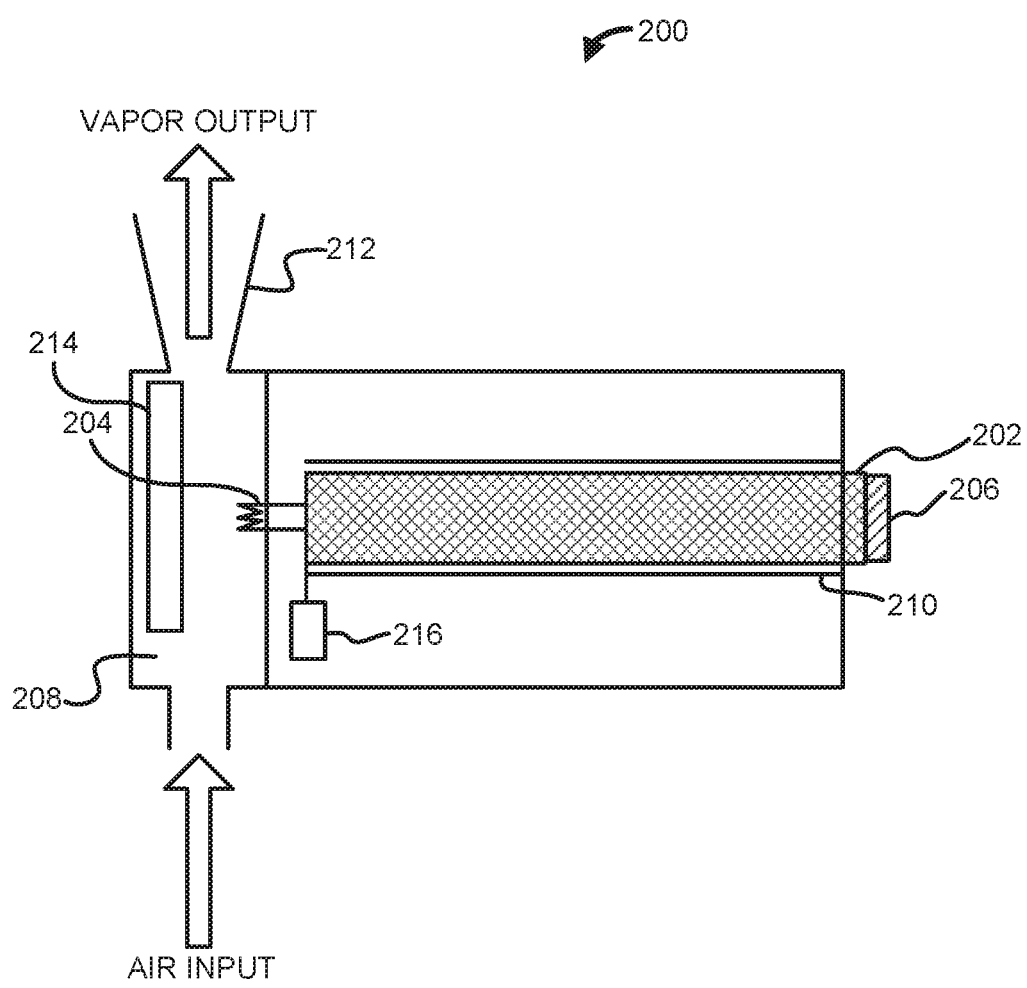
FIG. 2 illustrates an exemplary vaporizer.

FIG. 2 illustrates an exemplary vaporizer 200. The vaporizer 200 can be, for example, an e-cigarette, an e-cigar, an electronic vapor device, a hybrid electronic communication handset coupled/integrated vapor device, a robotic vapor device, a modified vapor device "mod," a micro-sized electronic vapor device, a robotic vapor device, and the like. The vaporizer 200 can be used internally of the vapor device 100 or can be a separate device. For example, the vaporizer 200 can be used in place of the vaporizer 108.

The vaporizer 200 can comprise or be coupled to one or more containers 202 containing a vaporizable material, for example a fluid. For example, coupling between the vaporizer 200 and the one or more containers 202 can be via a wick 204, via a valve, or by some other structure. Coupling can operate independently of gravity, such as by capillary action or pressure drop through a valve. The vaporizer 200 can be configured to vaporize the vaporizable material from the one or more containers 202 at controlled rates in response to mechanical input from a component of the vapor device 100, and/or in response to control signals from the processor 102 or another component. Vaporizable material (e.g., fluid) can be supplied by one or more replaceable cartridges 206. In an aspect the vaporizable material can comprise aromatic elements. In an aspect, the aromatic elements can be medicinal, recreational, and/or wellness related. The aromatic element can include, but is not limited to, at least one of lavender or other floral aromatic eLiquids, mint, menthol, herbal soil or geologic, plant based, name brand perfumes, custom mixed perfume formulated inside the vapor device 100 and aromas constructed to replicate the smell of different geographic places, conditions, and/or occurrences. For example, the smell of places may include specific or general sports venues, well known travel destinations, the mix of one's own personal space or home. The smell of conditions may include, for example, the smell of a pet, a baby, a season, a general environment (e.g., a forest), a new car, a sexual nature (e.g., musk, pheromones, etc. . . . ). The one or more replaceable cartridges 206 can contain the vaporizable material. If the vaporizable material is liquid, the cartridge can comprise the wick 204 to aid in transporting the liquid to a mixing chamber 208. In the alternative, some other transport mode can be used. Each of the one or more replaceable cartridges 206 can be configured to fit inside and engage removably with a receptacle (such as the container 202 and/or a secondary container) of the vapor device 100. In an alternative, or in addition, one or more fluid containers 210 can be fixed in the vapor device 100 and configured to be refillable. In an aspect, one or more materials can be vaporized at a single time by the vaporizer 200. For example, some material can be vaporized and drawn through an exhaust port 212 and/or some material can be vaporized and exhausted via a smoke simulator outlet (not shown).

The mixing chamber 208 can also receive an amount of one or more compounds (e.g., vaporizable material) to be vaporized. For example, the processor 102 can determine a first amount of a first compound and determine a second amount of a second compound. The processor 102 can cause the withdrawal of the first amount of the first compound from a first container into the mixing chamber and the second amount of the second compound from a second container into the mixing chamber. The processor 102 can also determine a target dose of the first compound, determine a vaporization ratio of the first compound and the second compound based on the target dose, determine the first amount of the first compound based on the vaporization ratio, determine the second amount of the second compound based on the vaporization ratio, and cause the withdrawal of the first amount of the first compound into the mixing chamber, and the withdrawal of the second amount of the second compound into the mixing chamber.

The processor 102 can also determine a target dose of the first compound, determine a vaporization ratio of the first compound and the second compound based on the target dose, determine the first amount of the first compound based on the vaporization ratio, and determine the second amount of the second compound based on the vaporization ratio. After expelling the vapor through an exhaust port for inhalation by a user, the processor 102 can determine that a cumulative dose is approaching the target dose and reduce the vaporization ratio. In an aspect, one or more of the vaporization ratio, the target dose, and/or the cumulative dose can be determined remotely and transmitted to the vapor device 100 for use.

In operation, a heating element 214 can vaporize or nebulize the vaporizable material in the mixing chamber 208, producing an inhalable vapor/mist that can be expelled via the exhaust port 212. In an aspect, the heating element 214 can comprise a heater coupled to the wick (or a heated wick) 204 operatively coupled to (for example, in fluid communication with) the mixing chamber 210. The heating element 214 can comprise a nickel-chromium wire or the like, with a temperature sensor (not shown) such as a thermistor or thermocouple. Within definable limits, by controlling power to the wick 204, a rate of vaporization can be independently controlled. A multiplexer 216 can receive power from any suitable source and exchange data signals with a processor, for example, the processor 102 of the vapor device 100, for control of the vaporizer 200. At a minimum, control can be provided between no power (off state) and one or more powered states. Other control mechanisms can also be suitable.

In another aspect, the vaporizer 200 can comprise a piezoelectric dispersing element. In some aspects, the piezoelectric dispersing element can be charged by a battery, and can be driven by a processor on a circuit board. The circuit board can be produced using a polyimide such as Kapton, or other suitable material. The piezoelectric dispersing element can comprise a thin metal disc which causes dispersion of the fluid fed into the dispersing element via the wick or other soaked piece of organic material through vibration. Once in contact with the piezoelectric dispersing element, the vaporizable material (e.g., fluid) can be vaporized (e.g., turned into vapor or mist) and the vapor can be dispersed via a system pump and/or a sucking action of the user. In some aspects, the piezoelectric dispersing element can cause dispersion of the vaporizable material by producing ultrasonic vibrations. An electric field applied to a piezoelectric material within the piezoelectric element can cause ultrasonic expansion and contraction of the piezoelectric material, resulting in ultrasonic vibrations to the disc. The ultrasonic vibrations can cause the vaporizable material to disperse, thus forming a vapor or mist from the vaporizable material.

In an aspect, the vaporizer 200 can be configured to permit a user to select between using the heating element 214 or the piezoelectric dispersing element. In another aspect, the vaporizer 200 can be configured to permit a user to utilize both the heating element 214 and the piezoelectric dispersing element.

In some aspects, the connection between a power supply and the piezoelectric dispersing element can be facilitated using one or more conductive coils. The conductive coils can provide an ultrasonic power input to the piezoelectric dispersing element. For example, the signal carried by the coil can have a frequency of approximately 107.8 kHz. In some aspects, the piezoelectric dispersing element can comprise a piezoelectric dispersing element that can receive the ultrasonic signal transmitted from the power supply through the coils, and can cause vaporization of the vaporizable liquid by producing ultrasonic vibrations. An ultrasonic electric field applied to a piezoelectric material within the piezoelectric element causes ultrasonic expansion and contraction of the piezoelectric material, resulting in ultrasonic vibrations according to the frequency of the signal. The vaporizable liquid can be vibrated by the ultrasonic energy produced by the piezoelectric dispersing element, thus causing dispersal and/or atomization of the liquid.

Figure 3:
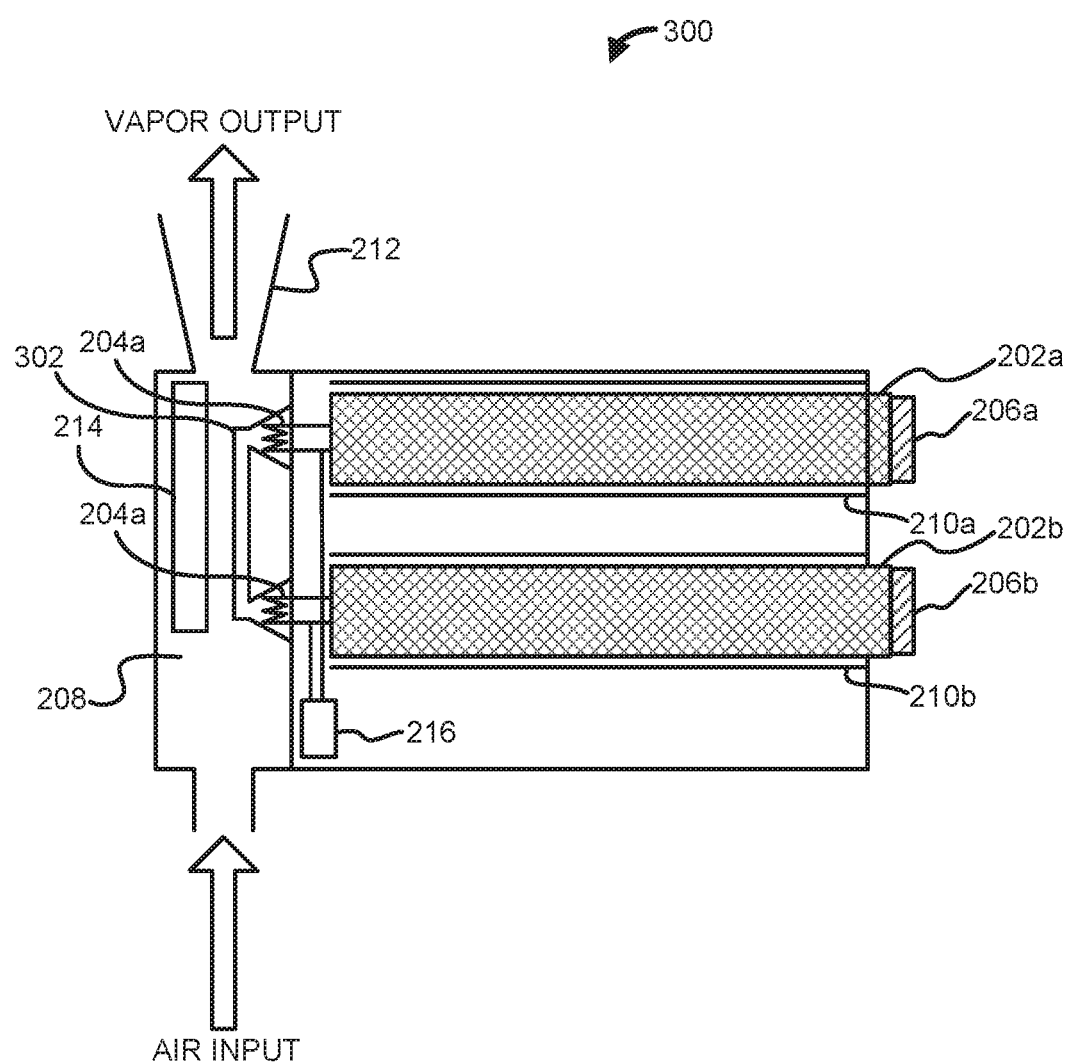
FIG. 3 illustrates an exemplary vaporizer configured for vaporizing a mixture of vaporizable material.

FIG. 3 illustrates a vaporizer 300 that comprises the elements of the vaporizer 200 with two containers 202a and 202b containing a vaporizable material, for example a fluid or a solid. In an aspect, the fluid can be the same fluid in both containers or the fluid can be different in each container. In an aspect the fluid can comprise aromatic elements. The aromatic element can include, but is not limited to, at least one of lavender or other floral aromatic eLiquids, mint, menthol, herbal soil or geologic, plant based, name brand perfumes, custom mixed perfume formulated inside the vapor device 100 and aromas constructed to replicate the smell of different geographic places, conditions, and/or occurrences. For example, the smell of places may include specific or general sports venues, well known travel destinations, the mix of one's own personal space or home. The smell of conditions may include, for example, the smell of a pet, a baby, a season, a general environment (e.g., a forest), a new car, a sexual nature (e.g., musk, pheromones, etc. . . . ). Coupling between the vaporizer 200 and the container 202a and the container 202b can be via a wick 204a and a wick 204b, respectively, via a valve, or by some other structure. Coupling can operate independently of gravity, such as by capillary action or pressure drop through a valve. The vaporizer 300 can be configured to mix in varying proportions the fluids contained in the container 202a and the container 202b and vaporize the mixture at controlled rates in response to mechanical input from a component of the vapor device 100, and/or in response to control signals from the processor 102 or another component. For example, based on a vaporization ratio. In an aspect, a mixing element 302 can be coupled to the container 202a and the container 202b. The mixing element can, in response to a control signal from the processor 102, withdraw select quantities of vaporizable material in order to create a customized mixture of different types of vaporizable material. Vaporizable material (e.g., fluid) can be supplied by one or more replaceable cartridges 206a and 206b. The one or more replaceable cartridges 206a and 206b can contain a vaporizable material. If the vaporizable material is liquid, the cartridge can comprise the wick 204a or 204b to aid in transporting the liquid to a mixing chamber 208. In the alternative, some other transport mode can be used. Each of the one or more replaceable cartridges 206a and 206b can be configured to fit inside and engage removably with a receptacle (such as the container 202a or the container 202b and/or a secondary container) of the vapor device 100. In an alternative, or in addition, one or more fluid containers 210a and 210b can be fixed in the vapor device 100 and configured to be refillable. In an aspect, one or more materials can be vaporized at a single time by the vaporizer 300. For example, some material can be vaporized and drawn through an exhaust port 212 and/or some material can be vaporized and exhausted via a smoke simulator outlet (not shown).

Figure 4:
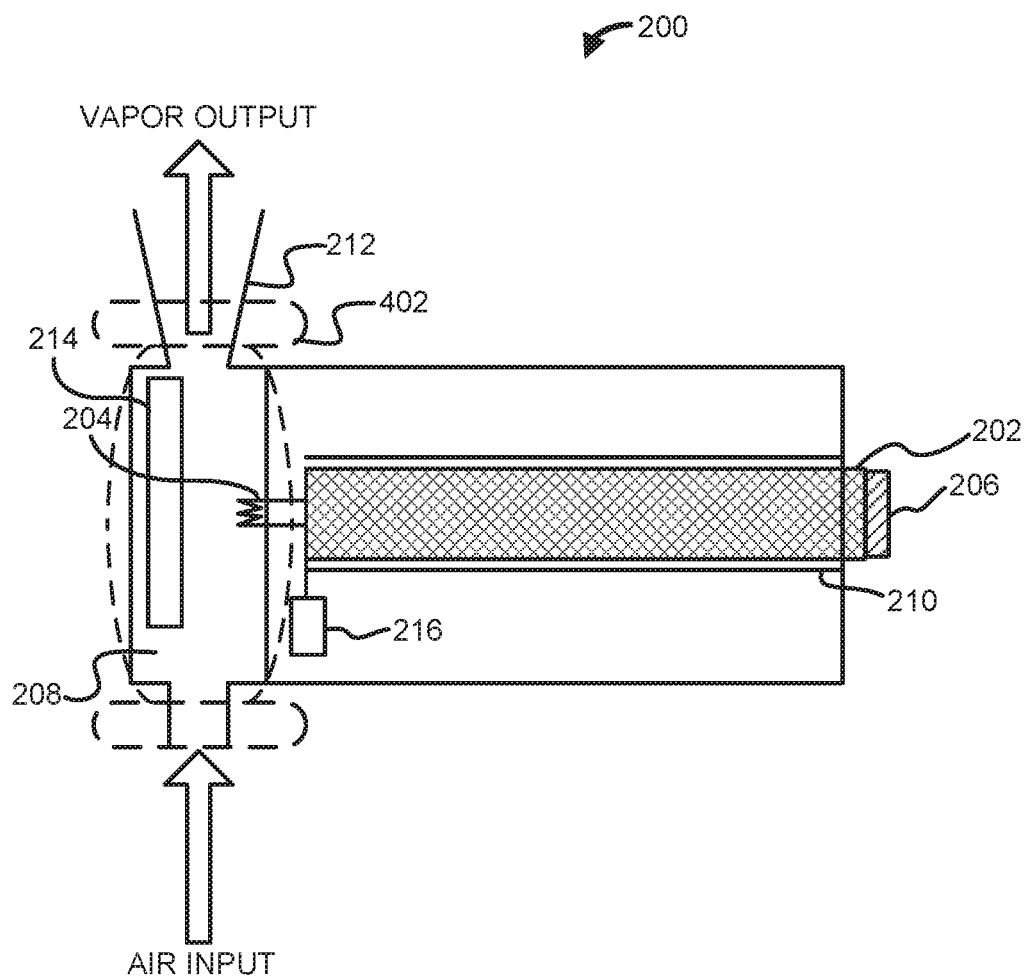
FIG. 4 illustrates an exemplary vaporizer device.

FIG. 4 illustrates a vaporizer 200 that comprises the elements of the vaporizer 200 with a heating casing 402. The heating casing 402 can enclose the heating element 214 or can be adjacent to the heating element 214. The heating casing 402 is illustrated with dashed lines, indicating components contained therein. The heating casing 402 can be made of ceramic, metal, and/or porcelain. The heating casing 402 can have varying thickness. In an aspect, the heating casing 402 can be coupled to the multiplexer 216 to receive power to heat the heating casing 402. In another aspect, the heating casing 402 can be coupled to the heating element 214 to heat the heating casing 402. In another aspect, the heating casing 402 can serve an insulation role.

Figure 5:
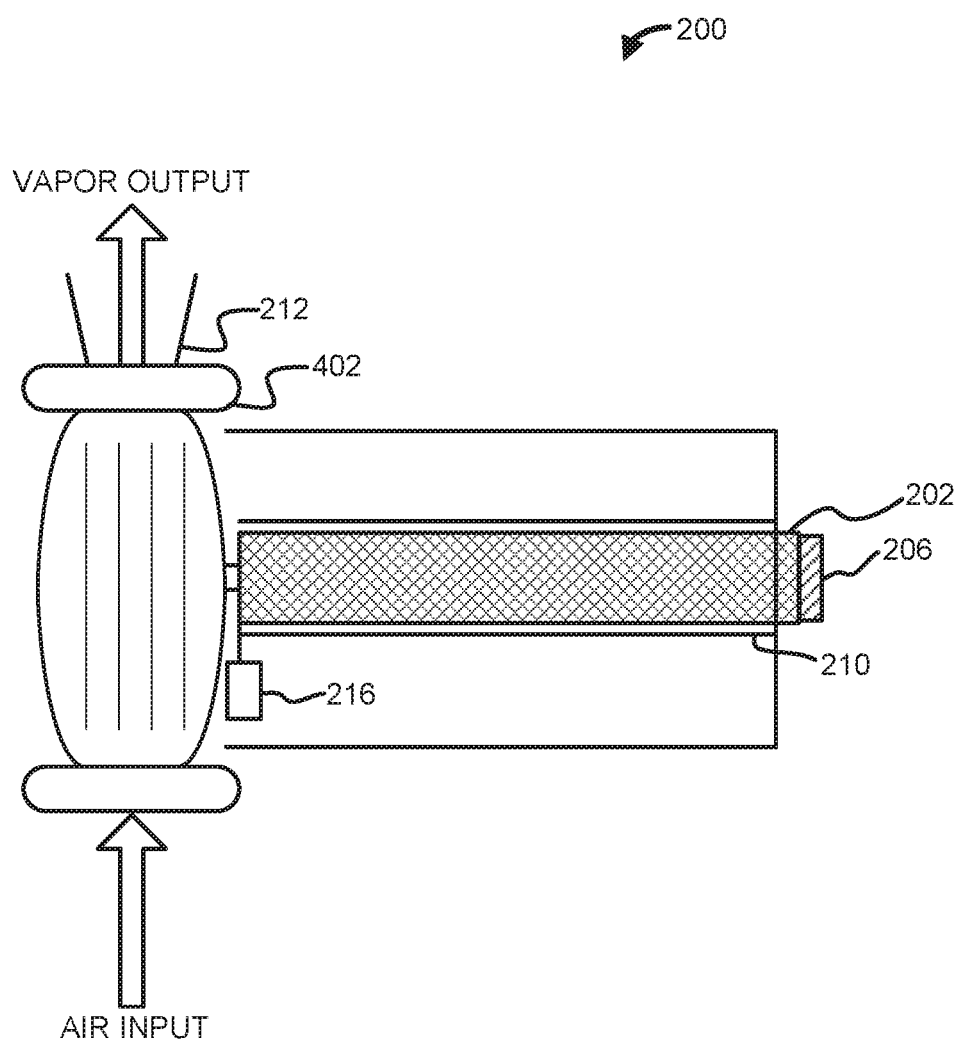
FIG. 5 illustrates another exemplary vaporizer.

FIG. 5 illustrates the vaporizer 200 of FIG. 2 and FIG. 4, but illustrates the heating casing 402 with solid lines, indicating components contained therein. Other placements of the heating casing 402 are contemplated. For example, the heating casing 402 can be placed after the heating element 214 and/or the mixing chamber 208.

Figure 6:
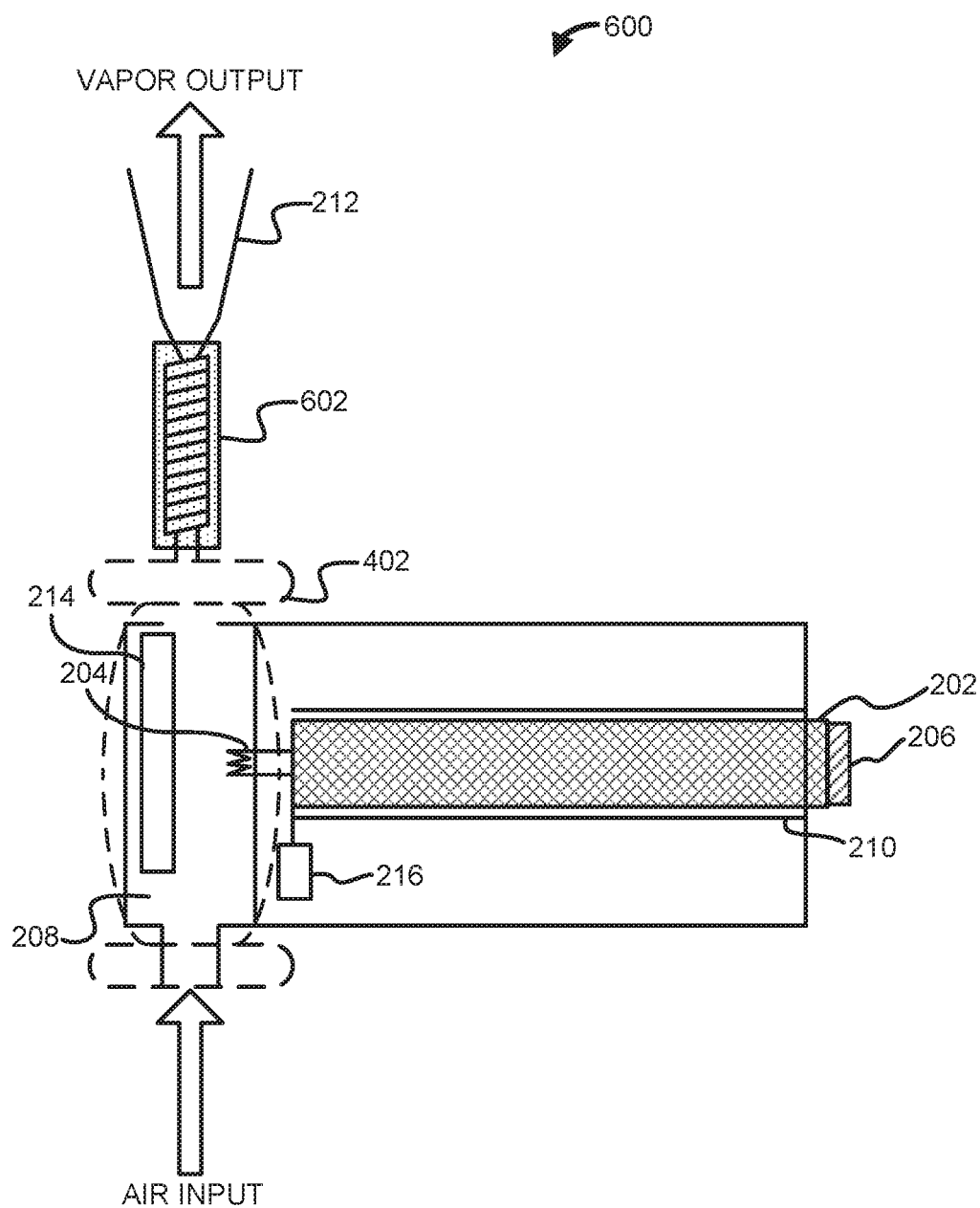
FIG. 6 illustrates another exemplary vaporizer.

FIG. 6 illustrates a vaporizer 600 that comprises the elements of the vaporizer 200 of FIG. 2 and FIG. 4, with the addition of a cooling element 602. The vaporizer 600 can optionally comprise the heating casing 402. The cooling element 602 can comprise one or more of a powered cooling element, a cooling air system, and/or or a cooling fluid system. The cooling element 602 can be self-powered, co-powered, or directly powered by a battery and/or charging system within the vapor device 100 (e.g., the power supply 120). In an aspect, the cooling element 602 can comprise an electrically connected conductive coil, grating, and/or other design to efficiently distribute cooling to the at least one of the vaporized and/or non-vaporized air. For example, the cooling element 602 can be configured to cool air as it is brought into the vaporizer 600/mixing chamber 208 and/or to cool vapor after it exits the mixing chamber 208. The cooling element 602 can be deployed such that the cooling element 602 is surrounded by the heated casing 402 and/or the heating element 214. In another aspect, the heated casing 402 and/or the heating element 214 can be surrounded by the cooling element 602. The cooling element 602 can utilize at least one of cooled air, cooled liquid, and/or cooled matter.

In an aspect, the cooling element 602 can be a coil of any suitable length and can reside proximate to the inhalation point of the vapor (e.g., the exhaust port 212). The temperature of the air is reduced as it travels through the cooling element 602. In an aspect, the cooling element 602 can comprise any structure that accomplishes a cooling effect. For example, the cooling element 602 can be replaced with a screen with a mesh or grid-like structure, a conical structure, and/or a series of cooling airlocks, either stationary or opening, in a periscopic/telescopic manner. The cooling element 602 can be any shape and/or can take multiple forms capable of cooling heated air, which passes through its space.

In an aspect, the cooling element 602 can be any suitable cooling system for use in a vapor device. For example, a fan, a heat sink, a liquid cooling system, a chemical cooling system, combinations thereof, and the like. In an aspect, the cooling element 602 can comprise a liquid cooling system whereby a fluid (e.g., water) passes through pipes in the vaporizer 600. As this fluid passes around the cooling element 602, the fluid absorbs heat, cooling air in the cooling element 602. After the fluid absorbs the heat, the fluid can pass through a heat exchanger which transfers the heat from the fluid to air blowing through the heat exchanger. By way of further example, the cooling element 602 can comprise a chemical cooling system that utilizes an endothermic reaction. An example of an endothermic reaction is dissolving ammonium nitrate in water. Such endothermic process is used in instant cold packs. These cold packs have a strong outer plastic layer that holds a bag of water and a chemical, or mixture of chemicals, that result in an endothermic reaction when dissolved in water. When the cold pack is squeezed, the inner bag of water breaks and the water mixes with the chemicals. The cold pack starts to cool as soon as the inner bag is broken, and stays cold for over an hour. Many instant cold packs contain ammonium nitrate. When ammonium nitrate is dissolved in water, it splits into positive ammonium ions and negative nitrate ions. In the process of dissolving, the water molecules contribute energy, and as a result, the water cools down. Thus, the vaporizer 600 can comprise a chamber for receiving the cooling element 602 in the form of a "cold pack." The cold pack can be activated prior to insertion into the vaporizer 600 or can be activated after insertion through use of a button/switch and the like to mechanically activate the cold pack inside the vaporizer 400.

In an aspect, the cooling element 602 can be selectively moved within the vaporizer 600 to control the temperature of the air mixing with vapor. For example, the cooling element 602 can be moved closer to the exhaust port 212 or further from the exhaust port 212 to regulate temperature. In another aspect, insulation can be incorporated as needed to maintain the integrity of heating and cooling, as well as absorbing any unwanted condensation due to internal or external conditions, or a combination thereof. The insulation can also be selectively moved within the vaporizer 600 to control the temperature of the air mixing with vapor. For example, the insulation can be moved to cover a portion, none, or all of the cooling element 602 to regulate temperature.

Figure 7:
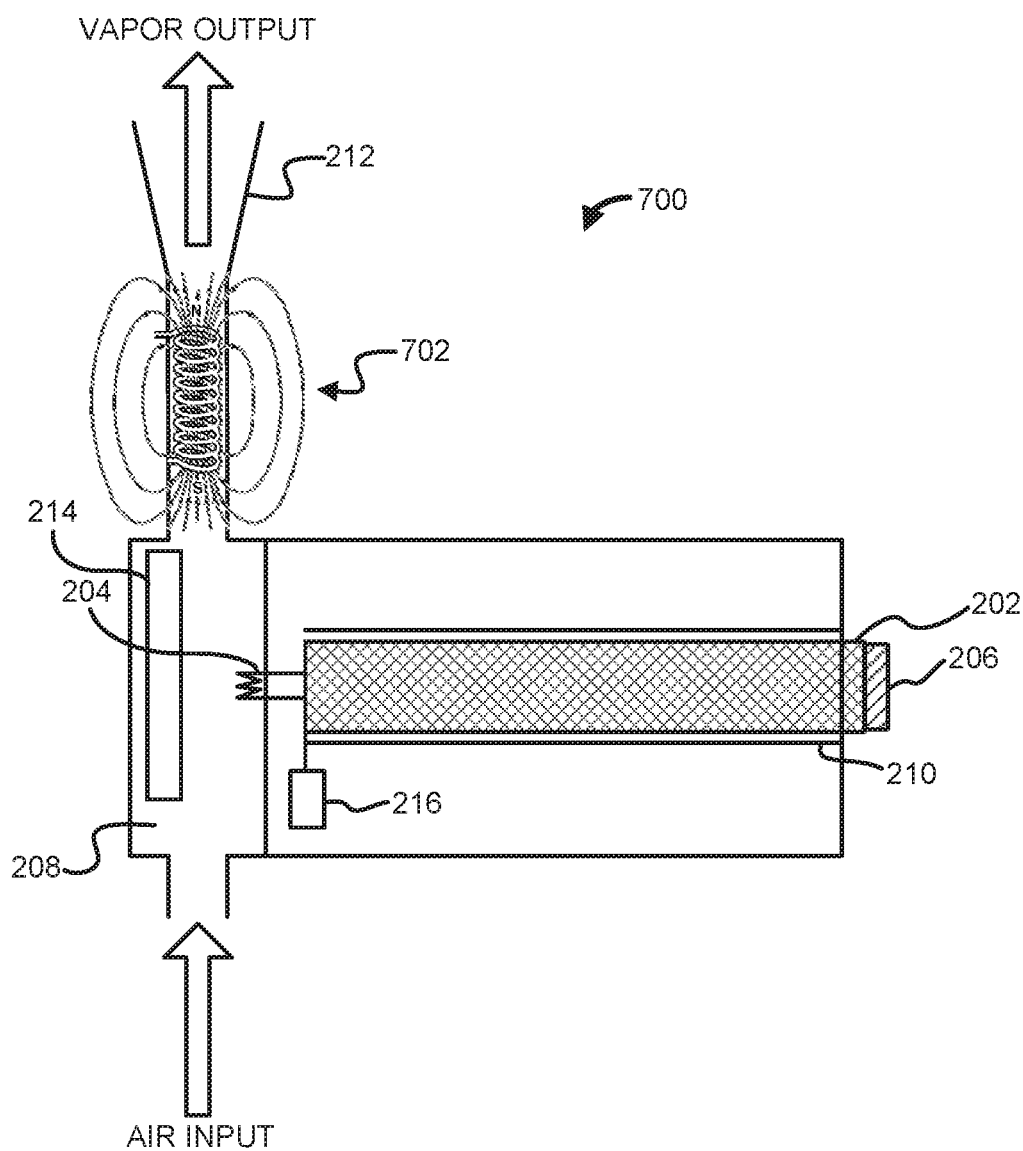
FIG. 7 illustrates another exemplary vaporizer.

FIG. 7 illustrates a vaporizer 700 that comprises elements in common with the vaporizer 200. The vaporizer 700 can optionally comprise the heating casing 402 (not shown) and/or the cooling element 602 (not shown). The vaporizer 700 can comprise a magnetic element 702. The magnetic element 702 can apply a magnetic field to vapor after exiting the mixing chamber 208. The magnetic field can cause positively and negatively charged particles in the vapor to curve in opposite directions, according to the Lorentz force law with two particles of opposite charge. The magnetic field can be created by at least one of an electric current generating a charge or a pre-charged magnetic material deployed within the vapor device 100. In an aspect, the magnetic element 702 can be built into the mixing chamber 208, the cooling element 602, the heating casing 402, or can be a separate magnetic element 702.

Figure 8:
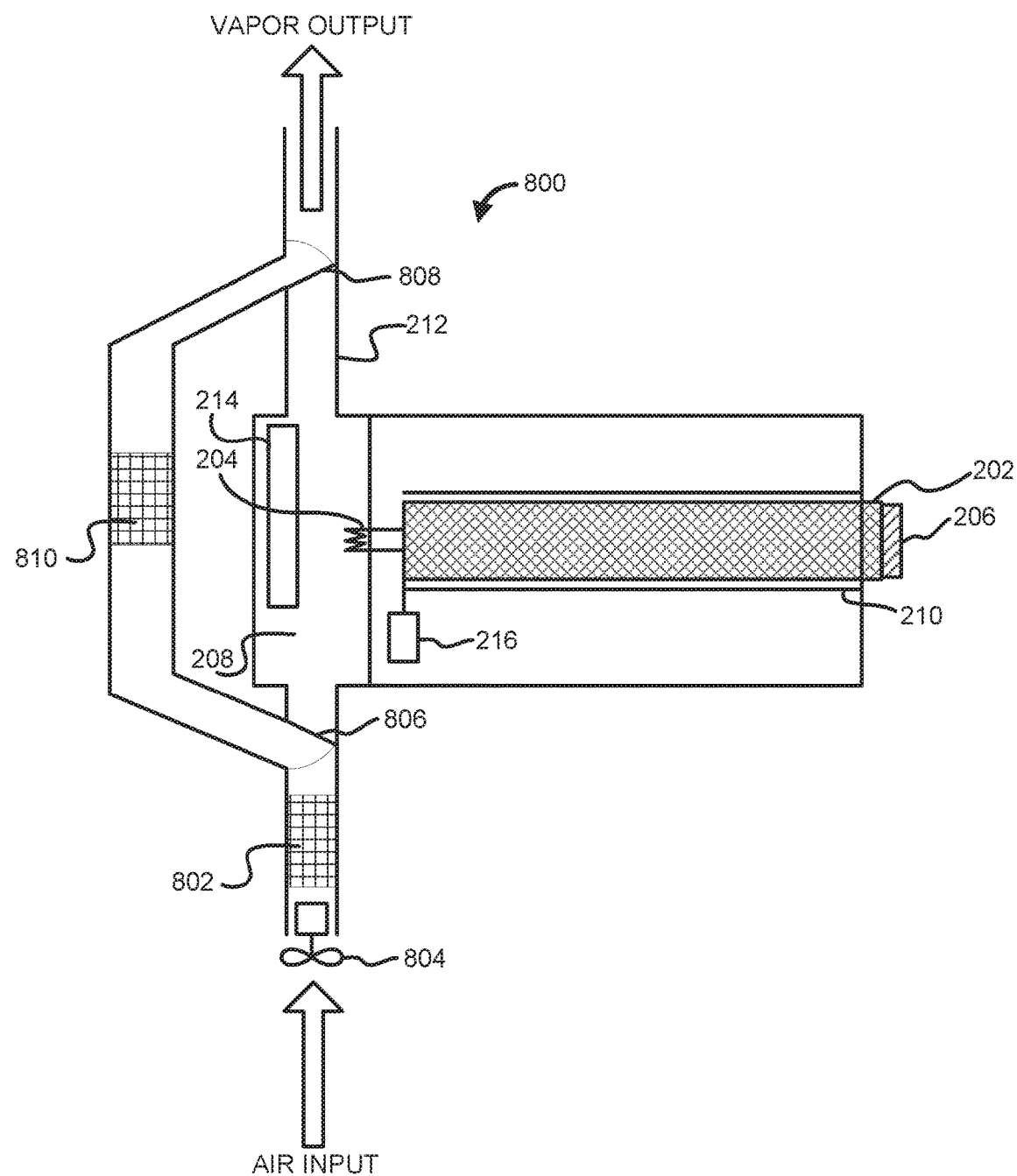
FIG. 8 illustrates an exemplary vaporizer configured for filtering air.

FIG. 8 illustrates a vaporizer 800 that comprises elements in common with the vaporizer 200. In an aspect, the vaporizer 800 can comprise a filtration element 802. The filtration element 802 can be configured to remove (e.g., filter, purify, etc) contaminants from air entering the vaporizer 800. The filtration element 802 can optionally comprise a fan 804 to assist in delivering air to the filtration element 802. The vaporizer 800 can be configured to intake air into the filtration element 802, filter the air, and pass the filtered air to the mixing chamber 208 for use in vaporizing the one or more vaporizable or non-vaporizable materials. In another aspect, the vaporizer 800 can be configured to intake air into the filtration element 802, filter the air, and bypass the mixing chamber 208 by engaging a door 806 and a door 808 to pass the filtered air directly to the exhaust port 212 for inhalation by a user. In an aspect, filtered air that bypasses the mixing chamber 208 by engaging the door 806 and the door 808 can pass through a second filtration element 810 to further remove (e.g., filter, purify, etc) contaminants from air entering the vaporizer 800. In an aspect, the vaporizer 800 can be configured to deploy and/or mix a proper/safe amount of oxygen which can be delivered either via the one or more replaceable cartridges 206 or via air pumped into a mask from external air and filtered through the filtration element 802 and/or the filtration element 810.

In an aspect, the filtration element 802 and/or the filtration element 810 can comprise cotton, polymer, wool, satin, meta materials and the like. The filtration element 802 and/or the filtration element 810 can comprise a filter material that at least one airborne particle and/or undesired gas by a mechanical mechanism, an electrical mechanism, and/or a chemical mechanism. The filter material can comprise one or more pieces of, a filter fabric that can filter out one or more airborne particles and/or gasses. The filter fabric can be a woven and/or non-woven material. The filter fabric can be made from natural fibers (e.g., cotton, wool, etc.) and/or from synthetic fibers (e.g., polyester, nylon, polypropylene, etc.). The thickness of the filter fabric can be varied depending on the desired filter efficiencies and/or the region of the apparel where the filter fabric is to be used. The filter fabric can be designed to filter airborne particles and/or gasses by mechanical mechanisms (e.g., weave density), by electrical mechanisms (e.g., charged fibers, charged metals, etc.), and/or by chemical mechanisms (e.g., absorptive charcoal particles, adsorptive materials, etc.). In as aspect, the filter material can comprise electrically charged fibers such as, but not limited to, FILTRETE by 3M. In another aspect, the filter material can comprise a high density material similar to material used for medical masks which are used by medical personnel in doctors' offices, hospitals, and the like. In an aspect, the filter material can be treated with an anti-bacterial solution and/or otherwise made from anti-bacterial materials. In another aspect, the filtration element 802 and/or the filtration element 810 can comprise electrostatic plates, ultraviolet light, a HEPA filter, combinations thereof, and the like.

Figure 9:
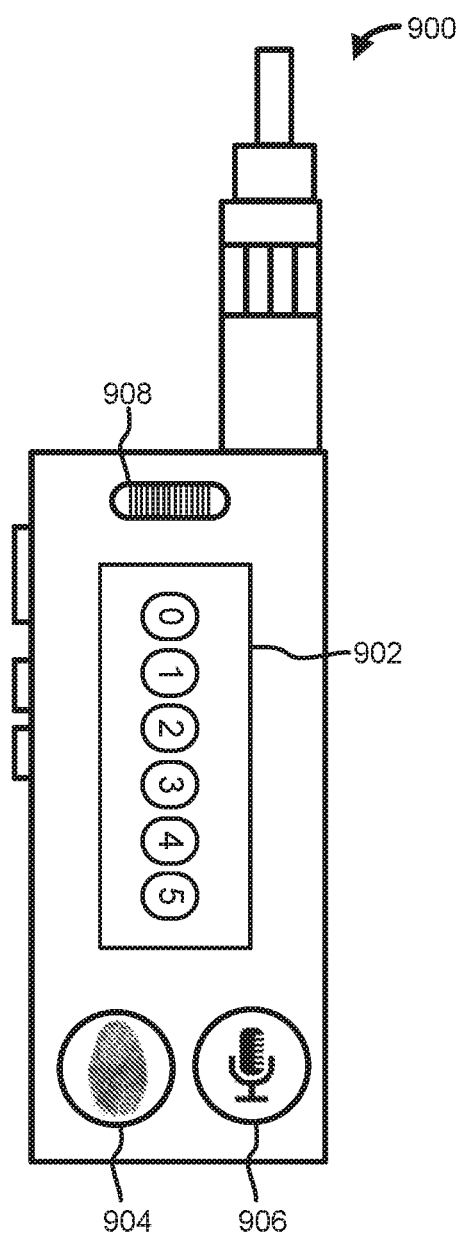
FIG. 9 illustrates an interface of an exemplary electronic vapor device.

FIG. 9 illustrates an exemplary vapor device 900. The exemplary vapor device 900 can comprise the vapor device 100 and/or any of the vaporizers disclosed herein. The exemplary vapor device 900 illustrates a display 902. The display 902 can be a touchscreen. The display 902 can be configured to enable a user to control any and/or all functionality of the exemplary vapor device 900. For example, a user can utilize the display 902 to enter a pass code to lock and/or unlock the exemplary vapor device 900. The exemplary vapor device 900 can comprise a biometric interface 904. For example, the biometric interface 904 can comprise a fingerprint scanner, an eye scanner, a facial scanner, and the like. The biometric interface 904 can be configured to enable a user to control any and/or all functionality of the exemplary vapor device 900. The exemplary vapor device 900 can comprise an audio interface 906. The audio interface 906 can comprise a button that, when engaged, enables a microphone 908. The microphone 908 can receive audio signals and provide the audio signals to a processor for interpretation into one or more commands to control one or more functions of the exemplary vapor device 900. The exemplary vapor device 900 can be coupled to the robotic vapor device 101 for testing and reconfiguration.

In an aspect, the exemplary vapor device 900 can be a standardized vapor device. As a standardized vapor device the exemplary vapor device 900 has been determined to be operating per manufacturer standards, user standards, or other third party standards. As such, the exemplary vapor device 900 can be coupled to the robotic vapor device 101 to assist in ensuring the robotic vapor device 101 is properly calibrated.

Figure 10:
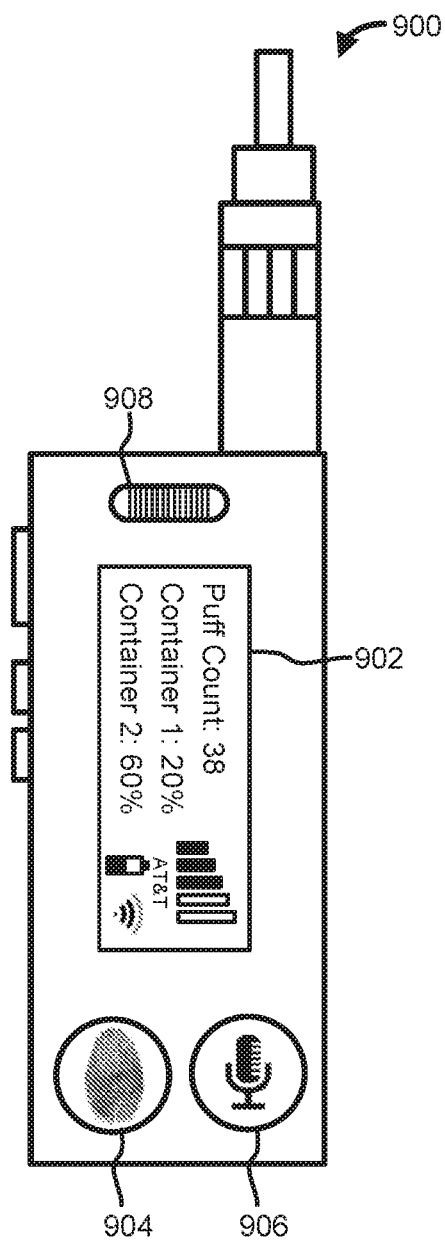
FIG. 10 illustrates another interface of an exemplary electronic vapor device.

FIG. 10 illustrates exemplary information that can be provided to a user via the display 902 of the exemplary vapor device 900. The display 902 can provide information to a user such as a puff count, an amount of vaporizable material remaining in one or more containers, battery remaining, signal strength, combinations thereof, and the like.

Figure 11:
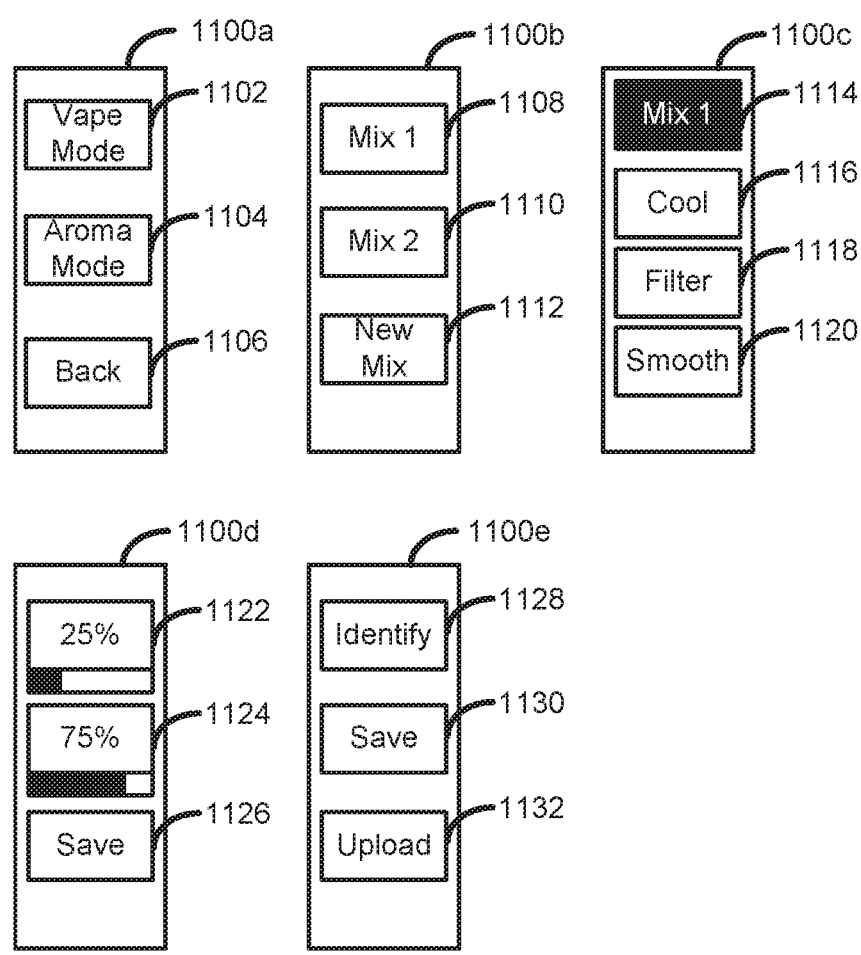
FIG. 11 illustrates several interfaces of an exemplary electronic vapor device.

FIG. 11 illustrates a series of user interfaces that can be provided via the display 902 of the exemplary vapor device 900. In an aspect, the exemplary vapor device 900 can be configured for multi-mode vapor usage. As a standardized vapor device, the multi-mode vapor usage can be used as part of a calibration protocol for the robotic vapor device 101. For example, the exemplary vapor device 900 can be configured to enable a user to inhale vapor (vape mode) or to release vapor into the atmosphere (aroma mode). User interface 1100a provides a user with interface elements to select which mode the user wishes to engage, a Vape Mode 1102, an Aroma Mode 1104, or an option to go back 1106 and return to the previous screen. The interface element Vape Mode 1102 enables a user to engage a vaporizer to generate a vapor for inhalation. The interface element Aroma Mode 1104 enables a user to engage the vaporizer to generate a vapor for release into the atmosphere.

In the event a user selects the Vape Mode 1102, the exemplary vapor device 900 will be configured to vaporize material and provide the resulting vapor to the user for inhalation. The user can be presented with user interface 1100b which provides the user an option to select interface elements that will determine which vaporizable material to vaporize. For example, an option of Mix 1 1108, Mix 2 1110, or a New Mix 1112. The interface element Mix 1 1108 enables a user to engage one or more containers that contain vaporizable material in a predefined amount and/or ratio. In an aspect, a selection of Mix 1 1108 can result in the exemplary vapor device 900 engaging a single container containing a single type of vaporizable material or engaging a plurality of containers containing a different types of vaporizable material in varying amounts. The interface element Mix 2 1110 enables a user to engage one or more containers that contain vaporizable material in a predefined amount and/or ratio. In an aspect, a selection of Mix 2 1110 can result in the exemplary vapor device 900 engaging a single container containing a single type of vaporizable material or engaging a plurality of containers containing a different types of vaporizable material in varying amounts. In an aspect, a selection of New Mix 1112 can result in the exemplary vapor device 900 receiving a new mixture, formula, recipe, etc. . . . of vaporizable materials and/or engage one or more containers that contain vaporizable material in the new mixture.

Upon selecting, for example, the Mix 1 1108, the user can be presented with user interface 1100c. User interface 1100c indicates to the user that Mix 1 has been selected via an indicator 1114. The user can be presented with options that control how the user wishes to experience the selected vapor. The user can be presented with interface elements Cool 1116, Filter 1118, and Smooth 1120. The interface element Cool 1116 enables a user to engage one or more cooling elements to reduce the temperature of the vapor. The interface element Filter 1118 enables a user to engage one or more filter elements to filter the air used in the vaporization process. The interface element Smooth 1120 enables a user to engage one or more heating casings, cooling elements, filter elements, and/or magnetic elements to provide the user with a smoother vaping experience.

Upon selecting New Mix 1112, the user can be presented with user interface 1100d. User interface 1100d provides the user with a container one ratio interface element 1122, a container two ratio interface element 1124, and Save 1126. The container one ratio interface element 1122 and the container two ratio interface element 1124 provide a user the ability to select an amount of each type of vaporizable material contained in container one and/or container two to utilize as a new mix. The container one ratio interface element 1122 and the container two ratio interface element 1124 can provide a user with a slider that adjusts the percentages of each type of vaporizable material based on the user dragging the slider. In an aspect, a mix can comprise 100% on one type of vaporizable material or any percent combination (e.g., 50/50, 75/25, 85/15, 95/5, etc. . . . ). Once the user is satisfied with the new mix, the user can select Save 1126 to save the new mix for later use.

In the event a user selects the Aroma Mode 1104, the exemplary vapor device 900 will be configured to vaporize material and release the resulting vapor into the atmosphere. The user can be presented with user interface 1100b, 1100c, and/or 1100d as described above, but the resulting vapor will be released to the atmosphere.

In an aspect, the user can be presented with user interface 1100e. The user interface 1100e can provide the user with interface elements Identify 1128, Save 1130, and Upload 1132. The interface element Identify 1128 enables a user to engage one or more sensors in the exemplary vapor device 900 to analyze the surrounding environment. For example, activating the interface element Identify 1128 can engage a sensor to determine the presence of a negative environmental condition such as smoke, a bad smell, chemicals, etc. Activating the interface element Identify 1128 can engage a sensor to determine the presence of a positive environmental condition, for example, an aroma. The interface element Save 1130 enables a user to save data related to the analyzed negative and/or positive environmental condition in memory local to the exemplary vapor device 900. The interface element Upload 1132 enables a user to engage a network access device to transmit data related to the analyzed negative and/or positive environmental condition to a remote server for storage and/or analysis.

In an aspect, the user interfaces provided via the display 902 of the exemplary vapor device 900 can be used to select a mix of vaporizable material for vaporization. The exemplary vapor device 900 can be coupled to the robotic vapor device 101 and the mix can be vaporized and resultant vapor drawn into the robotic vapor device 101. The robotic vapor device 101 can analyze the vapor and provide information related to the contents of the vapor. The information can be compared to the intended mix to confirm that the exemplary vapor device 900 does not require calibration to properly mix and/or vaporize the mix of vaporizable material.

Figure 12:
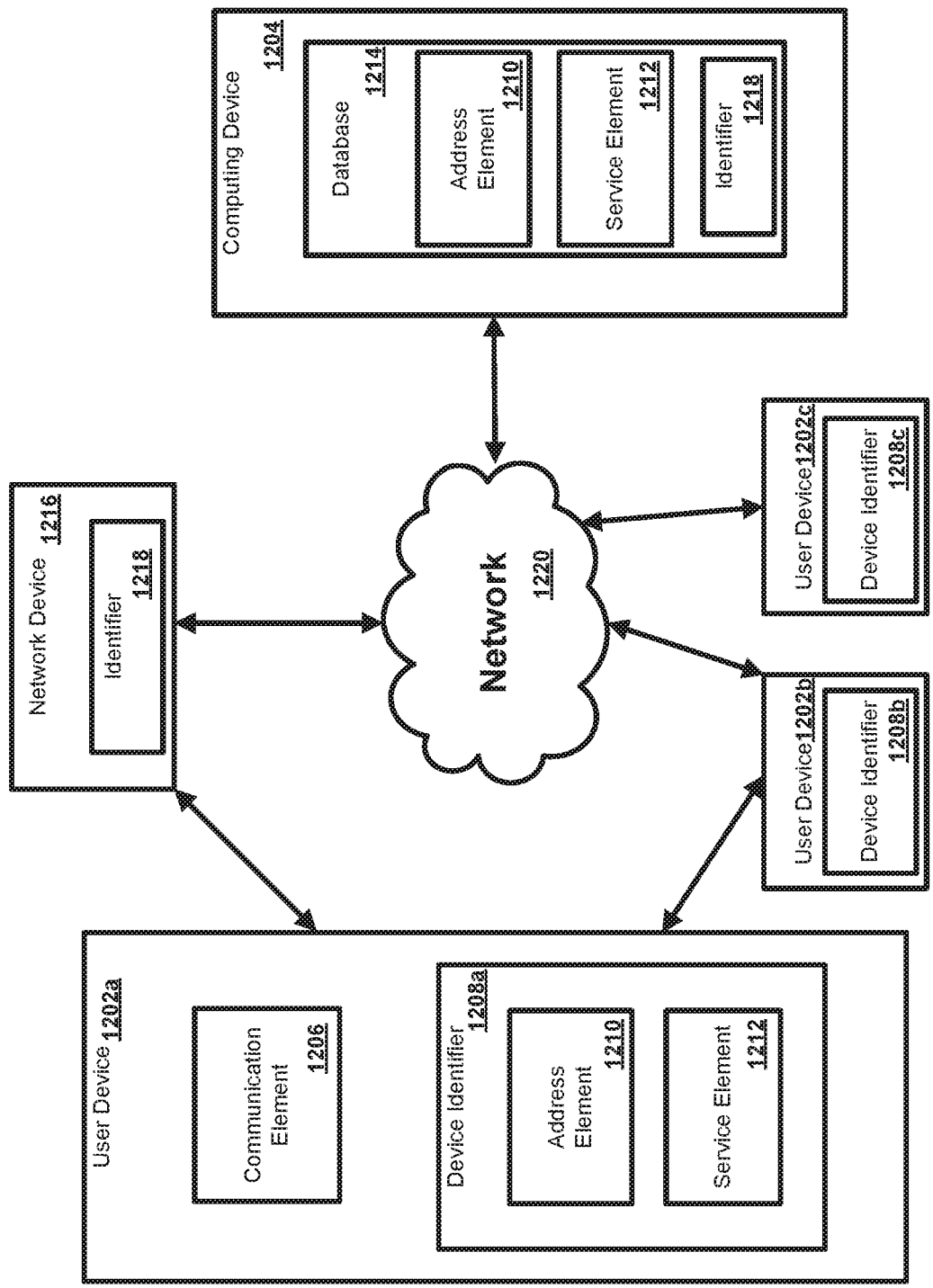
FIG. 12 illustrates an exemplary operating environment.

In one aspect of the disclosure, a system can be configured to provide services such as network-related services to a user device. FIG. 12 illustrates various aspects of an exemplary environment in which the present methods and systems can operate. The present disclosure is relevant to systems and methods for providing services to a user device, for example, electronic vapor devices which can include, but are not limited to, a vape-bot, micro-vapor device, vapor pipe, e-cigarette, hybrid handset and vapor device, and the like. Other user devices that can be used in the systems and methods include, but are not limited to, a smart watch (and any other form of "smart" wearable technology), a smartphone, a tablet, a laptop, a desktop, and the like. In an aspect, one or more network devices can be configured to provide various services to one or more devices, such as devices located at or near a premises. In another aspect, the network devices can be configured to recognize an authoritative device for the premises and/or a particular service or services available at the premises. As an example, an authoritative device can be configured to govern or enable connectivity to a network such as the Internet or other remote resources, provide address and/or configuration services like DHCP, and/or provide naming or service discovery services for a premises, or a combination thereof. Those skilled in the art will appreciate that present methods can be used in various types of networks and systems that employ both digital and analog equipment. One skilled in the art will appreciate that provided herein is a functional description and that the respective functions can be performed by software, hardware, or a combination of software and hardware.

The network and system can comprise a user device 1202a, 1202b, and/or 1202c in communication with a computing device 1204 such as a server, for example. The computing device 1204 can be disposed locally or remotely relative to the user device 1202a, 1202b, and/or 1202c. As an example, the user device 1202a, 1202b, and/or 1202c and the computing device 1204 can be in communication via a private and/or public network 1220 such as the Internet or a local area network. Other forms of communications can be used such as wired and wireless telecommunication channels, for example. In another aspect, the user device 1202a, 1202b, and/or 1202c can communicate directly without the use of the network 1220 (for example, via Bluetooth®, infrared, and the like).

In an aspect, the user device 1202a, 1202b, and/or 1202c can be an electronic device such as an electronic vapor device (e.g., vape-bot, micro-vapor device, vapor pipe, e-cigarette, hybrid handset and vapor device), a robotic vapor device, a smartphone, a smart watch, a computer, a smartphone, a laptop, a tablet, a set top box, a display device, or other device capable of communicating with the computing device 1204. As an example, the user device 1202*a*, 1202*b*, and/or 1202*c* can comprise a communication element 1206 for providing an interface to a user to interact with the user device 1202*a*, 1202*b*, and/or 1202*c* and/or the computing device 1204. The communication element 1206 can be any interface for presenting and/or receiving information to/from the user, such as user feedback. An example interface can be communication interface such as a web browser (e.g., Internet Explorer, Mozilla Firefox, Google Chrome, Safari, or the like). Other software, hardware, and/or interfaces can be used to provide communication between the user and one or more of the user device 1202*a*, 1202*b*, and/or 1202*c* and the computing device 1204. In an aspect, the user device 1202*a*, 1202*b*, and/or 1202*c* can have at least one similar interface quality such as a symbol, a voice activation protocol, a graphical coherence, a startup sequence continuity element of sound, light, vibration or symbol. In an aspect, the interface can comprise at least one of lighted signal lights, gauges, boxes, forms, words, video, audio scrolling, user selection systems, vibrations, check marks, avatars, matrix', visual images, graphic designs, lists, active calibrations or calculations, 2D interactive fractal designs, 3D fractal designs, 2D and/or 3D representations of vapor devices and other interface system functions.

As an example, the communication element 1206 can request or query various files from a local source and/or a remote source. As a further example, the communication element 1206 can transmit data to a local or remote device such as the computing device 1204. In an aspect, data can be shared anonymously with the computing device 1204.

In an aspect, the user device 1202*a*, 1202*b*, and/or 1202*c* can be associated with a user identifier or device identifier 1208*a*, 1208*b*, and/or 1208*c*. As an example, the device identifier 1208*a*, 1208*b*, and/or 1208*c* can be any identifier, token, character, string, or the like, for differentiating one user or user device (e.g., user device 1202*a*, 1202*b*, and/or 1202*c*) from another user or user device. In a further aspect, the device identifier 1208*a*, 1208*b*, and/or 1208*c* can identify a user or user device as belonging to a particular class of users or user devices. As a further example, the device identifier 1208*a*, 1208*b*, and/or 1208*c* can comprise information relating to the user device such as a manufacturer, a model or type of device, a service provider associated with the user device 1202*a*, 1202*b*, and/or 1202*c*, a state of the user device 1202*a*, 1202*b*, and/or 1202*c*, a locator, and/or a label or classifier. Other information can be represented by the device identifier 1208*a*, 1208*b*, and/or 1208*c*.

In an aspect, the device identifier 1208*a*, 1208*b*, and/or 1208*c* can comprise an address element 1210 and a service element 1212. In an aspect, the address element 1210 can comprise or provide an internet protocol address, a network address, a media access control (MAC) address, an Internet address, or the like. As an example, the address element 1210 can be relied upon to establish a communication session between the user device 1202*a*, 1202*b*, and/or 1202*c* and the computing device 1204 or other devices and/or networks. As a further example, the address element 1210 can be used as an identifier or locator of the user device 1202*a*, 1202*b*, and/or 1202*c*. In an aspect, the address element 1210 can be persistent for a particular network.

In an aspect, the service element 1212 can comprise an identification of a service provider associated with the user device 1202*a*, 1202*b*, and/or 1202*c* and/or with the class of user device 1202*a*, 1202*b*, and/or 1202*c*. The class of the user device 1202*a*, 1202*b*, and/or 1202*c* can be related to a type of device, capability of device, type of service being provided, and/or a level of service. As an example, the service element 1212 can comprise information relating to or provided by a communication service provider (e.g., Internet service provider) that is providing or enabling data flow such as communication services to and/or between the user device 1202*a*, 1202*b*, and/or 1202*c*. As a further example, the service element 1212 can comprise information relating to a preferred service provider for one or more particular services relating to the user device 1202*a*, 1202*b*, and/or 1202*c*. In an aspect, the address element 1210 can be used to identify or retrieve data from the service element 1212, or vice versa. As a further example, one or more of the address element 1210 and the service element 1212 can be stored remotely from the user device 1202*a*, 1202*b*, and/or 1202*c* and retrieved by one or more devices such as the user device 1202*a*, 1202*b*, and/or 1202*c* and the computing device 1204. Other information can be represented by the service element 1212.

In an aspect, the computing device 1204 can be a server for communicating with the user device 1202*a*, 1202*b*, and/or 1202*c*. As an example, the computing device 1204 can communicate with the user device 1202*a*, 1202*b*, and/or 1202*c* for providing data and/or services. As an example, the computing device 1204 can provide services such as calibration analysis, vapor analysis, data sharing, data syncing, network (e.g., Internet) connectivity, network printing, media management (e.g., media server), content services, and the like. In an aspect, the computing device 1204 can allow the user device 1202*a*, 1202*b*, and/or 1202*c* to interact with remote resources such as data, devices, and files. As an example, the computing device can be configured as (or disposed at) a central location, which can receive content (e.g., data) from multiple sources, for example, user devices 1202*a*, 1202*b*, and/or 1202*c*. The computing device 1204 can combine the content from the multiple sources and can distribute the content to user (e.g., subscriber) locations via a distribution system.

In an aspect, one or more network devices 1216 can be in communication with a network such as network 1220. As an example, one or more of the network devices 1216 can facilitate the connection of a device, such as user device 1202*a*, 1202*b*, and/or 1202*c*, to the network 1220. As a further example, one or more of the network devices 1216 can be configured as a wireless access point (WAP). In an aspect, one or more network devices 1216 can be configured to allow one or more wireless devices to connect to a wired and/or wireless network using Wi-Fi, Bluetooth or any desired method or standard.

In an aspect, the network devices 1216 can be configured as a local area network (LAN). As an example, one or more network devices 1216 can comprise a dual band wireless access point. As an example, the network devices 1216 can be configured with a first service set identifier (SSID) (e.g., associated with a user network or private network) to function as a local network for a particular user or users. As a further example, the network devices 1216 can be configured with a second service set identifier (SSID) (e.g., associated with a public/community network or a hidden network) to function as a secondary network or redundant network for connected communication devices.

In an aspect, one or more network devices 1216 can comprise an identifier 1218. As an example, one or more identifiers can be or relate to an Internet Protocol (IP) Address IPV4/IPV6 or a media access control address (MAC address) or the like. As a further example, one or more identifiers 1218 can be a unique identifier for facilitating communications on the physical network segment. In an aspect, each of the network devices 1216 can comprise a distinct identifier 1218. As an example, the identifiers 1218 can be associated with a physical location of the network devices 1216.

In an aspect, the computing device 1204 can manage the communication between the user device 1202*a*, 1202*b*, and/or 1202*c* and a database 1214 for sending and receiving data therebetween. As an example, the database 1214 can store a plurality of files (e.g., web pages), user identifiers or records, or other information. In one aspect, the database 1214 can store user device 1202*a*, 1202*b*, and/or 1202*c* usage information (including chronological usage), test results, type of vaporizable and/or non-vaporizable material used, frequency of usage, location of usage, recommendations, communications (e.g., text messages, advertisements, photo messages), simultaneous use of multiple devices, and the like). The database 1214 can collect and store data to support cohesive use, wherein cohesive use is indicative of the use of a first electronic vapor devices and then a second electronic vapor device is synced chronologically and logically to provide the proper specific properties and amount of vapor based upon a designed usage cycle. As a further example, the user device 1202*a*, 1202*b*, and/or 1202*c* can request and/or retrieve a file from the database 1214. The user device 1202*a*, 1202*b*, and/or 1202*c* can thus sync locally stored data with more current data available from the database 1214. Such syncing can be set to occur automatically on a set time schedule, on demand, and/or in real-time. The computing device 1204 can be configured to control syncing functionality. For example, a user can select one or more of the user device 1202*a*, 1202*b*, and/or 1202*c* to never by synced, to be the master data source for syncing, and the like. Such functionality can be configured to be controlled by a master user and any other user authorized by the master user or agreement.

In an aspect, data can be derived by system and/or device analysis. Such analysis can comprise at least by one of instant analysis performed by the user device 1202*a*, 1202*b*, and/or 1202*c* or archival data transmitted to a third party for analysis and returned to the user device 1202*a*, 1202*b*, and/or 1202*c* and/or computing device 1204. The result of either data analysis can be communicated to a user of the user device 1202*a*, 1202*b*, and/or 1202*c* to, for example, inform the user of their vapor device configuration, eVapor use and/or lifestyle options. In an aspect, a result can be transmitted back to at least one authorized user interface.

In an aspect, the database 1214 can store information relating to the user device 1202*a*, 1202*b*, and/or 1202*c* such as the address element 1210 and/or the service element 1212. As an example, the computing device 1204 can obtain the device identifier 1208*a*, 1208*b*, and/or 1208*c* from the user device 1202*a*, 1202*b*, and/or 1202*c* and retrieve information from the database 1214 such as the address element 1210 and/or the service elements 1212. As a further example, the computing device 1204 can obtain the address element 1210 from the user device 1202*a*, 1202*b*, and/or 1202*c* and can retrieve the service element 1212 from the database 1214, or vice versa. Any information can be stored in and retrieved from the database 1214. The database 1214 can be disposed remotely from the computing device 1204 and accessed via direct or indirect connection. The database 1214 can be integrated with the computing device 1204 or some other device or system. Data stored in the database 1214 can be stored anonymously and can be destroyed based on a transient data session reaching a session limit.

By way of example, one or more of the user device 1202*a*, 1202*b*, and/or 1202*c* can comprise a robotic vapor device and one or more of the user device 1202*a*, 1202*b*, and/or 1202*c* can comprise a vapor device coupled to the robotic vapor device for testing and/or reconfiguration. The robotic vapor device can draw vapor from the vapor device (e.g., as a user would inhale from the vapor device) and analyze the resulting vapor. In an aspect, the robotic vapor device can transmit testing results and or data to the computing device 1204 for analysis. For example, a determination can be made that the vapor device is generating vapor at a temperature above a recommend limit. A reconfiguration command can be sent to the vapor device (e.g., via the robotic vapor device and/or the computing device 1204) to lower the temperature at which vaporization occurs. Any number of other functions/features/aspects of operation of the vapor device can be tested/analyzed and reconfigured.

Figure 13:
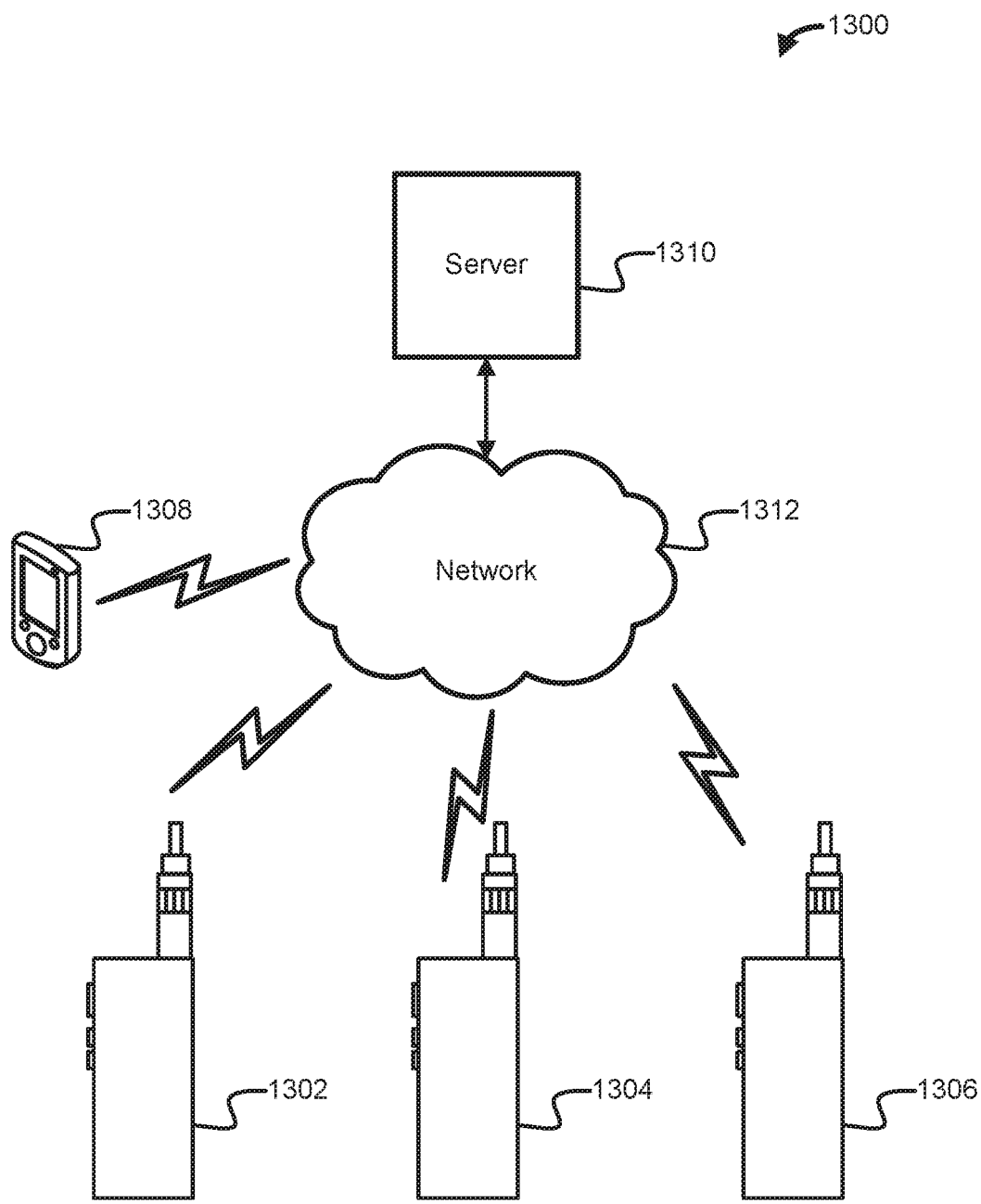
FIG. 13 illustrates another exemplary operating environment.

FIG. 13 illustrates an ecosystem 1300 configured for sharing and/or syncing data such as usage information (including chronological usage), testing data, reconfiguration data, type of vaporizable and/or non-vaporizable material used, frequency of usage, location of usage, recommendations, communications (e.g., text messages, advertisements, photo messages), simultaneous use of multiple devices, and the like) between one or more devices such as a vapor device 1302, a vapor device 1304, a vapor device 1306, and an electronic communication device 1308. In an aspect, the vapor device 1302, the vapor device 1304, the vapor device 1306 can be one or more of an e-cigarette, an e-cigar, an electronic vapor modified device, a hybrid electronic communication handset coupled/integrated vapor device, a micro-sized electronic vapor device, or a robotic vapor device. In an aspect, the electronic communication device 1308 can comprise one or more of a smartphone, a smart watch, a tablet, a laptop, and the like.

In an aspect data generated, gathered, created, etc., by one or more of the vapor device 1302, the vapor device 1304, the vapor device 1306, and/or the electronic communication device 1308 can be uploaded to and/or downloaded from a central server 1310 via a network 1312, such as the Internet. Such uploading and/or downloading can be performed via any form of communication including wired and/or wireless. In an aspect, the vapor device 1302, the vapor device 1304, the vapor device 1306, and/or the electronic communication device 1308 can be configured to communicate via cellular communication, WiFi communication, Bluetooth® communication, satellite communication, and the like. The central server 1310 can store uploaded data and associate the uploaded data with a user and/or device that uploaded the data. The central server 1310 can access unified account and tracking information to determine devices that are associated with each other, for example devices that are owned/used by the same user. The central server 1310 can utilize the unified account and tracking information to determine which of the vapor device 1302, the vapor device 1304, the vapor device 1306, and/or the electronic communication device 1308, if any, should receive data uploaded to the central server 1310. For example, the central server 1310 can receive reconfiguration data generated as a result of analysis of the vapor device 1302, the vapor device 1304, the vapor device 1306 by a robotic vapor device. The reconfiguration data can be shared with one or more of the vapor device 1302, the vapor device 1304, the vapor device 1306 to reconfigure the vapor device 1302, the vapor device 1304, and the vapor device 1306.

Figure 14:
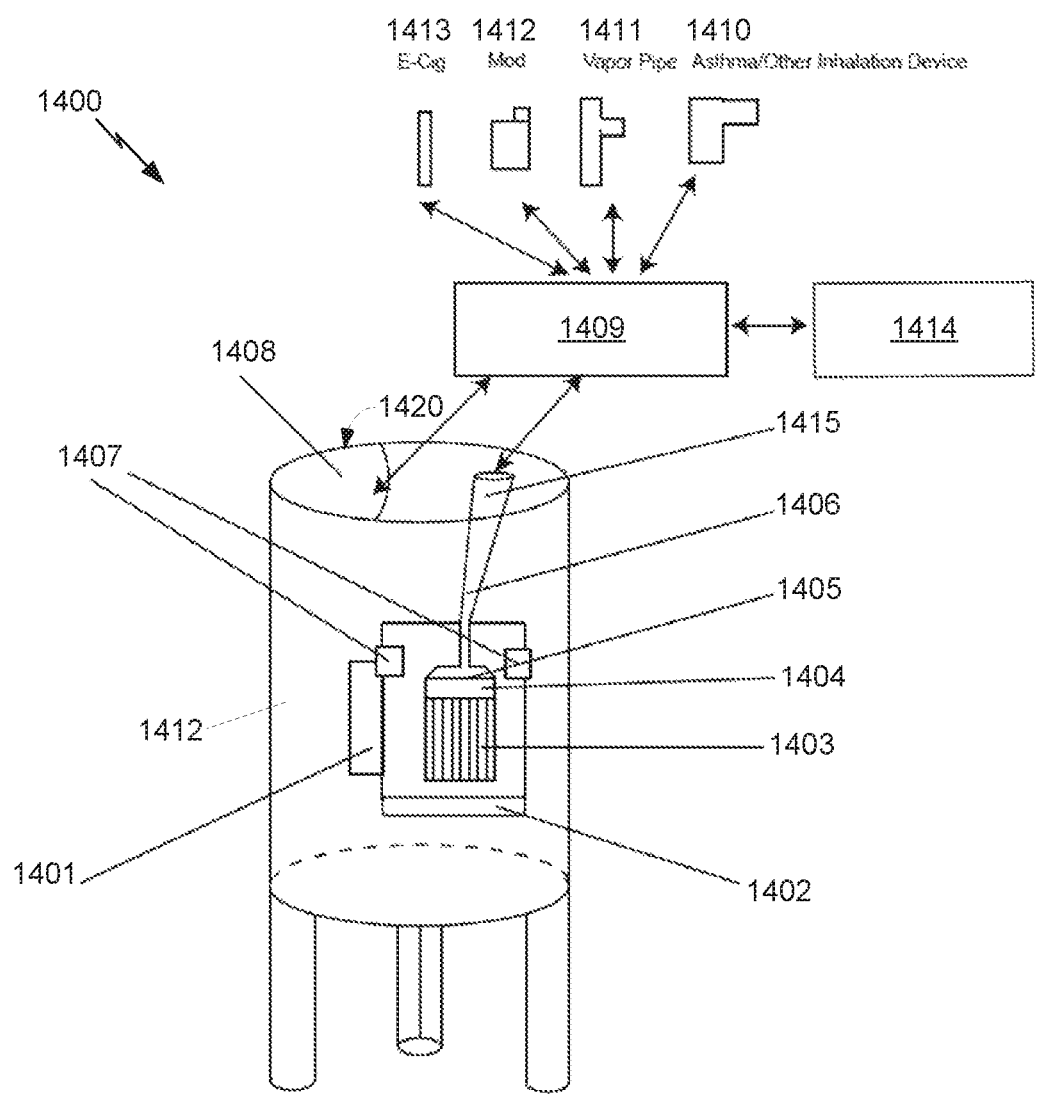
FIG. 14 is a schematic diagram illustrating an example calibration vapor device.

Aspects of the present disclosure pertain to the manufacture, design, implementation, and installation of a robotic sensing intake and distribution vapor device 1420, shown in FIG. 14. The robotic sensing intake and distribution vapor device 1420 may also be called a "robotic vapor device" (RVD), "air analyzer and air treatment apparatus" or "Vape-Bot" ™ for brevity. The robotic vapor device 1420 may be equipped to test and analyze gases or other substances emitted from a personal vaporizer 1411, 1412, 1413 or another vaporizer and/or nebulizer 1410 (hereinafter, "vaporizer"), to exhaust such gases or substances to an ambient environment, and to communicate with other components 1409 of a networked system 1400. In embodiments, the vaporizer 1410, 1411, 1412, 1413 may be electrically coupled to the robotic vapor device 1420 via a server 1409 such that data can be transmitted between the robotic vapor device 1420 and the vaporizer via the server 1409.

In addition, the robotic vapor device 1420 may have the ability to intake and test ambient air quality, as well as output from personal vaporizers by the expedient of simply removing the attached vaporizer 1410, 1411, 1412, 1413 or replacing the vaporizer with a desired pre-treatment system such as a filter. In either case, the robotic vapor device 1420 may include a suction mechanism 1415 comprising, for example, a piston in a cylinder (which doubles as an analysis chamber), a bellows, or an intake fan. The suction mechanism 1415 may be set at a constant rate or at a rate designed to simulate human respiration, drawing air in through a vapor path 1406. Once analyzed (or immediately, if no analysis is to be performed) the in-drawn vapor or mixture may be exhausted via the vapor path 1406, or via a different outlet (not shown).

Furthermore, the robotic vapor device 1420 may analyze vapor or gaseous substances using at least one of a sensor array 1407 or a gas chromatograph/mass spectrometry system (GC/MS, not shown) installed within the robotic device and coupled to an analysis chamber. Sensor data and spectrometry analysis data may be provided to a data processing and control system 1401 in the robotic vapor device 1420, and utilized for analysis. The processing and control system may analyze the sensor or spectrometer data by comparison to a cached database (not shown) for element and level matching, using an engine comprising analysis algorithms. In the alternative, or in addition, measurement data may be securely transmitted to at least one remote database (such as integral or coupled to server 1409) for analysis and subsequent transmission back to the robotic device or at least one interface thereof on the instant device or any authorized third party device. The data may then be displayed on any web enabled, system authorized device.

Novel aspects of the robotic vapor device 1420 and system 1400, and methods for their use, may include a portable, robotic air analyzer and air treatment apparatus that can be used in the home or at a commercial establishment to provide a rapid and accurate analysis of output from a personal vaporizer 1410, 1411, 1412, 1413. For example, constituents of vapor output may be analyzed to detect the purity and potency of the vapor, verifying the vapor is supplied as the vaporizer or its fluid supply was labeled for sale.

The robotic vapor device 1420 also be used to track vapor residue (e.g., particulate or non-volatile residuals), levels of inhalation of specific chemicals, impact of different draw rates or respiration patterns on vaporizer output and determinations of positive and negative impacts of vapor inhalation usage. This information may be based not only on the chemical raw data gauged at intake by the device, but also on comparisons of that data to other known data in local or remote databases. Such comparisons can be made a static environment or dynamic sensor data environment. For example, the robotic vapor device 1420 may be equipped with any number of sensor components or targets, including, for example, PH gauges, human/animal/plant or simulated tissue and any other number of other materials testing beds.

The robotic vapor device 1420 may also be used to distribute desired vapor into environments based upon a specific order or setting of the system. This vapor does not require a human to inhale the vapor. Instead, the vapor is delivered via an outtake exhaust system, which may exhaust in a steady, rhythmic or sporadic output stream. Once the desired level of the desired vapor elements have been disbursed by the robotic vapor device 1420, the device may then cease to deliver such elements until there is another need. This need may be determined by demand of an authorized party, or triggered via a sensor reading within a space that the robotic vapor device 1420 is serving with customized vapor. The vapor may be pure vapor or may contain non-vaporizable elements as well. The vapor or other non-vaporizable elements may be medicine, therapeutic materials, material for promoting or protecting wellness, aromatherapy materials, or substances for recreational use, e.g., psychoactive substances, flavorings or odors for entertainment purposes, or for enhancing a virtual reality simulation. The robotic vapor device 1420 may also test ambient air to make sure it is in compliance with safety, medical and generally needed or desired guidelines.

In order to deliver vapor to a prescribed area, the robotic vapor device 1420 may include one or more liquid chambers 1403 for containing vaporizable and non-vaporizable material, a mixing chamber 1404, and a heating element 1405. The mixing chamber may receive material from one or more liquid chambers 1403 and allow the materials to mix prior to vaporization or nebulization. The heating element may be in fluid communication with the mixing chamber 1404 and may vaporize or nebulize the material in the mixing chamber 1404.

The system 1400 and robotic vapor device 1420 may be instantly, remotely or self-powered via a battery or self-powering mechanism, such as a solar cell, hand crank, fuel cell, electrochemical cell, wind turbine and the like. For example, a portable device may include a battery or other power source 1402 capable of off-the-grid power, or may be connected to an external power source. The robotic vapor device 1420 may further include a self-calibration system utilizing a base of molecular sensing levels associated with a specific set of vapor intake cartridges utilized specifically for the calibration of the device. Such calibration cartridges may be installed in the inlet of the suction mechanism 1405, replacing the personal vaporizer 1410, 1411, 1412, 1413, or in a different inlet. These vapor calibration cartridges may be manufactured to output specified and calibrated concentrations on specific substances when exposed to a specific suction profile of the robotic vapor device 1420. Thus, such cartridges may be used to calibrate the sensor capabilities of the robotic vapor device 1420 and verify sensor readings by the device. Readings by the robotic vapor device 1420 that do not meet the known levels of the test vapor cartridge may be used to indicate a need to repair, replace or recalibrate sensor equipment via the sensor grid, mass spectrometry equipment and database veracity. The robotic vapor device 1420 may also self-calibrate using data provided by the server 1409. For example, the server 1409 may receive calibration information directly from another device 1410,

1411, 1412, 1413, and the robotic vapor device 1420 may use this calibration data to self-calibrate.

The robotic vapor device 1420 may include a gas chromatograph and mass spectrometer (GC-MS) that includes a gas chromatograph with its output coupled to an input of the mass spectrometer (not shown). Further details of a GC-MS adapted for use in the robotic vapor device 1420 are provided below in connection with FIG. 15. After the vapor being analyzed by the device is ionized and separated via exposure to charging fields the results may then be correlated against existing results in a database local to the robotic vapor device 1420, or the results may be transmitted for correlating against a remote database server. A remote server 1409 may then transmit the result back to at least one of the robotic vapor device 1420, or any authorized third party device(s) 1410, 1411, 1412, 1413, or an interface 1414 remote from the robotic vapor device 1420 or instant to the primary device. Additionally, at any point in an ionization process or any other spectrometry process configured inside the robotic vapor device 1420 where measurement data may be capable of providing a useful result via extrapolation, then at least one of visual images along with hard data of the results of the spectrometry may be captured and analyzed instantly to correlate a result against a local database or transmitted for the same purpose.

The robotic vapor device 1420 may be utilized instantly as a standalone device to service one or many rooms, as the device is scalable to service larger and larger square foot areas. Larger devices are also capable of servicing more and more custom vapor solutions to multiple rooms simultaneously, via multiple outlet ports. The robotic vapor device 1420 and system 1400 may also be integrated with existing HVAC systems to provide monitoring, custom air elements and testing within the distribution system for the HVAC. Micro-sized versions of the robotic vapor device 1420 may be utilized in small spaces such as in volatile chemical areas, inside of protective clothing such as HAZMAT suits or space suits. The micro-devices may also be utilized for vehicles, cockpits, police and fire outfits, elevators, or other small confined spaces.

The robotic vapor device 1420 may be suitable for air treatment in homes, the workplace, hospitals, airplanes, trains, buses, trucks, shipping containers, airport security, schools, entertainment venues, vapor lounges and vapor bars, mortuaries and places of worship, among many others.

Multiple robotic vapor devices 1420 or vaporizers 1410, 1411, 1412, 1413 in use for the same or different purpose or environments may share data to view normalized aggregate levels, aggregate, store & analyze data, while refining and creating state of the art solutions and formulas as a result of viewing best practices and results.

Accordingly, aspects of the disclosure concern a system, method and device including a robotic sensing intake and distribution vapor device, where the device functions as at least one of an air testing device, an air supplementing device and a remote data sharing device. In an aspect, the device utilizes mass spectrometry to analyze at least one of intake air or vapor samples. In another aspect, data analysis of the samples obtained from the RVD via mass spectrometry may be performed in at least one of the instant device or a remote device. For example, where the data analysis performed at least one of locally or remotely via correlative database, an analysis result may be transmitted back to the at least one of the RVD, an interface instant to the RVD, an authorized third party device or the like.

In other aspects, an RVD may be configured to intake vapor at different rates via different suction mechanism setting, and for measuring data at different inhalation rates. Accordingly, a user may be assured that the way in which he or she uses a vaporization device creates a definite and known output.

In other aspects, a system, method and device including an RVD may be used to delivers vapor to a prescribed area. In such embodiments, an RVD may formulate data based upon at least one of a default setting, a remote authorized order, results of a real time or archival data analysis and system rules. The RVD may apply such control sources or parameters to determine customized dispensing ratios and rates for formulation of multiple liquids stored in the RVD, or in a coupled vaporizer device. An RVD and a detachable vaporizer coupled to the RVD may coordinate operation by communication between connected processors, to provide the same or similar output as an RVP with vaporization capabilities. Either way, an RVD may be, or may include, at least one of a standalone device to service a single confined space, a standalone device to service multiple confined spaces, micro-sized devices to service small confined spaces, or an integrated device to work in unison with an HVAC system. A system of multiple RVDs may share data with each other and with at least one central or sub central database. The shared data or analyzed data may be used to alter settings of at least one networked device, e.g., any one of the multiple RVD's or any vaporizer coupled to it.

Figure 15:
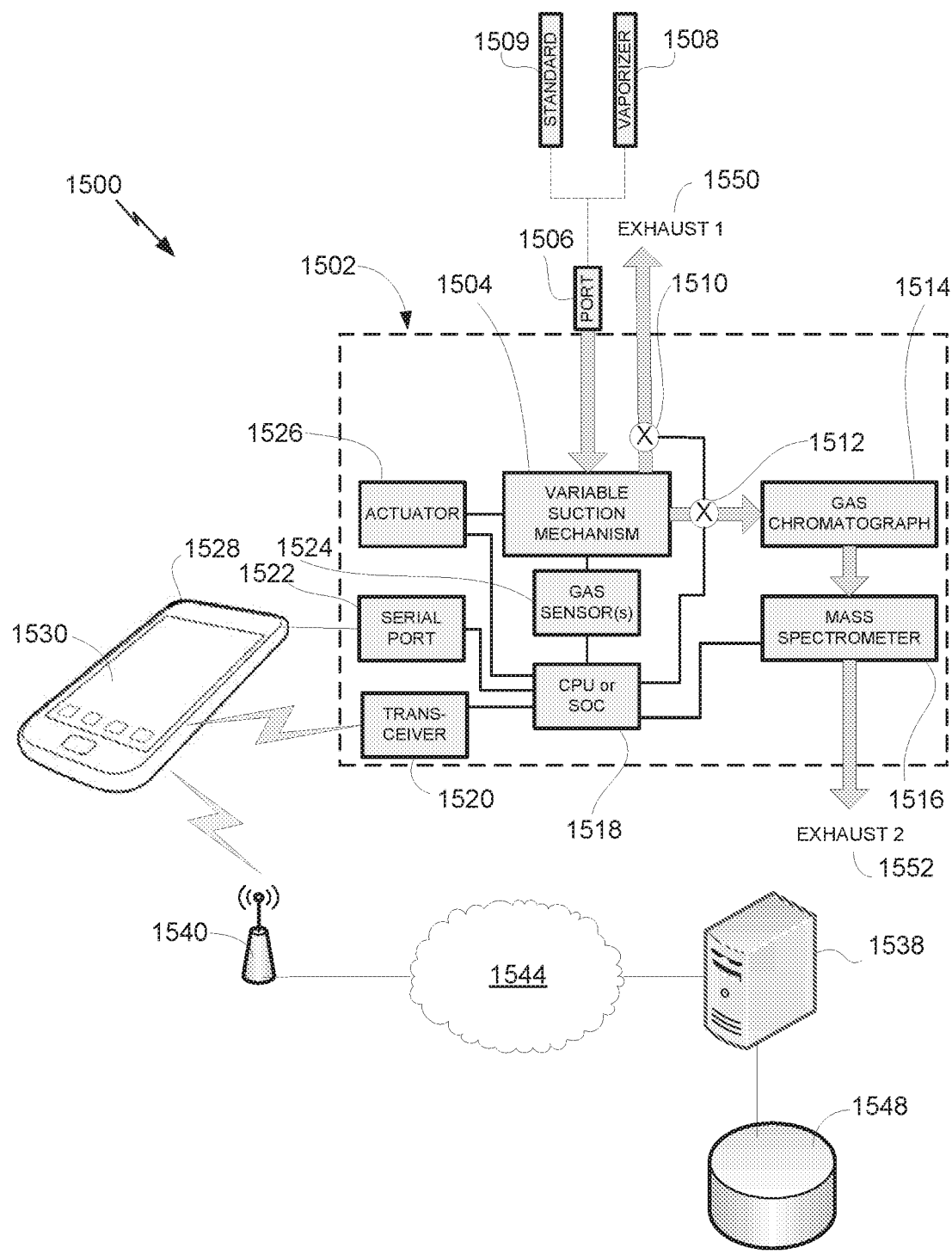
FIG. 15 is a schematic diagram illustrating alternative aspects of a system for determining and implementing calibration parameters.

Referring to FIG. 15, alternative or additional aspects of a system 1500 for testing of a personal vapor device are illustrated. The system 1500 may include an assembly 1502, also called a respiration simulating vapor analysis and distribution device, which may be enclosed in a housing of portable form factor. The assembly 1502 may include a suction mechanism 1504 configured to draw an output from a personal vaporizer 1508 or a standardized vapor device 1509 placed in an inlet port 1506 of the assembly 1502. The standardized vapor device 1509 includes a standardized vaporizable or non-vaporizable material including known constituents, such that a particular volume of the standardized material includes known amounts of the constituents. The standardized vapor device 1509 also includes a vaporizer or nebulizer capable of vaporizing or nebulizing the standardized material. In that regard, the standardized vapor device 1509 includes standardized components and functions, and includes settings thereof that may be set to a default, may be set to a custom value, or may be incrementally adjusted between values. The suction mechanism 1504 may be, or may include, a variable volume, variable speed mechanism, for example, a variable-volume piston pump, variable expansion bellows or variable speed gas pump. The suction mechanism 1504 may be in fluid communication with at least one of a gas testing assembly (1524 or 1514/1516) or an exhaust port to ambient air (1550 or 1552). For example, a the gas testing assembly 1524 or 1514/1516 may be coupled to the suction mechanism via a tube, channel or other fluid coupling, or may include a sensor component that is installed inside of the suction mechanism itself, for example via a cylinder head. The suction mechanism 1504 may be communicatively coupled to a network communication device (1520 or 1522) via a processor 1518 and associated circuit. The air analyzer and air treatment apparatus 1502 may further include a processor 1518, for example, a central processing unit (CPU) or system on a chip (SOC) operatively coupled to at least one of the suction mechanism 1504, the gas testing assembly (1524 or 1514/1516), or the network communication device (1520 or 1522). As illustrated, the processor 1518 is communicatively coupled to all three of the suction mechanism 1504, the gas testing assembly (1524 or 1514/1516), or the network communication device (1520 or 1522). The coupling to the suction mechanism 1504 is via an actuator 1526, for example a motor, and may include other components as known in the art, for example a motor driving circuit.

For embodiments of the assembly 1502 that include the gas testing assembly (1524 and/or 1514/1516), the processor may be further configured to receive measurement data from the gas testing assembly. The gas testing assembly may include at least one of a gas sensor circuit 1524, or a GC/MS assembly 1514, 1516.

The processor 1518 may be configured to perform at least one of analyzing the measurement data, sending the measurement data to a network node 1528 (e.g., a smartphone, notepad computer, laptop computer, desktop computer, server, etc.), or receiving an analysis of the measurement data from the network node 1528. Accordingly, the respiration simulating vapor analysis and distribution device 1502 may further include a user interface port 1522 or 1520, wherein the processor is configured to determine a material to be measured based on an input from the user interface port. The user interface port may comprise a wired interface, for example a serial port 1522 such as a Universal Serial Bus (USB) port, an Ethernet port, or other suitable wired connection. The user interface port may comprise a wireless interface, for example a transceiver 1522 using any suitable wireless protocol, for example Wifi (IEEE 802.11), Bluetooth™, infrared, or other wireless standard. The user interface port may be configured to couple to at least one of a vaporizer 1508 or a mobile computing device 1528, and either of these 1508, 1528 may include a user interface for receiving user input. For example, a mobile computing device 1528 may include a touchscreen 1530 for both display output and user input.

The processor 1518 may be configured to activate a gas or vapor sensor circuit based on the material to be measured. For example, a user may indicate that formaldehyde is of particular concern, via a user interface 1530 of the mobile device 1528. In response to this input, the processor may activate an electrochemical or other sensor circuit that is specialized for sensing formaldehyde. This may include opening a valve 1510 to exhaust via a first port 1550 bypassing the GC/MS components 1514, 1516. In an alternative, or in addition, the processor 1518 may activate the GC/MS components 1514, 1516, including closing the first exhaust valve 1510 and opening a second valve 1512 leading to the GC 1514 and MS 1516. A filter component may be interposed between the GC 1514 and suction mechanism 1504 (or sample chamber) to prevent non-gaseous products from fouling the GC component 1514.

In an aspect, the suction mechanism 1504 further comprises at least one of a variable stroke piston, variable stroke bellows, or a rotary gas pump or fan. The mechanism 1504 may include a sample analysis chamber; for example, the cylinder of a piston pump may double as a sample chamber, with sensors embedded in a cylinder end. In an alternative, or in addition, the pump mechanism 1504 may be in fluid communication with a separate analysis chamber (not shown). The mechanism 1504 may further be configured to draw air or vapor at a variable rate. For example, the suction mechanism 1504 may be configured to draw air into an interior volume at a rate controlled at least in part by the processor 1518.

The air analyzer and air treatment apparatus 1502 may include at least one of an internal vaporizer (not shown) or a control coupling (e.g., via a connector in port 1506 or via a wireless coupling) to a detachable vaporizer 1508. The processor 1518 may be configured to control vapor output of at least one of the internal vaporizer or the detachable vaporizer 1508.

In an aspect, the processor 1518 may be configured to control the vapor output of the vaporizer 1508 or an internal vaporizer for a defined vapor concentration target in a confined space, over a defined period of time. For example, a defined concentration of a medication or fragrance may be targeted, with real-time feedback analyzed and used for control via the assembly's gas sensing circuits 1524, 1514/1516. Thus, the air analyzer and air treatment apparatus may be used as a feedback controlled or open-loop controlled vapor dispensing device for a room or confined space. Accordingly, the processor may be configured to control the vapor output based on at least one of a default setting, a remote authorized order, current measurement data, archived measurement data, system rules, or a custom formulation of multiple vaporizable materials, in addition to, or instead of, feed back data.

The vaporizer 1508 may be coupled to one or more containers containing a vaporizable material, for example a fluid. For example, coupling may be via wicks, via a valve, or by some other structure. The coupling mechanism may operate independently of gravity, such as by capillary action or pressure drop through a valve. The vaporizer may be configured to vaporize the vaporizable material from one or more containers at controlled rates, and/or in response to suction applied by the assembly 1502, and/or in response to control signals from the assembly 1502. In operation, the vaporizer 1508 may vaporize or nebulize the vaporizable material, producing an inhalable mist. In embodiments, the vaporizer may include a heater coupled to a wick, or a heated wick. A heating circuit may include a nickel-chromium wire or the like, with a temperature sensor (not shown) such as a thermistor or thermocouple. Within definable limits, by controlling suction-activated power to the heating element, a rate of vaporization may be controlled. At minimum, control may be provided between no power (off state) and one or more powered states. Other control mechanisms may also be suitable.

The processor 1518 may be coupled to the vaporizer 1508 via an electrical circuit, configured to control a rate at which the vaporizer 1508 vaporizes the vaporizable material. In operation, the processor 1518 may supply a control signal to the vaporizer 1508 that controls the rate of vaporization. A transceiver port 1520 is coupled to the processor, and the processor may transmit data determining the rate to a receiver on the vaporizer 1508. Thus, the vaporization rate of the vaporizer 1508 may be remotely controllable from the assembly 1502, by providing the data. The processor 1518 may be, or may include, any suitable microprocessor or microcontroller, for example, a low-power application-specific controller (ASIC) designed for the task of controlling a vaporizer as described herein, or (less preferably) a general-purpose central processing unit, for example, one based on 80×86 architecture as designed by Intel™ or AMD™, or a system-on-a-chip as designed by ARM™, or a custom-designed system-on-a-chip optimized for gas analysis and other operations of the assembly 1502 as described. The processor 1518 may be communicatively coupled to auxiliary devices or modules of the vaporizing apparatus 1502, using a bus or other coupling. Optionally, the processor 1518 and some or all of its coupled auxiliary devices or modules may be housed within or coupled to a housing substantially enclosing the suction mechanism 1504, the processor 1518, the transceiver port 1512, and other illustrated components. The assembly 1502 and housing may be configured together in a form factor of a friendly robot, a human bust, a sleek electronic appliance, or other desired form.

The assembly 1502 may be capable of being self-calibrated or otherwise calibrated. For example, the assembly's gas sensing circuits 1524, 1514/1516 or settings thereof can be adjusted so that the sensing circuits and assembly 1502 can more accurately determine constituents of material. In that regard, a standardized vapor device 1509 may be coupled to the assembly 1502 via the port 1506 or another port, such as a specific calibration port. The standardized vapor device 1509 may include a vaporizable or non-vaporizable standardized material having known amounts of particular constituents. The processor 1518 may cause the suction mechanism 1504 to draw vapor, gas, or an aerosol material from the standardized vapor device 1509 at a given rate. The sensors 1524, 1514/1516 can then detect the amounts of one or more constituents. The amounts and/or constituents can be determined by the processor 1518 and/or a remote device, such as the server 1538, based on the data detected by the sensors 1524, 1514/1516. Because the constituents of the standardized vapor device 1509 are known, the assembly 1502 can compare the detected constituents to the known constituents to determine calibration parameters.

In various embodiments, the processor 1518 is capable of detecting an identifier of the standardized vapor device 1509 and using the identifier to lookup the known amounts of the constituents from a memory or storage device. For example, the assembly 1502 may include an optical sensor for sensing an optical code (the identifier) associated with the standardized vapor device 1509. The assembly 1502 may also or instead include an RFID reader capable of sensing an RFID tag (identifier) of the standardized vapor device 1509. The assembly 1502 may also be in electrical communication with a memory or other storage associated with the standardized vapor device 1509 and may retrieve the identifier from the memory.

The processor 1518 is capable of determining a calibration result (i.e., an amount of calibration for improving detection quality) in various manners. As described above, the difference between the known constituents/amounts and the detected constituents/amounts can be used to determine the calibration result. In some embodiments, the processor 1502 can calibrate the assembly 1502 by automatically adjusting a measurement parameter of the assembly 1502. For example, settings for the sensor 1524, 1514/1516 may be adjusted, constituent determination parameters of the processor 1518 can be adjusted, or the like. In embodiments, the processor 1518 may perform one or more predetermined diagnostic tests based on the difference between the known constituents/amounts and the detected constituents/amounts. For example, the processor 1518 can recalibrate a component of the GC 1514, the MS 1516, or the gas sensor 1524. For example, the recalibration may include physically altering portions of the components, electronically altering electrical portions (including any electrical hardware), or the like. The processor 1518 can also adjust data ratios in databases. For example, a database may include a ratio of a detected value and a measurement value and the processor 1518 may change this ratio so that the measurement value more accurately represents the actual value. The processor 1518 can also adjust an intake volume, in case a smaller or larger volume results in the sensors/processor 1518 more accurately determining the actual constituents/amounts. The processor may also indicate whether a sensor requires replacement and either electrically replace the sensor with a different sensor, or output data indicating that the sensor requires replacement. The processor 1518 may also determine that internal mechanisms of the assembly 1502 require cleaning and may initiate an automatic cleaning system, or may output data indicating that at least one mechanism requires cleaning and/or the particular mechanism(s). The processor 1518 may also check power systems of the assembly 1502 to determine whether a desired amount of power is being provided to each associated electrical component. The processor 1518 may also determine whether a connection status of the communication port 1520, 1522 is properly transmitting and/or receiving data, and may attempt to repair the connection if not, and/or output data indicating that the communications are not properly established.

In some embodiments, the processor 1518 can communicate with other vapor analysis devices via a communication port 1520, 1522. For example, the processor 1518 may transmit the detected data to the other vapor analysis device such that the other device determines the constituents and quantities thereof. The processor may compare constituents determined by the assembly 1502 to constituents determined by the other device and use this information to determine calibration parameters. When the assembly processor 1518 determines that the assembly 1502 is calibrated, the processor 1518 may generate an output indicating the completed calibration.

In related aspects, the assembly 1502 includes a memory device (not shown) coupled to the processor 1518. The memory device may include a random access memory (RAM) holding program instructions and data for rapid execution or processing by the processor during control of the vaporizer 1502. When the vaporizer 1502 is powered off or in an inactive state, program instructions and data may be stored in a long-term memory, for example, a non-volatile magnetic, optical, or electronic memory storage device (also not shown). Either or both of the RAM or the storage device may comprise a non-transitory computer-readable medium holding program instructions, that when executed by the processor 1518, cause the apparatus 1502 to perform a method or operations as described herein. Program instructions may be written in any suitable high-level language, for example, C, C++, C#, or Java™, and compiled to produce machine-language code for execution by the processor. Program instructions may be grouped into functional modules, to facilitate coding efficiency and comprehensibility. It should be appreciated that such modules, even if discernable as divisions or grouping in source code, are not necessarily distinguishable as separate code blocks in machine-level coding. Code bundles directed toward a specific type of function may be considered to comprise a module, regardless of whether or not machine code on the bundle can be executed independently of other machine code. In other words, the modules may be high-level modules only.

In a related aspect, the processor 1518 may receive a user identifier associated with the vaporizer 1508 and/or mobile computing device 1528 and store the user identifier in a memory. A user identifier may include or be associated with user biometric data, that may be collected by a biometric sensor or camera included in the assembly 1502 or in a connected or communicatively coupled ancillary device 1528, such as, for example, a smart phone executing a vaporizer interface application. The processor 1518 may generate data indicating a quantity of the vaporizable material consumed by the vaporizer 1508 in a defined period of time, and save the data in the memory device. The processor 1518 and other electronic components may be powered by a suitable battery, as known in the art, or other power source.

The Vape-Bot 1500 may include a gas chromatograph and mass spectrometer (GC-MS) that includes a gas chromatograph 1514 with its output coupled to an input of the mass spectrometer 1516. The gas chromatograph may include a capillary column which depends on the column's dimensions (length, diameter, film thickness) as well as the phase properties (e.g. 5% phenyl polysiloxane). The difference in the chemical properties between different molecules in a mixture and their relative affinity for the stationary phase of the column will promote separation of the molecules as the sample travels the length of the column. The molecules are retained by the column and then elute (come off) from the column at different times (called the retention time), and this allows the mass spectrometer downstream to capture, ionize, accelerate, deflect, and detect the ionized molecules separately. The mass spectrometer does this by breaking each molecule into ionized fragments and detecting these fragments using their mass-to-charge ratio. These and other details of the GC/MS may be as known in the art.

The gas sensor circuit 1524 may include an array of one or more gas sensors, any one or more of which may be independently controllable and readable by the processor 1518. Any one or more of the sensors of the array may be, or may include, an electrochemical sensor configured to detect an electrical signal generated by a chemical reaction between a component of the sensor and the gas analyte. Any one or more of the sensors of the array may be, or may include, a carbon nanotube sensor, which may be considered a variety of electro chemical sensor. Many different electrochemical sensors are known in the art for detecting specific materials. Any one or more of the sensors of the array may be, or may include, an infrared absorption sensor that measures an amount of absorption of infrared radiation at different wavelengths. Any one or more of the sensors of the array may be, or may include, a semiconductor electrochemical sensor, which changes semi conductive properties in response to a chemical reaction between a component of the sensor and an analyte. Any other suitable gas or vapor sensor may be user The gas sensor circuit 1524 may also include gas sensors of other types, for example, optical sensors for measuring vapor density, color or particle size, temperature sensors, motion sensors, flow speed sensors, microphones or other sensing devices.

In related aspects, the assembly may include a transmitter port 1520 coupled to the processor. The memory may hold a designated network address, and the processor 1518 may provide data indicating measurement data of vapor or air analyzed, or amount of material emitted by the vaporizer, and related information, to the designated network address in association with the user identifier, via the transmitter port 1520.

An ancillary device, such as a smartphone 1528, tablet computer, or similar device, may be coupled to the transmitter port 1514 via a wired coupling 1522 or wireless coupling 1520. The ancillary device 1528 may be coupled to the processor 1518 for providing user control input to a gas measurement or vaporizer control process operated executing on the processor 1518. User control input may include, for example, selections from a graphical user interface or other input (e.g., textual or directional commands) generated via a touch screen 1530, keyboard, pointing device, microphone, motion sensor, camera, or some combination of these or other input devices, which may be incorporated in the ancillary device 1528. A display 1530 of the ancillary device 1528 may be coupled to a processor therein, for example via a graphics processing unit (not shown) integrated in the ancillary device 1528. The display 1530 may include, for example, a flat screen color liquid crystal (LCD) display illuminated by light-emitting diodes (LEDs) or other lamps, a projector driven by an LED display or by a digital light processing (DLP) unit, or other digital display device. User interface output driven by the processor 1518 may be provided to the display device 1530 and output as a graphical display to the user. Similarly, an amplifier/speaker or other audio output transducer of the ancillary device 1528 may be coupled to the processor 1518 via an audio processing system. Audio output correlated to the graphical output and generated by the processor 1518 in conjunction with the ancillary device 1528 may be provided to the audio transducer and output as audible sound to the user.

The ancillary device 1528 may be communicatively coupled via an access point 1540 of a wireless telephone network, local area network (LAN) or other coupling to a wide area network (WAN) 1544, for example, the Internet. A server 1538 may be coupled to the WAN 1544 and to a database 1548 or other data store, and communicate with the apparatus 1502 via the WAN and coupled device 1528. In alternative embodiments, functions of the ancillary device 1528 may be built directly into the apparatus 1502, if desired.

Figure 16:
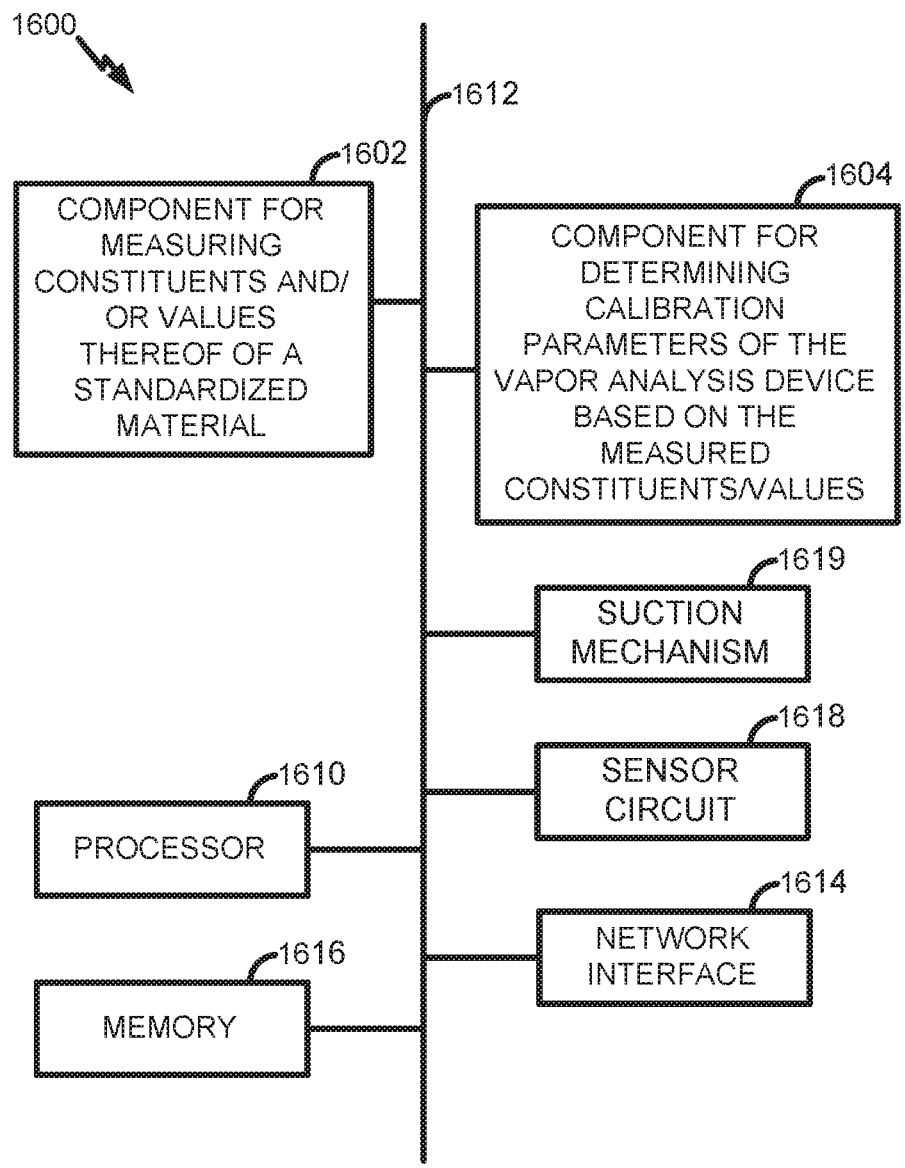
FIG. 16 is a block diagram illustrating aspects of an apparatus for testing output of a personal vaporizer.

FIG. 16 is a block diagram illustrating components of an apparatus or system 1600 for measuring a vaporizer output, in accord with the foregoing examples. The apparatus or system 1600 may include additional or more detailed components as described herein. For example, the processor 1610 and memory 1616 may contain an instantiation of a controller for an RVD as described herein. As depicted, the apparatus or system 1600 may include functional blocks that can represent functions implemented by a processor, software, or combination thereof (e.g., firmware).

As illustrated in FIG. 16, the apparatus or system 1600 may comprise an electrical component 1602 for measuring at least one vapor constituent of a standardized material. The component 1602 may be, or may include, a means for controlling measuring the vapor constituent. Said means may include the processor 1610 coupled to the memory 1616, and to the network interface 1614 and a gas sensor circuit or GC/MS equipment, the processor executing an algorithm based on program instructions stored in the memory. Such algorithm may include a sequence of more detailed operations, for example, obtaining test parameters, drawing a known volume of the material, and calculating the test results.

The apparatus or system 1600 may further comprise an electrical component 1604 for determining calibration parameters of the vapor analysis device. The component 1604 may be, or may include, a means for determining the calibration parameters. Said means may include the processor 1610 coupled to the memory 1616, and to the network interface 1614, the processor executing an algorithm based on program instructions stored in the memory. Such algorithm may include a sequence of more detailed operations, for example, using any of the methods as described herein, or any other suitable method.

The apparatus 1600 may include a processor module 1610 having at least one processor, in the case of the apparatus 1600 configured as a controller configured to operate sensor circuit 1618 and suction mechanism 1619 and other components of the apparatus. The processor 1610, in such case, may be in operative communication with the memory 1616, interface 1614 or dispenser/vaporizer 1618 via a bus 1612 or similar communication coupling. The processor 1610 may effect initiation and scheduling of the processes or functions performed by electrical components 1602-1604.

In related aspects, the apparatus 1600 may include a network interface module operable for communicating with a server over a computer network. The apparatus may include a sensor network 1618 for sensing a vaporizable material, for example, one or more of the sensors described herein above, or a GC/MS system. The apparatus may include a suction mechanism 1619, as described herein above, for drawing on a vaporizer device, or drawing an air sample from an ambient environment. In further related aspects, the apparatus 1600 may optionally include a module for storing information, such as, for example, a memory device/module 1616. The computer readable medium or the memory module 1616 may be operatively coupled to the other components of the apparatus 1600 via the bus 1612 or the like. The memory module 1616 may be adapted to store computer readable instructions and data for enabling the processes and behavior of the modules 1602-1604, and subcomponents thereof, or of the method 1800 and one or more of the additional operations disclosed herein. The memory module 1616 may retain instructions for executing functions associated with the modules 1602-1604. While shown as being external to the memory 1616, it is to be understood that the modules 1602-1604 can exist within the memory 1616.

Figure 17:
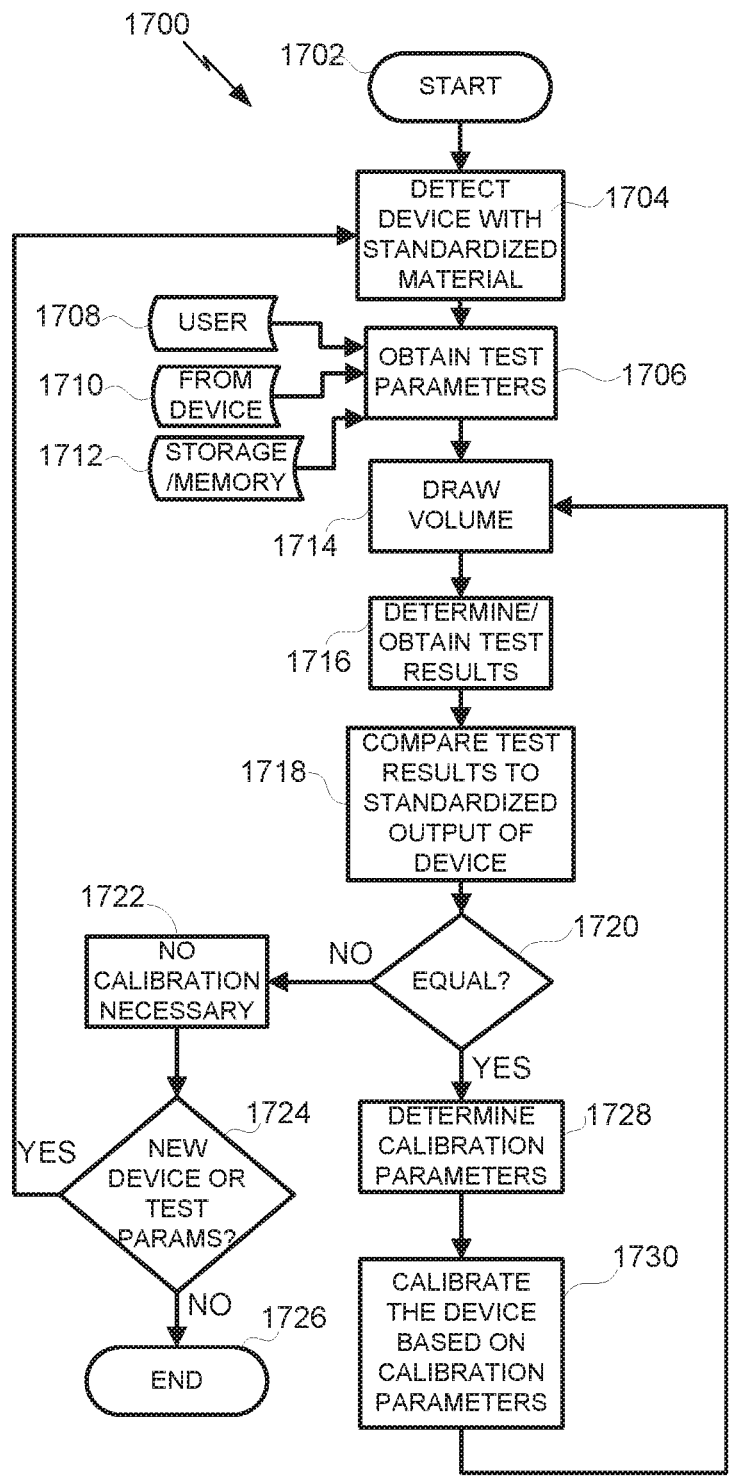
FIG. 17 illustrates an exemplary method.

An example of a control algorithm 1700 is illustrated by FIG. 17, for execution by a processor of an RVD as described herein, which includes independently controllable gas sensor array and GC/MS equipment. The algorithm 1700 may be triggered by activation of the device at 1702, for example when a user places a standardized vapor device in an inlet port or calibration port of the RVD and activates a power-on switch or control, or a particular input or set of inputs. At 1704, the processor may detect the device having the standardized materials. For example, this may be via a sensor or other detector, user input, or other input.

The processor may obtain a set of test or measurement parameters 1706 based on user input 1708, the standardized vapor device 1710, and/or from a local or remote memory or storage. The parameters may include one or more constituents for which the assembly should be calibrated, the quantities, volumes, etc. of the constituents within the standardized materials, whether one or more components of the assembly are believed to be improperly operating, whether the standardized material is a solid, liquid, or gas, whether a GC/MS, other gas sensor or other sensor is to be used, or other input test parameters. For example, the assembly may determine an identifier of the device, such as through an optical, RFID, magnetic, or other sensor, or through another communication channel, such as Wi-Fi, Bluetooth, 802.11 standards, or the like. In some embodiments, the processor may receive a user input having the identifier. The processor may search a memory or database for the identifier, the memory or database storing the identifier and corresponding test parameters for the standardized vapor device. In some embodiments, the device may include data including the test parameters and the processor may be able to receive this data via a communication channel.

At 1714, the processor sends control data to an actuator for a suction mechanism, which causes the suction mechanism to draw a volume of a specified amount according to a specified flow rate. The flow rate for the draw may be constant or variable based on a rate curve. The flow rate may be standardized such that the sensors can detect based on known constituents and a known rate.

At 1716, the sensors detect one or more constituents of the standardized material. The processor receives the data detected by the sensors. In some embodiments the processor may determine constituents and/or quantities based on the detected data. In some embodiments, the processor may transmit the detected data to a remote vapor analysis device for determining the constituents and/or quantities thereof.

At 1718, the processor compares the measurement of the constituent to the known values of the constituent. The known values and the measured values may be equal, indicating that the assembly is properly calibrated for the constituent, as shown at 1722, or may be inequal, indicating that the assembly should be calibrated. At 1724, the processor determines whether the assembly should be tested using a new device and/or new test parameters, and if not, the method 1700 ends at 1726. At 1726, the processor may generate an output indicating that the calibration is complete. The processor may or may not also output data indicating the calibration parameters. In some embodiments, the processor may output data indicating the calibration parameters throughout the method 1700.

At 1728, the processor determines calibration parameters that may indicate how the assembly can be calibrated to more accurately detect measurements of constituents. For example, the difference between the known constituents/amounts and the detected constituents/amounts can be used to determine the calibration parameters. In some embodiments, the processor 1502 can calibrate the assembly 1502 by automatically adjusting a measurement parameter of the assembly 1502. For example, settings for a sensor may be adjusted, constituent determination parameters of the processor can be adjusted, or the like.

In embodiments, the processor may perform one or more predetermined diagnostic tests based on the difference between the known constituents/amounts and the detected constituents/amounts. For example, the processor can recalibrate a component of the GC, the MS, or the gas sensor. For example, the recalibration may include physically altering portions of the components, electronically altering electrical portions (including any electrical hardware), or the like. The processor can also adjust data ratios in databases. For example, a database may include a ratio of a detected value and a measurement value and the processor may change this ratio so that the measurement value more accurately represents the actual value. The processor can also adjust an intake volume, in case a smaller or larger volume results in the sensors/processor more accurately determining the actual constituents/amounts. The processor may also indicate whether a sensor requires replacement and either electrically replace the sensor with a different sensor, or output data indicating that the sensor requires replacement. The processor may also determine that internal mechanisms of the assembly require cleaning and may initiate an automatic cleaning system, or may output data indicating that at least one mechanism requires cleaning and/or the particular mechanism(s). The processor may also check power systems of the assembly to determine whether a desired amount of power is being provided to each associated electrical component. The processor may also determine whether a connection status of the communication port is properly transmitting and/or receiving data, and may attempt to repair the connection if not, and/or output data indicating that the communications are not properly established.

In some embodiments, the processor 1518 can communicate with other vapor analysis devices via a communication port. For example, the processor may transmit the detected data to the other vapor analysis device such that the other device determines the constituents and quantities thereof. The processor may compare constituents determined by the assembly to constituents determined by the other device and use this information to determine calibration parameters. When the assembly processor determines that the assembly is calibrated, the processor may generate an output indicating the completed calibration.

At 1730, the processor either causes the calibration parameters to be implemented, and/or generates an output viewable by a user or other system indicating the calibration parameters, or instructions for adjusting the assembly for the calibration parameters to take effect.

Figure 18:
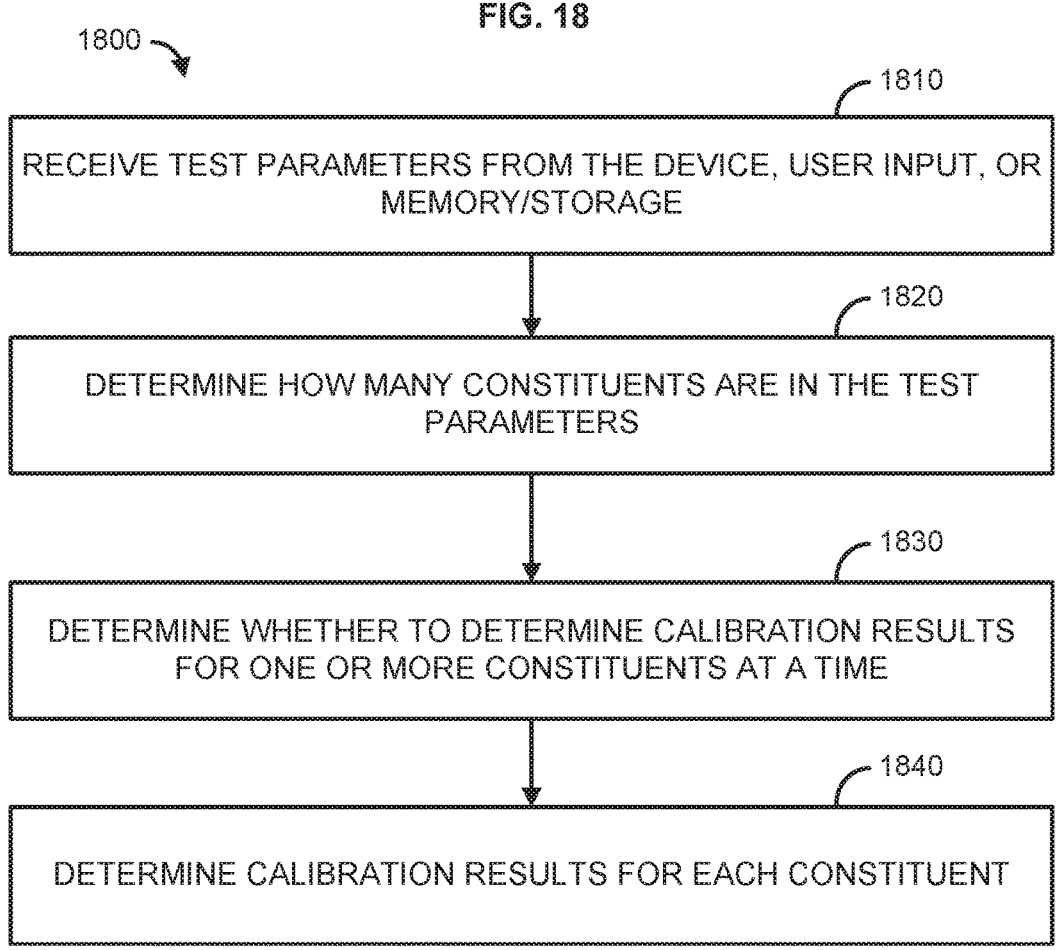
FIG. 18 illustrates an exemplary method.

In view the foregoing, and by way of additional example, FIG. 18, FIG. 19, FIG. 20, FIG. 21, and FIG. 22 show aspects of a method or methods for determining test parameters for a calibration test, as may be performed by a vapor analysis device as described herein, alone or in combination with other elements of the disclosed systems. The vapor analysis device can comprise one or more of the devices disclosed herein. Referring to FIG. 18, the method 1800 may include, at 1810, receiving the test parameters from at least one of the standardized vapor device, a user input, or from a memory/storage. As described above, this may be directly received from a user and/or the standardized vapor device, or may be determined based on a received identifier of the standardized vapor device.

The method 1800 may further include, at 1820, determining how many constituents are included in the test parameters. This information may be included in the received/determined test parameters, or may be received separately. For example, a standardized vapor device may be associated with one or more known constituents for calibration. After obtaining an identifier for the standardized device by reading from the device or from user input, the processor of the test equipment may query a remote or local database to obtain test parameters and/or a test protocol suitable for the identified device. Likewise, if the device under test is not a standard device, but is a known model, the processor may obtain a suitable test parameters and/or a test protocol by querying based on the model number. In alternative embodiments, or in addition, the processor may determine which parameters, and/or how many parameters, to include in the test based on a default test protocol, based on a user-specified protocol, based on a recommendation from another user or user group, or other source.

The method 1800 may include determining whether to determine calibration results for one or more constituents at a time at 1830. Calibration of the assembly may be best accomplished by determining the parameters for each constituent separately. In that regard, the test parameters and/or user input may indicate whether to check each constituent separately, check groups of constituents at a time, or check all constituents at a time. The determination may be based on test protocol information, which may be obtained as noted above.

At 1840, the method 1800 may include determining the calibration parameters for each constituent or group of constituents based on the result of 1830. This may include, for each constituent, running a test protocol that include drawing a specified volume of vapor or aerosol from the device under test as a specified rate, thereby collecting a sample. Then, the test apparatus may expose one or more chemical sensors to the sample, and record sensor readings. After the readings are completed, the sample may be purged from the sample chambers with ambient air and/or with a purified gas from a controlled source, e.g., from a nitrogen cartridge.

Figure 19:
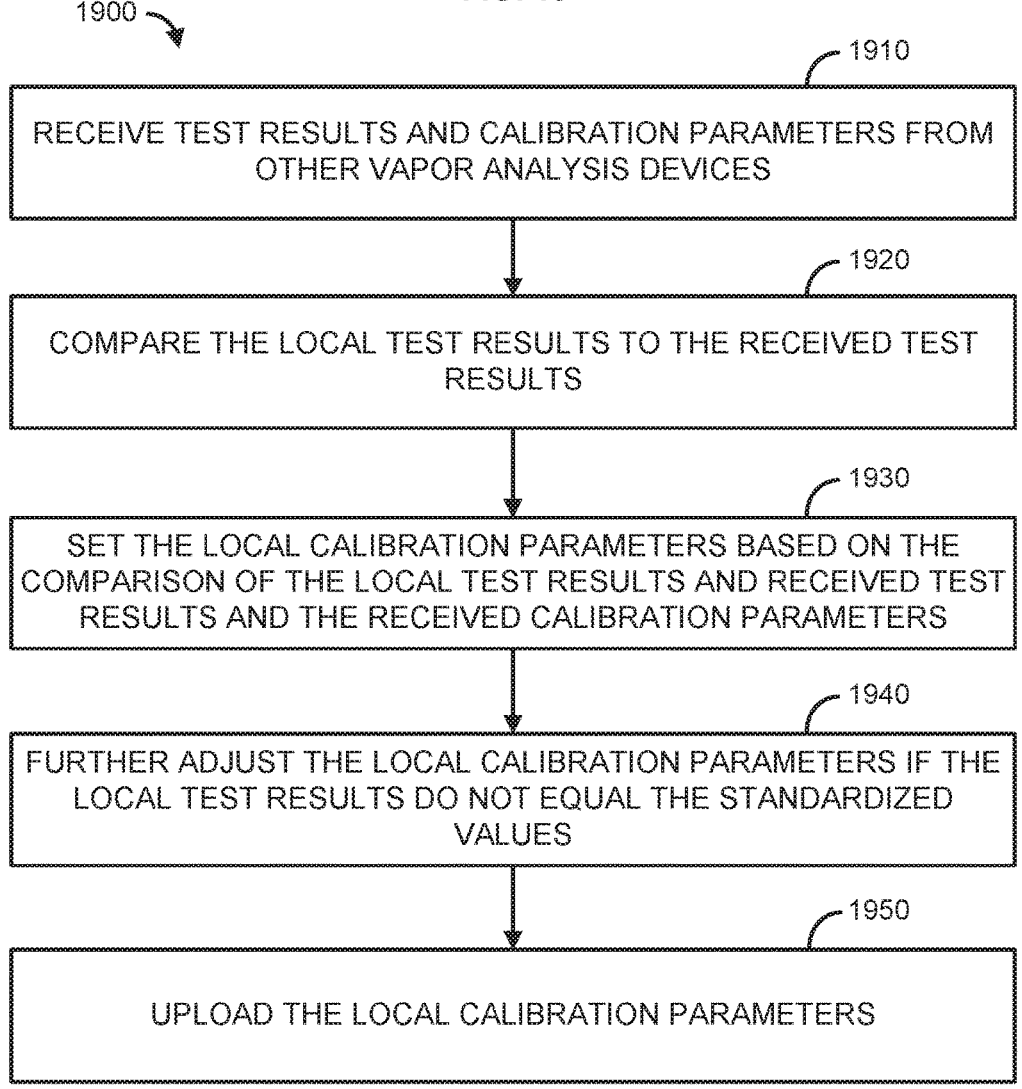
FIG. 19 illustrates an exemplary method.
Figure 20:
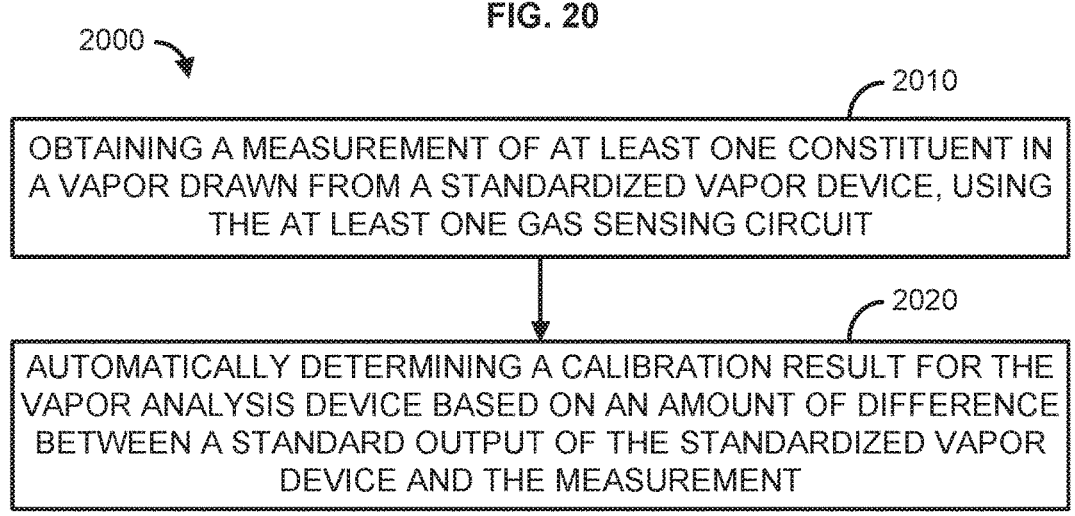
FIG. 20 illustrates an exemplary method.
Figure 21:
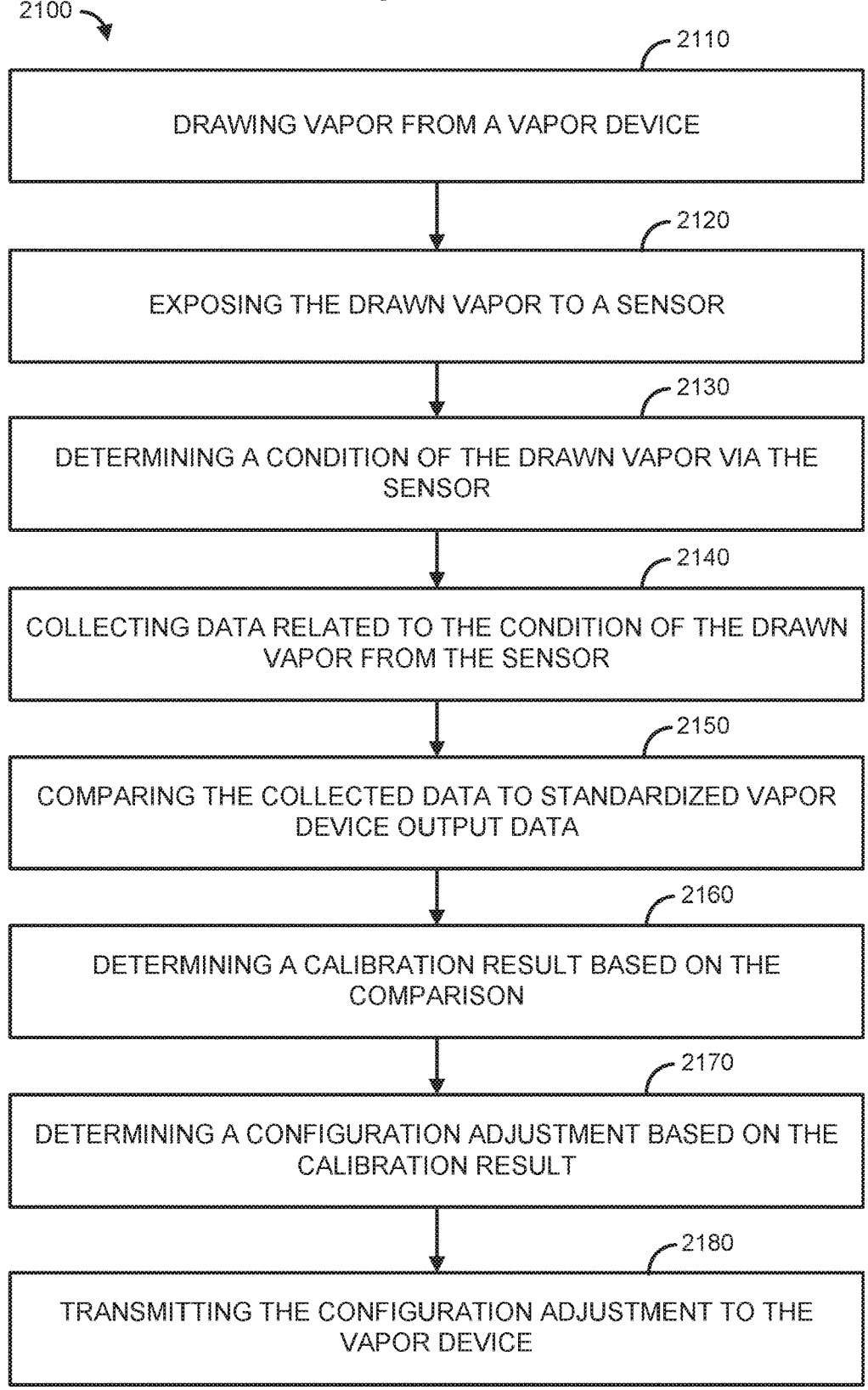
FIG. 21 illustrates an exemplary method.

By way of illustrating aspects, FIG. 19 illustrates a method or methods for determining calibration parameters, as may be performed by a vapor analysis device as described herein, alone or in combination with other elements of the systems disclosed. The vapor analysis device can be the devices disclosed herein. Referring to FIG. 19, the method 1900 may include receiving test results and calibration parameters from other vapor analysis devices at 1910. These test results and calibration parameters may be received directly from the devices or via an intermediary device, such as a server, or may be stored in a local or remote memory. The test results may indicate a measurement of a constituent detected by another device, and the resulting calibration parameters used to properly calibrate the device.

At 1920, the local test results are compared to the received test results. In embodiments, the processor may compare the local test results to the received test results to determine if one of the received test results is close to the local test results, or may determine which received test result is closest in value to the local test results.

At 1930, the processor may set the local calibration parameters based on the results of 1920. This setting of the local calibration parameters may also be based on other information, such as an algorithm or the like. For example, if a matching test result is received, the assembly may set the local calibration parameters equal to the received calibration parameters corresponding to the matching received test result. As another example, the processor may use one or more non-matching test results to zero predict a calibration parameter that will cause the local test results to be similar to the known standardized values of the standardized vapor device.

At 1940, the processor may again cause the assembly to determine local test results to see if they match the known standardized constituents. If the local test results match, then the calibration parameters can be set to the determined value and the assembly is calibrated. However, if the local test results do not match the known standardized values, the processor can adjust the local calibration parameters and re-test to determine if the local test results match the known standardized values.

At 1950, the processor may upload the original test results and the final calibration parameters to another device and/or storage. This data can be used to further improve an algorithm for calibration parameters, may be used by another device for calibrating a particular assembly, or may be otherwise used for improving calibration parameter determination.

A system is disclosed for calibrating an apparatus comprising a suction mechanism configured to draw an output from a personal vaporizer, wherein the suction mechanism is operatively coupled to a particulate testing assembly that can be configured to determine constituents of at least one of a gas, a liquid, or a solid, and a memory holding standardized output data associated with an identifier for a standardized vapor device.

The system can further comprise a processor configured to obtain the identifier of the standardized vapor device for looking up the standardized output data. The processor can be further configured to obtain the identifier by at least one of receiving data from an optical sensor sensing an optical code associated with the standardized vapor device, communicating with an RFID device associated with the standardized vapor device, or receiving data from an electronic memory associated with the standardized vapor device. The processor can be operatively coupled to at least one of the particulate testing assembly, a network communication device, or a suction mechanism for drawing output from the standardized vapor device. The processor can be further configured for obtaining a measurement of at least one constituent in the output drawn from the standardized vapor device, using the at least one gas sensing assembly. The processor can be further configured for automatically determining a calibration result for the vapor analysis device based on an amount of difference between a standard output of the standardized vapor device and the measurement.

The system can further comprise a calibration inlet configured for coupling to outlet of the standardized vapor device, and wherein the processor can be configured for controlling a rate at which air can be drawn into an interior volume. The processor can be further configured for determining the calibration result at least in part by automatically adjusting a measurement parameter of the vapor analysis device based on the amount of difference. The processor can be further configured for determining the calibration result at least in part by performing one or more predetermined diagnostic tests based on the amount of difference. The processor can be further configured for performing the one or more predetermined diagnostic tests at least in part by recalibration of a mass spectrometry component, recalibration of a gas sensing circuit, adjustment of data ratios in the correlated databases, replacement or adjustment of sensors, adjustment of intake volume, cleaning of internal mechanisms via manual or automatic systems, checking of power systems, or checking data transmission fidelity. The processor can be further configured for performing the one or more predetermined diagnostic tests at least in part by communicating with one or more additional vapor analysis devices coupled to the vapor analysis device by a network. The processor can be further configured for at least one of comparing the measurement to similar measurements from the one or more additional vapor analysis devices or providing the measurement to the one or more additional vapor analysis devices. The processor can be further configured for determining the calibration result at least in part by confirming that the vapor analysis device can be calibrated by outputting confirmation data.

A method 2000 is disclosed for calibrating a vapor analysis device that includes at least one particulate sensing circuit that can be configured to determine constituents of at least one of a gas, a liquid, or a solid and a processor, the method 2000 comprising obtaining a measurement of at least one constituent in a vapor drawn from a standardized vapor device, using the at least one gas sensing circuit at 2010 and automatically determining a calibration result for the vapor analysis device based on an amount of difference between a standard output of the standardized vapor device and the measurement at 2020. The method 2000 can further comprise coupling an outlet of the standardized vapor device to a calibration inlet of the vapor analysis device, and drawing air into an interior volume at a rate controlled at least in part by the processor.

Determining the calibration result can comprise automatically adjusting a measurement parameter of the vapor analysis device based on the amount of difference. Determining the calibration result can comprise performing one or more predetermined diagnostic tests based on the amount of difference. The one or more predetermined diagnostic tests comprise recalibration of a mass spectrometry component, recalibration of a gas sensing circuit, adjustment of data ratios in the correlated databases, replacement or adjustment of sensors, adjustment of intake volume, cleaning of internal mechanisms via manual or automatic systems, checking of power systems, or checking data transmission fidelity. The one or more predetermined diagnostic tests comprise communicating with one or more additional vapor analysis devices coupled to the vapor analysis device by a network.

The method 2000 can further comprise comparing the measurement to similar measurements from the one or more additional vapor analysis devices. The communicating can comprise providing the measurement to the one or more additional vapor analysis devices. Determining the calibration result can comprise confirming that the vapor analysis device can be calibrated by outputting confirmation data.

The method 2000 can further comprise at least one of analyzing the measurement data by the processor, or sending the measurement data to a network node. Obtaining the measuring can comprise at least one of gas chromatography, mass spectrometry, electrochemical detecting, carbon nanotube detecting, infrared absorption, semiconductor electrochemical sensing, or any other measuring of gasses, liquids, or solids.

In an aspect, an apparatus is disclosed comprising an intake, configured to be coupled to a vapor device, a pump coupled to the air intake, configured for drawing vapor from the vapor device via the intake, a sensor, coupled to the pump, configured for detecting a condition of the drawn vapor, a memory, configured for storing standardized vapor device output data, a processor, coupled to the memory and the sensor, configured for, collecting data related to the condition of the drawn vapor from the sensor, comparing the collected data to the standardized vapor device output data, determining a calibration result based on the comparison, and determining a configuration adjustment based on the calibration result, and a network access device, coupled to the processor, configured for transmitting the configuration adjustment to the vapor device.

The pump can comprise at least one of a variable stroke piston, variable stroke bellows, an intake fan, osmosis intake structure, or a gas pump. The pump can be configured to draw the vapor into the apparatus at a rate controlled at least in part by the processor.

The sensor can comprise at least one of a gas sensor circuit, a true/false test strip, a PH sensor, a frequency reading device, a temperature reading device, a magnetic sensor, an imaging sensor, a gas chromatograph, a mass spectrometer, or a combination thereof. The condition can comprise one or more of, a type of vaporizable material, a mixture of vaporizable material, a temperature, a color, a concentration, a quantity, a toxicity, a pH, a vapor density, a particle size, an identification of a constituent.

The network access device can be further configured for transmitting the collected data to a computing device. The network access device can be further configured to receive the configuration adjustment from the computing device.

The apparatus can further comprise an analysis chamber, coupled to the pump, configured for receiving the drawn vapor and exposing the drawn vapor to the sensor. The apparatus can further comprise an exhaust coupled to the analysis chamber, configured for expelling the vapor. The apparatus can further comprise a display device configured for providing one or more visual outputs related to the calibration result.

The processor can be further configured to control vapor output of the vapor device. The processor can be further configured for receiving an identifier of the vapor device, determining a type of vapor device based on the identifier, determining a standardized vapor device based on the type of vapor device, and determining the standardized vapor device output based on the determined standardized vapor device. The apparatus can further comprise a vapor device identification component. The vapor device identification component can comprise one or more of an optical sensor configured for sensing an optical code associated with the vapor device or an RFID device configured for receiving the identifier.

Determining a configuration adjustment based on the calibration result can comprise determining a setting of the vapor device associated with the calibration result, determining a value to increment or decrement the setting, and storing the value and the setting as the configuration adjustment. Comparing the collected data to the standardized vapor device output data can comprise determining a standardized vapor device based on identifying closest matching standardized vapor device output data based on the comparison.

In an aspect, a method 2100 is disclosed comprising drawing vapor from a vapor device at 2110. The method 2100 can comprise exposing the drawn vapor to a sensor at 2120. The method 2100 can comprise determining a condition of the drawn vapor via the sensor at 2130. Determining the condition of the drawn vapor via the sensor can further comprise at least one of gas chromatography, mass spectrometry, electrochemical detecting, carbon nanotube detecting, infrared absorption, or semiconductor electrochemical sensing. The condition can comprise one or more of, a type of vaporizable material, a mixture of vaporizable material, a temperature, a color, a concentration, a quantity, a toxicity, a pH, a vapor density, a particle size, an identification of a constituent.

The method 2100 can comprise collecting data related to the condition of the drawn vapor from the sensor at 2140. The method 2100 can comprise comparing the collected data to standardized vapor device output data at 2150. The method 2100 can comprise determining a calibration result based on the comparison at 2160. The method 2100 can comprise determining a configuration adjustment based on the calibration result at 2170. The method 2100 can comprise transmitting the configuration adjustment to the vapor device at 2180. The method 2100 can further comprise receiving an identifier of the vapor device, determining a type of vapor device based on the identifier, determining a standardized vapor device based on the type of vapor device, and determining the standardized vapor device output based on the determined standardized vapor device. Determining a configuration adjustment based on the calibration result can comprise determining a setting of the vapor device associated with the calibration result, determining a value to increment or decrement the setting, and storing the value and the setting as the configuration adjustment. Comparing the collected data to the standardized vapor device output data can comprise determining a standardized vapor device based on identifying closest matching standardized vapor device output data based on the comparison.

In an aspect, an apparatus is disclosed comprising an intake, configured to be coupled to a standardized vapor device, a pump coupled to the air intake, configured for drawing vapor from the standardized vapor device via the intake, a sensor, coupled to the pump, configured for detecting a condition of the drawn vapor, a memory, configured for storing standardized vapor device output data, a processor, coupled to the memory and the sensor, configured for, collecting data related to the condition of the drawn vapor from the sensor, comparing the collected data to the standardized vapor device output data, determining a calibration result based on the comparison, and determining a configuration adjustment based on the calibration result, and applying the configuration adjustment to the apparatus.

The pump can comprise at least one of a variable stroke piston, variable stroke bellows, an intake fan, osmosis intake structure, or a gas pump. The pump can be configured to draw the vapor into the apparatus at a rate controlled at least in part by the processor.

The sensor can comprise at least one of a gas sensor circuit, a true/false test strip, a PH sensor, a frequency reading device, a temperature reading device, a magnetic sensor, an imaging sensor, a gas chromatograph, a mass spectrometer, or a combination thereof. The condition can comprise one or more of, a type of vaporizable material, a mixture of vaporizable material, a temperature, a color, a concentration, a quantity, a toxicity, a pH, a vapor density, a particle size, an identification of a constituent.

The apparatus can further comprise a network access device configured for transmitting the collected data to a computing device. The network access device can be further configured to receive the configuration adjustment from the computing device. The apparatus can further comprise an analysis chamber, coupled to the pump, configured for receiving the drawn vapor and exposing the drawn vapor to the sensor. The apparatus can further comprise an exhaust coupled to the analysis chamber, configured for expelling the vapor.

The apparatus can further comprise a display device configured for providing one or more visual outputs related to the calibration result. The processor can be further configured to control vapor output of the standardized vapor device.

The processor can be further configured for receiving an identifier of the standardized vapor device and determining the standardized vapor device output based on the identifier. The apparatus can further comprise a standardized vapor device identification component. The standardized vapor device identification component can comprise one or more of an optical sensor configured for sensing an optical code associated with the standardized vapor device or an RFID device configured for receiving the identifier.

Determining a configuration adjustment based on the calibration result can comprise determining a setting of the apparatus associated with the calibration result, determining a value to increment or decrement the setting, and storing the value and the setting as the configuration adjustment. Comparing the collected data to the standardized vapor device output data can comprise determining a standardized vapor device based on identifying closest matching standardized vapor device output data based on the comparison. The processor can be further configured for determining the calibration result at least in part by performing one or more predetermined diagnostic tests based on the comparison.

The processor can be further configured for performing the one or more predetermined diagnostic tests at least in part by recalibration of a mass spectrometry component, recalibration of a gas sensing circuit, adjustment of data ratios in a database, replacement or adjustment of sensors, adjustment of an intake volume, cleaning of internal mechanisms via manual or automatic systems, checking of power systems, or checking data transmission fidelity, communicating with one or more additional vapor analysis devices via a network access device.

In an aspect, a method 2200 is disclosed comprising drawing vapor from a standardized vapor device at 2210. The method 2200 can comprise exposing the drawn vapor to a sensor at 2220. The method 2200 can comprise determining a condition of the drawn vapor via the sensor at 2230. The method 2200 can comprise collecting data related to the condition of the drawn vapor from the sensor at 2240. The method 2200 can comprise comparing the collected data to standardized vapor device output data at 2250. The method

2200 can comprise determining a calibration result based on the comparison at 2260. The method 2200 can comprise determining a configuration adjustment based on the calibration result at 2270. The method 2200 can comprise applying the configuration adjustment at 2280.

Determining the condition of the drawn vapor via the sensor can further comprise can comprise at least one of gas chromatography, mass spectrometry, electrochemical detecting, carbon nanotube detecting, infrared absorption, or semiconductor electrochemical sensing.

The condition can comprise one or more of, a type of vaporizable material, a mixture of vaporizable material, a temperature, a color, a concentration, a quantity, a toxicity, a pH, a vapor density, a particle size, an identification of a constituent. The method 2200 can further comprise receiving an identifier of the standardized vapor device and determining the standardized vapor device output based on the identifier. Determining a configuration adjustment based on the calibration result can comprise determining a setting associated with the calibration result, determining a value to increment or decrement the setting, and storing the value and the setting as the configuration adjustment. Comparing the collected data to the standardized vapor device output data can comprise determining a standardized vapor device based on identifying closest matching standardized vapor device output data based on the comparison. The method 2200 can further comprise performing one or more predetermined diagnostic tests based on the comparison.

In view of the exemplary systems described supra, methodologies that can be implemented in accordance with the disclosed subject matter have been described with reference to several flow diagrams. While for purposes of simplicity of explanation, the methodologies are shown and described as a series of blocks, it is to be understood and appreciated that the claimed subject matter is not limited by the order of the blocks, as some blocks may occur in different orders and/or concurrently with other blocks from what is depicted and described herein. Moreover, not all illustrated blocks can be required to implement the methodologies described herein. Additionally, it should be further appreciated that the methodologies disclosed herein are capable of being stored on an article of manufacture to facilitate transporting and transferring such methodologies to computers.

Those of skill would further appreciate that the various illustrative logical blocks, modules, circuits, and algorithm steps described in connection with the aspects disclosed herein can be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present disclosure.

As used in this application, the terms "component," "module," "system," and the like are intended to refer to a computer-related entity, either hardware, a combination of hardware and software, software, or software in execution. For example, a component can be, but is not limited to being, a process running on a processor, a processor, an object, an executable, a thread of execution, a program, and/or a computer. By way of illustration, both an application running on a server and the server can be a component. One or more components may reside within a process and/or thread of execution and a component can be localized on one computer and/or distributed between two or more computers.

As used herein, a "vapor" includes mixtures of a carrier gas or gaseous mixture (for example, air) with any one or more of a dissolved gas, suspended solid particles, or suspended liquid droplets, wherein a substantial fraction of the particles or droplets if present are characterized by an average diameter of not greater than three microns. As used herein, an "aerosol" has the same meaning as "vapor," except for requiring the presence of at least one of particles or droplets. A substantial fraction means 10% or greater; however, it should be appreciated that higher fractions of small (<3 micron) particles or droplets can be desirable, up to and including 100%. It should further be appreciated that, to simulate smoke, average particle or droplet size can be less than three microns, for example, can be less than one micron with particles or droplets distributed in the range of 0.01 to 1 micron. A vaporizer may include any device or assembly that produces a vapor or aerosol from a carrier gas or gaseous mixture and at least one vaporizable material. An aerosolizer is a species of vaporizer, and as such is included in the meaning of vaporizer as used herein, except where specifically disclaimed.

Various aspects presented in terms of systems can comprise a number of components, modules, and the like. It is to be understood and appreciated that the various systems may include additional components, modules, etc. and/or may not include all of the components, modules, etc. discussed in connection with the figures. A combination of these approaches can also be used.

In addition, the various illustrative logical blocks, modules, and circuits described in connection with certain aspects disclosed herein can be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor can be a microprocessor, but in the alternative, the processor can be any conventional processor, controller, microcontroller, system-on-a-chip, or state machine. A processor may also be implemented as a combination of computing devices, e.g., a combination of a DSP and a microprocessor, a plurality of microprocessors, one or more microprocessors in conjunction with a DSP core, or any other such configuration.

Operational aspects disclosed herein can be embodied directly in hardware, in a software module executed by a processor, or in a combination of the two. A software module may reside in RAM memory, flash memory, ROM memory, EPROM memory, EEPROM memory, registers, hard disk, a removable disk, a CD-ROM, a DVD disk, or any other form of storage medium known in the art. An exemplary storage medium is coupled to the processor such the processor can read information from, and write information to, the storage medium. In the alternative, the storage medium can be integral to the processor. The processor and the storage medium may reside in an ASIC or may reside as discrete components in another device.

Furthermore, the one or more versions can be implemented as a method, apparatus, or article of manufacture using standard programming and/or engineering techniques to produce software, firmware, hardware, or any combination thereof to control a computer to implement the disclosed aspects. Non-transitory computer readable media can include but are not limited to magnetic storage devices (e.g., hard disk, floppy disk, magnetic strips . . . ), optical disks (e.g., compact disk (CD), digital versatile disk (DVD) . . . ), smart cards, and flash memory devices (e.g., card, stick). Those skilled in the art will recognize many modifications can be made to this configuration without departing from the scope of the disclosed aspects.

The previous description of the disclosed aspects is provided to enable any person skilled in the art to make or use the present disclosure. Various modifications to these aspects will be readily apparent to those skilled in the art, and the generic principles defined herein can be applied to other embodiments without departing from the spirit or scope of the disclosure. Thus, the present disclosure is not intended to be limited to the embodiments shown herein but is to be accorded the widest scope consistent with the principles and novel features disclosed herein.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is in no way intended that an order be inferred, in any respect. This holds for any possible non-express basis for interpretation, including: matters of logic with respect to arrangement of steps or operational flow; plain meaning derived from grammatical organization or punctuation; the number or type of embodiments described in the specification.

It will be apparent to those skilled in the art that various modifications and variations can be made without departing from the scope or spirit. Other embodiments will be apparent to those skilled in the art from consideration of the specification and practice disclosed herein. It is intended that the specification and examples be considered as exemplary only, with a true scope and spirit being indicated by the following claims.

The invention claimed is:

1. An emission analysis device comprising:
   a device processor operable for controlling the pharmaceutical analysis device;
   an air intake configured to receive an emission from an associated electronic vapor device;
   a pump component operatively coupled to the device processor and controlled in part by the device processor, wherein the pump component is coupled to the air intake and operable to draw the emission into the air intake;
   at least one sensing component operatively coupled to the device processor and controlled in part by the device processor, wherein the at least one sensing component is configured to be in contact with at least a portion of the emission, wherein the at least one sensing component is operable to detect a plurality of emission data associated with at least one physical characteristic of the emission received from the associated electronic vapor device;
   a memory operatively coupled to the device processor, wherein the memory is operable to store a plurality of standard emission parameters, wherein the standard emission parameters include at least one of a presence of at least one specified constituent in the emission, a specified amount of at least one constituent in the emission, a specified temperature of the emission, a specified color of the emission, a specified pH of the emission, a specified density of the emission, a specified particle size of at least one constituent in the emission, an absence of at least one specified constituent in the emission, a specified concentration of the emission, and combinations thereof;
   an input/output device operatively connected to the device processor and controlled in part by the device processor, wherein the input/output device is operable to connect the device processor to the associated electronic vapor device, wherein the input/output device is operable to transmit data from the device processor to the associated electronic vapor device; and
   a power source operatively coupled to the device processor and operable to generate a supply of power for the operation of the emission analysis device;
   wherein the device processor is further operable to,
      receive at least a portion of the plurality of detected emission data from the at least one sensing component,
      compare at least a portion of the plurality of detected emission data for the emission generated by the associated electronic vapor device to at least a portion of the plurality of standard emission parameters and generate a plurality of comparison data therefrom,
      determine, based on at least a portion of the plurality of comparison data, whether the emission is in accordance with at least one of the plurality of standard emission parameters and generate a plurality of calibration data therefrom,
      determine, based on at least a portion of the plurality of calibration data, whether at least one device configuration of the associated electronic vapor device requires adjustment and generate a plurality of adjustment result data therefrom; and
      transmit, via the input/output device, at least a portion of at least one of the plurality of comparison data, the plurality of calibration data, the plurality of adjustment result data, and combinations thereof to the associated electronic vapor device.

2. The emission analysis device of claim 1, wherein the device processor is further operable to:
   determine, based on at least a portion of the adjustment result data, at least one adjustment to at least one device configuration of the associated electronic vapor device;
   generate at least one command for adjusting the at least one device configuration of the associated electronic vapor device; and
   transmit, via the input/output device, the at least one command to the associated electronic vapor device.

3. The emission analysis device of claim 1, wherein the at least one emission from the electronic vapor device comprises at least one of a vapor, a smoke, a gas, a fluid, and combinations thereof.

4. The emission analysis device of claim 1, wherein the at least one sensing component is selected from the group of sensing components consisting of: a biochemical/chemical sensor, a genetic sensor, a thermal sensor, a radiation sensor, a mechanical sensor, an optical sensor, a magnetic sensor, an electrical sensor, and combinations thereof.

5. The emission analysis device of claim 1, wherein the at least one sensing component is operable to detect at least one of an identification of a constituent in the emission, an amount of a constituent in the emission, a temperature of the emission, heat flow, heat capacity, a color of the emission, a concentration of the emission, an emission pH, an emission density, a particle size of a constituent in the emission, a toxicity level of the emission, a mechanical property of the emission, a magnetic property of the emission, an electrical property of the emission, and combinations thereof.

6. The emission analysis device of claim 1, wherein the memory is further operable to store at least a portion of at least one of: the plurality of detected emission data, the plurality of comparison data, the plurality of calibration data, the plurality of adjustment result data, and combinations thereof.

7. The emission analysis device of claim 1, wherein the pump component comprises at least one of a variable stroke piston, variable stroke bellows, an intake fan, an osmosis intake component, a gas pump, and combinations thereof.

8. The emission analysis device of claim 1, further comprising an input/output interface operatively coupled to the device processor, and wherein the device processor is further operable to receive at least a portion of the standard emission parameters from an associated user via the input/output interface.

9. The emission analysis device of claim 1, further comprising a display operatively coupled to the device processor, wherein the display is operable to display at least a portion of at least one of the plurality of comparison data, the plurality of calibration data, the plurality of adjustment result data, and combinations thereof.

10. The emission analysis device of claim 1, wherein the device processor is further operable to:
obtain a plurality of vapor device identification data related to the associated electronic vapor device;
determine, based on at least a portion of the plurality of vapor device identification data, a type of electronic vapor device; and
determine a plurality of standard emission parameters based on the determined type of electronic vapor device.

11. The emission analysis device of claim 10, wherein the device processor is further operable to:
compare at least a portion of the plurality of detected emission data for the emission generated by the associated electronic vapor device to at least a portion of the plurality of standard emission parameters for the determined type of electronic vapor device and generate a plurality of device comparison data therefrom; and
determine, based on at least a portion of the plurality of device comparison data, whether the emission is in accordance with at least one of the plurality of standard emission parameters for the determined type of electronic vapor device and generate a plurality of calibration data therefrom.

12. The emission analysis device of claim 1,
determine, based on at least a portion of comparison data, a difference between at least a portion of the plurality of detected emission data and at least one standard emission parameter and generate a plurality of difference measurement data therefrom;
determine, based on the difference measurement data, if the difference is within in a predetermined range;
in response to a determination that the difference is not within the predetermined range, determine at least one adjustment to at least one device configuration of the associated electronic vapor device;
generate at least one command for adjusting the at least one device configuration of the associated electronic vapor device; and
transmit, via the input/output device, the at least one command to the associated electronic vapor device.

13. The emission analysis device of claim 12, wherein the device processor is further operable to determine, in response to a determination that the difference is not within the predetermined range, at least one diagnostic action response to be performed by the emission analysis device.

14. The emission analysis device of claim 1, wherein the device processor is further operable to:
determine at least one operational parameter for which the pump component draws the emission into the air intake; and
generate at least one control signal for controlling the operation of the pump component in accordance with the at least one determined operational parameter.

15. The emission analysis device of claim 1, wherein the input/output device is further operable to connect the device processor to an associated network for communication with a plurality of auxiliary emission analysis devices, wherein the input/output device is operable to transmit data from the device processor to at least a portion of the auxiliary vapor devices, wherein the input/output device is operable to receive a plurality of auxiliary data from at least a portion of the plurality of auxiliary emission analysis devices.

16. The emission analysis device of claim 15, wherein the device processor is further operable to:
receive, from the input/output device, at least a portion of the plurality of auxiliary data received from at least a portion of the plurality of auxiliary emission analysis devices;
determine, based on at least a portion of at least one of the plurality of comparison data and the plurality of received auxiliary data, whether the emission is in accordance with at least one of the plurality of standard emission parameters and generate a plurality of calibration data therefrom,
determine, based on at least a portion of at least one the calibration data and the plurality of received auxiliary data, whether at least one device configuration of the associated electronic vapor device requires adjustment and generate a plurality of adjustment result data therefrom.

17. The emissions analysis device of claim 16, wherein the auxiliary data comprises at least one of emission data detected by an auxiliary emission analysis device, comparison data generated by an auxiliary emission analysis device, calibration data generated by an auxiliary emission analysis device, adjustment result data generated by an auxiliary emission analysis device, and combinations thereof.

18. The emission analysis device of claim 1, wherein the input/output device is further operable to connect the device processor to a remote computing device, wherein the input/output device is operable to transmit data from the device processor to the remote computing device for analysis thereof, wherein the input/output device is operable to receive a plurality of analysis data from at least a portion of the plurality of auxiliary emission analysis devices.

19. The emission analysis device of claim 18, wherein the device processor is further operable to:
receive, from the input/output device, at least a portion of the plurality of analysis data received from the remote computing device;
determine, based on at least a portion of at least one of the plurality of comparison data and the plurality of received analysis data, whether the emission is in accordance with at least one of the plurality of standard emission parameters and generate a plurality of calibration data therefrom, determine, based on at least a portion of at least one the calibration data and the plurality of received analysis data, whether at least one device configuration of the associated electronic vapor device requires adjustment and generate a plurality of adjustment result data therefrom.

* * * * *